US011814650B2

(12) United States Patent
Malumbres et al.

(10) Patent No.: US 11,814,650 B2
(45) Date of Patent: Nov. 14, 2023

(54) METHOD FOR EXPANDING STEMNESS AND DIFFERENTIATION POTENTIAL OF PLURIPOTENT CELLS

(71) Applicant: FUNDACIÓN DEL SECTOR PÚBLICO ESTATAL CENTRO NACIONAL DE INVESTIGACIONES ONCOLÓGICAS CARLOS III (F.S.P. CNIO), Madrid (ES)

(72) Inventors: Marcos Malumbres, Guadalix de la Sierra (ES); Maria Salazar-Roa, Madrid (ES); Marianna Trakala, Cambridge, MA (US); Mónica Alvarez-Fernandez, Madrid (ES)

(73) Assignee: FUNDACIÓN DEL SECTOR PÚBLICO ESTATAL CENTRO NACIONAL DE INVESTIGACIONES ONCOLOGICAS CARLOS III (F.S.P. CNIO), Madrid (ES)

( * ) Notice: Subject to any disclaimer, the term of this patent is extended or adjusted under 35 U.S.C. 154(b) by 378 days.

(21) Appl. No.: 16/616,892

(22) PCT Filed: May 25, 2018

(86) PCT No.: PCT/ES2018/063853
§ 371 (c)(1),
(2) Date: Nov. 25, 2019

(87) PCT Pub. No.: WO2018/215662
PCT Pub. Date: Nov. 29, 2018

(65) Prior Publication Data
US 2021/0147804 A1 May 20, 2021

(30) Foreign Application Priority Data
May 26, 2017 (EP) ...................... 17382304

(51) Int. Cl.
*C12N 5/077* (2010.01)
*C12N 5/074* (2010.01)

(52) U.S. Cl.
CPC ......... *C12N 5/0657* (2013.01); *C12N 5/0696* (2013.01); *C12N 2310/141* (2013.01); *C12N 2501/235* (2013.01); *C12N 2501/602* (2013.01); *C12N 2501/603* (2013.01); *C12N 2501/604* (2013.01); *C12N 2501/605* (2013.01); *C12N 2501/608* (2013.01); *C12N 2501/65* (2013.01); *C12N 2501/999* (2013.01); *C12N 2506/02* (2013.01); *C12N 2506/45* (2013.01)

(58) Field of Classification Search
CPC ............ C12N 5/0696; C12N 2310/141; C12N 2501/65
See application file for complete search history.

(56) References Cited

FOREIGN PATENT DOCUMENTS

WO 2014/201254 A1 12/2014

OTHER PUBLICATIONS

Fan (2020, Cancer Gene Therapy, 27:424-437).*
Weinberger (Nature Reviews, Molecular Cell Biology, 2016, 17:155-169).*
M. Abad et al., "Reprogramming in vivo produces teratomas and iPS cells with totipotency features", Nature 502: 340-345 (2013).
Ambros, "The functions of animal microRNAs", insight review articles, Nature 431: 350-355 (2004).
C. Beard et al., "Efficient Method to Generate Single-Copy Transgenic Mice by Site-Specific Integration in Embryonic Stem Cells", Technology Report, Genesis 44: 23-28 (2006).
F.H. Biase et al., "Cell fate inclination within 2-cell and 4-cell mouse embryos revealed by single-cell RNA sequencing", Genome Research 24: 1787-1796 (2014).
J. Bilic et al., "Concise Review: Induced Pluripotent Stem Cells Versus Embryonic Stem Cells: Close Enough or Yet Too Far Apart?", Stem Cells 30: 33-41 (2012).
A. Blattler et al., "Global loss of DNA methylation uncovers intronic enhancers in genes showing expression changes", Genome Biology 15: 469 (2014).
C. Bock et al., "BiQ Analyzer: visualization and quality control for DNA methylation data from bisulfite sequencing", Bioinformatics Applications Note 21(21): 4067-4068 (2005).
M.J. Bueno et al., "Genetic and Epigenetic Silencing of MicroRNA-203 Enhances ABL1 and BCR-ABL1 Oncogene Expression", Cancer Cell Article 13: 496-506 (2008).
D.A. Greer Card et al., "Oct4/Sox2-Regulated miR-302 Targets Cyclin D1 in Human Embryonic Stem Cells", Molecular and Cellular Biology 28(20): 6426-6438 (2008).
S. Chetty et al., "A simple tool to improve pluripotent stem cell differentiation", HHS Public Access, Author Manuscript, Nat. Methods 10(6): 553-556 (2013).

(Continued)

*Primary Examiner* — Valarie E Bertoglio
(74) *Attorney, Agent, or Firm* — Daniel R. Evans; Merchant & Gould P.C.

(57) ABSTRACT

Method for expanding stemness and differentiation potential of pluripotent cells. The invention is based on the finding that increasing micro RNA-203 levels in induced pluripotent stem (iPSCs) or embryonic stem (ESCs) cells improves the quality cell fate potential and ability of these cells to differentiate into multiple cell lineages and to reach further maturation properties without interfering with their self-renewal properties. This effect is mediated through the mi R-203-dependent control of de novo DNA methyltransferases Dnmt3a and Dnmt3b, which in turn regulate the methylation landscape of pluripotent cells. The effect can be achieved by overexpression of micro RNA-203 or by adding micro RNA-203 or analogues thereof to the cell culture medium and can be observed using a variety of cellular and in vivo models. The generated cells are naïve pluripotent cells with an improved capacity to differentiate, that can be used to obtain more efficiently differentiated and mature cells proficient for regenerative medicine strategies.

16 Claims, 20 Drawing Sheets
Specification includes a Sequence Listing.

(56) References Cited

OTHER PUBLICATIONS

J. Choi et al., "Prolonged Mek1/2 suppression impairs the developmental potential of embryonic stem cells", HHS Public Access, Author Manuscript, Nature 548(7666): 219-223 (2017).
Y. Chung et al., "Human Embryonic Stem Cell Lines Generated without Embryo Destruction", Cell Stem Cell Correspondence: 113-117 (2008).
H. J. Lee et al., "Lineage Specific Methylation of the Elf5 Promoter in Mammary Epithelial Cells", Stem Cells, Tissue-Specific Stem Cells 29:1611-1619 (2011).
H. C.Y. Chung et al., "Human Induced Pluripotent Stem Cells Derived Under Feeder-Free Conditions Display Unique Cell Cycle and DNA Replication Gene Profiles", Stem Cells and Development 21(2): 206-216 (2012).
C.R. Gasque Schoof et al., "The Roles of miR-26, miR-29, and miR-203 in the Silencing of the Epigenetic Machinery during Melanocyte Transformation", BioMed Research International, Article ID 634749: 1-11 (2015).
O. Graña et al., "Nextpresso: Next Generation Sequencing Expression Analysis Pipeline", Research Article, Current Bioinformatics 13: 583-591 (2018).
J. Hanna et al., "Direct cell reprogramming is a stochastic process amenable to acceleration", Nature, Articles 462: 595-602 (2009).
H. Honda et al., "Naive-like Conversion Overcomes the Limited Differentiation Capacity of Induced Pluripotent Stem Dells", The Journal of Biological Chemistry 288(36): 26157-26166 (2013).
X. A. Huang et al., "The miRNA Regulation of Stem Cells", NIH Public Access Author Manuscript, Wiley Interdiscip Rev Membr Transp Signal 1(1): 83-95 (2012).
Z.P. Huang et al., "Cardiomyocyte-enriched protein CIP protects against pathophysiological stresses and regulates cardiac homeostasis", Journal of Clinical Investigation 125(11): 4122-4134 (2015).
M. Jackson et al., "Severe Global DNA Hypomethylation Blocks Differentiation and Induces Histone Hyperacetylation in Embryonic Stem Cells", Molecular and Cellular Biology 24(20): 8862-8871 (2004).
K. Kapinas et al., "microRNA-Mediated Survivin Control of Pluripotency", Original Research Article, Journal of Cellular Physiology 230: 63-70 (2015).
S.J. Kattman et al., "Stage-Specific Optimization of Activin/Nodal and BMP Signaling Promotes Cardiac Differentiation of Mouse and Human Pluripotent Stem Cell Lines", Cell Stem Cell 8: 228-240 (2011).
R. Kole et al., "RNA therapeutics: beyond RNA interference and antisense oligonucleotides", Nature Review, Drug Discovery 11: 125-140 (2012).
B. Langmead et al., "Ultrafast and memory-efficient alignment of short DNA sequences to the human genome", Genome Biology 10(3): R25.1-10 (2009).
T.R. Leonardo et al., "The functions of microRNAs in pluripotency and reprogramming", Nature Cell Biology 14(11): 1114-1121 (2012).
H. Li et al., "Fast and accurate long-read alignment with Burrows-Wheeler transform", Bioinformatics Original Paper 26(5): 589-595 (2010).
M. Li et al., "Looking to the future following 10 years of induced pluripotent stem cell technologies", Nature Protocols, 11(9): 1579-1585 (2016).
J. Liao et al., "Targeted disruption of DNMT1, DNMT3A and DNMT3B in human embryonic stem cells", Nature Genetics 47(5): 469-480 (2015).
Shi-Lung Lin et al., "Mir-302 reprograms human skin cancer cells into a pluripotent ES-cell-like state", RNA 14: 2115-2124 (2008).
T. MacFarlan et al., "Embryonic stem cell potency fluctuates with endogenous retrovirus activity", NATURE 487: 57-65 (2012).
A. Marson et al., "Connecting microRNA Genes to the Core Transcriptional Regulatory Circuitry of Embryonic Stem Cells", Cell 134: 521-533 (2008).
C. I. Michel et al., "microRNA-203: Tumor Suppression and Beyond", MicroRNA 2: 118-126 (2013).
T.S. Mikkelsen et al., "Dissecting direct reprogramming through integrative genomic analysis", Nature, Articles 454: 49-56 (2008).
S. Miyata et al., "Myosin Heavy Chain Isoform Expression in the Failing and Nonfailing Human Heart", Circulation Research: 386-390 (2000).
X. Nissan et al., "miR-203 modulates epithelial differentiation of human embryonic stem cells towards epidermal stratification", Developmental Biology 356: 506-515 (2011).
H. Niwa et al., "A parallel circuit of LIF signalling pathways maintains pluripotency of mouse ES cells", Nature Letters 460: 118-122 (2009).
M. Okano et al., "DNA Methyltransferases Dnmt3a and Dnmt3b Are Essential for De Novo Methylation and Mammalian Development", Cell 99: 247-257 (1999).
T.G. Otsuji et al., "Progressie maturation in contracting cardiomyocytes derived from human embryonic stem cells: Qualitative effects on electrophysiological responses to drugs", Stem Cell Research 4: 201-213 (2010).
B. Papp et al., "Reprogramming to pluripotency: stepwise resetting of the epigenetic landscape", Cell Research 21: 486-501 (2011).
B.D. Polizzotti et al., "A cryoinjury model in neonatal mice for cardiac translational and regeneration research", Nature Protocols 11(3): 542-552 (2016).
Rodriguez, "High-efficiency deleter mice show that FLPe is an alternative to Cre-IoxP", nature genetics 25:139-140 (2000).
K.R. Rosenbloom et al., "The UCSC Genome Browser database: 2015 update", Nucleic Acids Research 43, Database issue: D670-D681 (2015).
R. Sandhu et al., Loss of post-transcriptional regulation of DNMT3b by microRNAs: A possible molecular mechanism for the hypermethylation defect observed in a subset of breast cancer cell lines, International Journal of Oncology 41: 721-732 (2012).
F. Schwenk et al., "A cre-transgenic mouse strain for the ubiquitous deletion of IoxP-franked gene segments including deletion in germ cells", Nucleic Acids Research 23(24): 5080-5081 (1995).
A. Shenoy et al., "Regulation of microRNA function in somatic stem cell proliferation and differentiation", Nature Reviews, Molecular Cell Biology 15: 565-576 (2014).
K. Takahashi et al., "Induction of Pluripotent Stem Cells from Mouse Embryonic and Adult Fibroblast Cultures by Defined Factors", Cell 126: 663-676 (2006).
K. Takahashi et al., "A decade of transcription factor-mediated reprogramming to pluripotency", Nature Reviews, Molecular Cell Biology 17: 183-193 (2016).
N. Tapia et al., "Molecular Obstacles to Clinical Translation of iPSCs", Cell Stem Cell Review 19: 298-309 (2016).
K.K.W.TO et al., "A novel miR-203-DNMT3b-ABCG2 regulatory pathway predisposing colorectal cancer development", Research Article (2016).
C. Trapnell et al., "Differential gene and transcript expression analysis of RNA-seq experiments with TopHat and Cufflinks", Nature Protocols 7(3): 562-579 (2012).
S. Volinia et al., "Pluripotent Stem Cell miRNAs and Metastasis in Invasive Breast Cancer", JNCI, Arciel: 1-8 (2014).
J. Wang et al., "Isolation and cultivation of naive-like human pluripotent stem cells based on HERVH expression", Nature Protocols 11(2): 327-347 (2016).
J. Wellner et al., "The EMT-activator ZEB1 promotes tumorigenicity by repressing sternness-inhibiting microRNAs", Nature Cell Biology 11(12): 1487-1504 (2009).
Q. Xu et al., "Overexpression of KLF4 promotes cell senescence through microRNA-203-survivin-p21 pathway", Oncotarget 7(37): 60290-60302 (2016).
R. Yi et al., "A skin microRNA promotes differentiation by repressing 'stemness'", Nature 452: 225-229 (2008).
Q.L. Ying et al., "The ground state of embryonic stem cell self-renewal", Nature 453: 519-523 (2008).
International Search Report and Written Opinion for PCT/EP2018/063853, dated Jun. 28, 2018.
Salazar-Roa et al., Transient exposure to miR-203 enhances the differentiation capacity of established pluripotent stem cells, The EMBO Journal (2020) 2104324 (DOI 10.15252/embj.2019104324).

(56) References Cited

OTHER PUBLICATIONS

Expanded View Figures for Salazar-Roa et al., Transient exposure to miR-203 enhances the differentiation capacity of established pluripotent stem cells, The EMBO Journal (2020) 2104324 (DOI 10.15252/embj.2019104324).
Supplementary Material for Salazar-Roa et al., Transient exposure to miR-203 enhances the differentiation capacity of established pluripotent stem cells, The EMBO Journal (2020) 2104324 (DOI 10.15252/embj.2019104324).
Chédin F., The DNMT3 family of mammalian de novo DNA methyltransferases, Prog Mol Biol Transl Sci. 2011;101:255-85 (DOI: 10.1016/B978-0-12-387685-0.00007-X).

* cited by examiner a b a

METHOD FOR EXPANDING STEMNESS AND DIFFERENTIATION POTENTIAL OF PLURIPOTENT CELLS

This application is a National Stage application of PCT/EP2018/063853, filed May 25, 2018, which claims priority to European Patent Application No. 17382304.8, filed May 26, 2017, the contents of all of which are hereby incorporated by reference in their entireties.

FIELD OF THE INVENTION

The present invention relates to a method for improving the potentiality of induced Pluripotent Stem Cells (iPSC) and embryonic stem cells (ESC). More particularly, the present invention refers to a method for increasing the differentiation potential of said cells.

BACKGROUND OF THE INVENTION

Pluripotent stem cells provide an important promise for regenerative medicine due to their self-renewal potential and ability to differentiate into multiple cell lineages.

Pluripotency can be defined as the ability at the single cell level to generate multiple somatic cell lineages as well as germ cells. In the preimplantation embryo, pluripotency is established in the epiblast of the late inner cell mass (ICM), which contains cells that can develop into all tissues other than placenta. These cells can be captured and maintained in culture as embryonic stem cells (ESCs). Both ICM cells and ESCs can contribute to chimeras and colonize the germline reintroduction to the embryo, providing functional proof of their naïve pluripotency. Conversely, neither postimplantation epiblast nor the primed pluripotent stem cells derived from this tissue have the capacity to contribute efficiently to chimeras following blastocyst integration. Therefore, it is well-established that two distinct pluripotent states can be observed in pluripotent cells from mice: the ground or naïve state, exemplified by the mouse embryonic stem cells (mESCs), and the primed pluripotent state represented by mouse postimplantation epiblast stem cells (mEpiSCs). The clearest differences between the two states are: colony morphology, (compact dome shaped in the case of naïve cells and flattened in the case to primed cells), growth factor requirement for maintenance of the pluripotent state (naïve cells are dependent on LIF while primed cells depend on Activin/FGF2), and contribution to chimeras and germline transmission (naïve cells are able to contribute to chimeras while primed cells never do). Naïve pluripotency is then lost in the embryo upon somatic differentiation and can only be reinstated experimentally by reprogramming strategies.

Reprogramming is the process by which adult cells are converted into cells that are in an embryonic stem cell like-state. Full reprogramming of cells can be considered closely related or a synonym of improved functionality and naïve pluripotency.

The original protocol to reprogram somatic cells to induced pluripotent cells (iPSC) was established in 2006 by Yamanaka and co-workers (Takahashi & Yamanaka, 2006), reason why it is commonly known as the original Yamanaka's protocol, and was disclosed in European Patent EP10970446. It permits the conversion of differentiated somatic cells to a pluripotent state. The original method is based on introducing in the adult cells certain genes important for maintaining the essential properties of embryonic stem cells (ESCs), so that the somatic cells (mouse fibroblasts in the first disclosure) are contacted with a nuclear reprogramming factor comprising a gene product of each one of the following families: Oct family, Klf family and Myc family and, preferably, also a gene product of the Sox family. One of the most commonly used embodiment of such method involves the use of the products of the genes Oct4, Sox2, Klf4 and c-Myc, which are also known by those skilled in the art as the four Yamanaka factors. The abbreviation OSKM is often used for the combination of said four factors.

The cells obtained are called induced pluripotent stem cells (iPSCs), because their pluripotency and growth ability are considered similar to those of embryonic stem cells (ESCs).

iPSCs have attracted much attention due to their potential utility as a tool for drug development, modelling of diseases, and transplantation medicine. Of interest, ethical issues associated with the production of ESCs do not apply to iPSCs, which offer a non-controversial strategy to generate patient-specific stem cell lines. However, before reprogramming can be considered for use as a clinical tool, the efficiency of the process must improve substantially.

Thus, since the first disclosure of the reprogramming method, multiple efforts have focused on improving it. A very important issue has been increasing the efficiency of cellular reprogramming, which is usually low, so that a very low number of naïve iPSCs are obtained from the starting differentiated somatic cells. Simply adding transcription factors to a population of differentiated cells does not guarantee reprogramming: the low efficiency of reprogramming in vitro suggests that additional rare events are necessary to generate naïve iPSCs, and the efficiency of reprogramming decreases even further with fibroblasts that have been cultured for long time periods. Furthermore, the differentiation stage of the starting cell appears to impact directly the reprogramming efficiency; mouse hematopoietic stem and progenitor cells give rise to naïve iPSCs up to 300 times more efficiently than do their terminally-differentiated B- and T-cell counterparts.

Furthermore, an important point is that reported reprogramming frequencies are often based on criteria such as alkaline phosphatase activity and activation of reporter genes. Both naïve iPSCs and ESCs demonstrate important characteristics of pluripotent stem cells, (including expressing stem cell markers and forming tumors containing cell types from all three primitive embryonic layers). However, the naïve pluripotency of iPSCs is not absolutely clear since their efficiency in producing live-born progeny is much reduced compared to ESCs. Therefore, chimera contribution and germline transmission serve as more rigorous demonstration of efficient reprogramming, although quantification of such qualities is technically difficult and not used frequently (reviewed by Bilic and Izpisua Belmonte, 2012).

Increasing the safety of the process by diminishing the transformation potential of the reprogramming factors and the vectors used for their expression has been also a main cause of concern. Strategies to avoid the use of viral transduction or genomic integration are under active development in order to replace the integrative viral vectors initially used to introduce the genes encoding the reprogramming factors into the cells. Besides, multiple efforts have been put into improving the pluripotency properties of the iPSCs by expanding the differentiation potential into a wider variety of cell lineages or by improving maturation properties into specific functional cell types (Li & Izpisua Belmonte, 2016).

For all those reasons, the original protocol of reprogramming of differentiated cells into iPSCs has been the subject of many modifications, most of them consisting on substituting different compounds for one or more of the original Yamanaka factors or using additional RNAs that encode proteins additional to the original factors. Thus, there are now many variants of the iPS protocol, including those using microRNAs or small molecule inhibitors of epigenetic modifiers.

Many small-molecules inhibitors have been found to improve reprogramming efficiency, by inhibiting specific enzymes or signaling pathways. This group includes inhibitors of mitogen-activated protein kinase (MAPK), glycogen synthase kinase 3 beta (GSK3b), transforming growth factor beta (TGF-b), chromatin modifying HDACs (histone deacetylases) or DNMTs (DNA methyltransferases), and many more that can also enhance the reprogramming efficiency in combination with the Yamanaka factors.

Using RNA interference (RNAi) to negatively regulate the expression of epigenetic factors and tumor suppressors also promotes reprogramming. Several studies have shown that using siRNA (small interference RNAs) against differentiated lineage markers together with DNA methyltransferase inhibitors (5-aza-cytidine; AZA) helps to achieve full reprogramming of partially reprogrammed cells (Mikkelsen et al, 2008). RNA interference against the DNA methyltransferase Dnmt1 also helps in the transition from partially reprogrammed state to the pluripotent state and, in fact, the epigenetic memory of pluripotent cells is a factor known to act as a barrier in the establishment of pluripotent cells (Mikkelsen et al, 2008). Several previous works demonstrate that manipulations of DNA methylation, during the reprogramming process, influence the success of reprogramming from somatic cells to pluripotent cells: using demethylases during the reprogramming can potentiate the reprogramming to pluripotent cells, but the obtained pluripotent cells are not useful for applications, since the genetic approach used in those cases is irreversible and pluripotent cells need to re-methylate their DNA for differentiation, what makes the obtained reprogrammed cells useless for regenerative medicines (Papp and Plath, 2011).

The RNAi-mediated knockdown of the tumor suppressors p53 and p21 also accelerates the reprogramming process by increasing the cell division rate (Hanna et al, 2009).

But, beyond their capacity to promote efficient reprogramming, several issues relating to the safety of small molecules need to be carefully addressed. For instance, AZA is known to induce DNA damage and cell death (Mikkelsen et al, 2008). Permanent modifications (genomic or epigenomic) should be avoided, and nowadays, there are no studies indicating the optimization of the dosage or the duration of the chemical treatment to avoid toxicity. Therefore, alternatives for the above mentioned small molecules are being sought, as well as different strategies to inhibit the differentiated state in cellular reprogramming, which strategies should improve, preferably, the full reprogramming of somatic cells to naïve iPSCs.

MicroRNAs (frequently abbreviated as miRNAs, or miR when it is accompanied of the specific identification of one of them) are small (15-25 nucleotides, very often 20-21-nt) non-coding RNAs that can modulate expression of protein-coding RNAs and thus playing multiple functions in the cell (Ambros, 2004). Recent evidences suggest that miRNAs are also linked to pluripotency by controlling the expression of stemness transcription factors, epithelial-mesenchymal trans-differentiation, cell cycle progression or the epigenetic landscape of cells (Shenoy & Blelloch, 2014; Leonardo et al., 2012).

For instance, mir-302-367 are directly linked to the levels of the three transcription factors Oct4, Sox2 and Nanog (Card et al, 2008; Marson et al, 2008). It has been found that one particular miRNA, miR-302, which is expressed abundantly in ESCs, is able to transform human cancer cell lines to cells that resemble ESCs (Lin et al, 2008). Other clusters such as miR-290-295 or miR-106-363 are also co-occupied by Oct4, Sox2 and Nanog promoters (Marson et al, 2008).

Some methods for producing pluripotent stem cells are based in combining the introduction of at least one mRNA into a target cell with introducing at least one miRNA into the target cells. US patent application published as US20150232810A1, for instance, discloses the possibility of producing pluripotent stem cells using miRNAs or miRNA mimics in combination with mRNAs, defining a miRNA mimic as a synthetic miRNA that has enhanced stability due to modified nucleotides or structural modifications (e.g. bulges or loops) and also as small, chemically modified double-stranded RNAs that mimic endogenous miRNAs and enable miRNA functional analysis by up-regulation of miRNA activity. The method disclosed in US20150232810A1 relates specifically to the improvement of reprogramming, since it is said to allow the generation of iPSCs from cell lines that are refractory to methods involving mRNA alone of miRNA alone.

Other works, related to miRNAs and stemness, have focused on the molecular signatures that characterize stemness. Thus, for instance, US patent application published as US20130345289A1 is based on the identification of stem cell specific miRNA signatures that are uniquely expressed in adult stem cells and discloses a method for identifying the presence of clinically utilizable adult stem cells in a biological sample derived from an adult subject by determining the level of a miR gene product in the biological sample, comparing it to the level of a corresponding miR gene product in an anatomically correct control sample and deciding that the subject bears such clinically utilizable adult stem cells when there are differences in the level of specific gee products between samples. One of the possible microRNAs useful as markers for that purpose is hsa-mir-203-precNo1, which is expressed in differentiated cells but not in the stem cell population. From the accession number included in US20130345289A1 for hsa-mir-203-precNo1 and the comparison with the information available in miRbase Database (http://www.mirbase.org/) on 12 Mar. 2017, it can be concluded that it is hsa-miR203a-3p (SEQ ID NO:1, Accession in miRbase MIMAT0000264), the main mature sequence generated by the human hsa-miR-203a gene (SEQ ID NO:2, Accession in miRbase MI0000283). A second mature sequence can be generated from hsa-miR-203a, hsa-miR-203a-5p* (SEQ ID NO:53, Accession in miRbase MIMAT0031890).

Thus, as happens with many other microRNAs, two mature microRNAs can originate from opposite arms of the same pre-miRNA, has-miR-203a, which are denoted with a -3p or -5p suffix. However, the mature microRNA found from one arm of the hairpin is usually much more abundant than that found from the other arm, in which case, an asterisk following the name indicates the mature species found at low levels from the opposite arm of a hairpin. In the case of miR-203, the most abundant mature form is miR-203a-3p, while the low abundant form is called miR-203a-5p*.

Human miR-203 is expressed from chromosome 19. Its murine counterpart, mmu-miR-203 (SEQ ID NO:3, Accession in miRbase MI0000246) is expressed from chromosome 14 of Mus musculus. The main mature sequence of mmu-miR-203, mmu-miR-203-3p (SEQ ID NO:4, Accession in miRbase MIMAT0000236) seems to be identical to that of hsa-miR203a-3p. There are experimental evidences of a second mature sequence, mmu-miR-203-5p* (SEQ ID NO:54, Accession in miRbase MIMAT0004547), which is shorter than hsa-miR-203a-5p (22 nucleotides instead of 25) and differs slightly from its human counterpart in the rest of the sequence (in position 11, G is replaced by A in hsa-miR203a-5p*).

miR-203 is a microRNA with hundreds of potential targets, some of them acting of opposing directions in their corresponding pathways, as can be found using tools such as TargetScan (http://www.targetscan.org) or MiRanda (version of August 2010 downloadable, for instance, from http://www.microrna.org/microrna/getDownloads.do). It was initially identified as a skin-specific microRNA, which forms an expression gradient that defines the boundary between proliferative epidermal basal progenitors and terminally differentiating suprabasal cells, thus limiting stemness potential in the skin (Yi et al., 2008). It has also been found upregulated in psoriasis and differentially expressed in some types of cancer.

Contrary to microRNAs which have been previously associated with cell reprogramming and/or acquisition of ESC features, such as miR-302 and those of clusters of miR-302-367, miR-290-295 or miR-106-363, miR-203 is considered a stemness repressor (Yi et al., 2008; Volinia et al., 2014), although its expression during early development was unknown until yet.

Some reviews on the microRNA regulation of stem cells (Huang et al., 2011) refer to miR-203 as a microRNA that cooperates with miR200c and miR-183 in the modulation of Sox2 and Klf4. Actually, such statement is made referring to a research paper (Wellner et al., 2009) where miR-203 is qualified as a stemness inhibitor, but not as a regulator of Sox2 or Klf4. Specifically, Wellner el al. reported that ZEB1 represses expression of stemness-inhibiting miR-203 and, moreover, that miR-200c, miR-203 and miR-183 cooperate to suppress expression of stem cell factors in cancer cells and mouse embryonic stem (ES) cells, as demonstrated for the polycomb repressor Bmi1.

The role of miR-203 as an inhibitor of stemness of pluripotent cells has been also suggested in connection with epithelial differentiation (Nissan et al., 2011) and, more specifically, in connection with the in vitro differentiation of hESCs into keratinocytes, where it can be seen that induction of miR-203 during epidermal differentiation occurs from the earliest stages but becomes relevant in keratinocyte differentiation after three days of treatment with BMP4, that is: once that hESCs have been already committed to epidermal differentiation. In accordance with such results, miR-203 could be considered a critical factor that prevents stemness of pluripotent cells by inducing epithelial differentiation.

Also in that line, it has been reported (Kapinas et al., 2015) that selective regulation of survivin isoform expression by miR-203 contributes to mechanisms related to pluripotency of human embryonic stem cells, specifically by repressing pluripotency of hESCs. Experiments where hESCs (H9) were transfected with a miR-203 inhibitor showed increased levels of nuclear survivin, while the assays where overexpression of miR-203 was achieved by transfecting hESCs with a miR-203 precursor resulted in a decrease in nuclear survivin levels. As can be read in the mentioned article, such results led to Kapinas et al. to hypothesize that miR-203 may inhibit pluripotency by negatively regulating survivin expression.

In iPSCs, miR-203 has been reported to contribute to a process opposite to stemness and that prevents iPSC function: senescence. And such effect is exerted precisely through the miR-203-survivin-p21 pathway (Xu et al., 2010).

miR-203 has been associated with cancer and has been seen to display tumor suppressive functions in multiple cancers (Bueno et al., 2008; Michel & Malumbres, 2013). The importance of the epigenetic inactivation of miR-203 for the development of leukemias associated to Philadelphia chromosome has been discussed, as well as the possibility of injecting miR-203 as a therapy against said leukemias, since the recovery of miR-203 level prevents the production of the oncogenic protein BCR-ABL and, as a consequence, the proliferation of tumour cells ceases, even in the cases of tumors resistant to other therapeutic approaches. Primary tumors with metastasis show widespread repression of hsa-miR-203a, and the asymmetry hsa-miR-302 (high)/hsa-miR-203a (low) has been found to be associated with stem cell markers, metastasis and shorter survival in invasive ductal carcinoma (Volinia et al., 2014).

miR-203 is also considered one of the microRNAs involved in controlling components of the epigenetic machinery. Works about the potential association between the expression of miR-203, miR-26, and miR-29 family members and the genes Dnmt3a, Dnmt3b, Mecp2, and Ezh2 during cells transformation have shown that said microRNAs and their validated or predicted targets are inversely expressed, indicating that these molecules are involved in epigenetic reprogramming. For instance, it has been reported that miR-203 downregulates Dnmt3b in mouse melanocyte cells (Gasque Schoof et al., 2015).

Unfortunately, and despite all the knowledge acquired about reprogramming and the markers and determinants of stemness and pluripotency, many questions regarding the differentiation outcome of pluripotent cells and how those decisions might be taken remain unsolved. Although researchers have begun to identify the numerous molecular pathways that are implicated in reprogramming somatic cells, much more basic research will be required to identify the full spectrum of events that enable this process. The details of the reprogramming process and its kinetics, an in particular the epigenetic reprogramming, remain incompletely understood.

Finally, whereas most strategies have been designed to improve the efficiency of reprogramming, very few applications are aimed to improve the differentiation potential of already-established pluripotent cells. Maintaining a full differentiation potential along with self-renewal ability is a major property of stem cells during development and regeneration, but available ESCs or iPSCs obtained after reprogramming process are often not of a quality that facilitates the subsequent differentiation process. The low quality of iPSCs and the differences in quality among iPSCs resulting form the same reprogramming process is particularly important for their use in human regenerative therapies. iPSCs are considered by many authors a subset of pluripotent stem cells that is influenced by the somatic cell of origin and cell culture conditions, which subset shows differences even among the iPSCs obtained in the course of the same reprogramming process. Many iPSCs show a reduced differentiation capability, that could be explained by an incomplete genomic reprogramming, which gives rise to iPSCs that are closer to the primed state than to the naïve state. Honda and coworkers (Honda et al., 2013) reported that the limited differentiation capacity of iPSCs could be improved by continuous passage and its conversion into a more immature, naïve-like state. The conversion into such naïve-like state requires the expression of OCT3/4 from a lentivirus, the passage of iPSCs to mouse embryonic fibroblasts and the culture in a medium including CHIR99021 (a GSK-inhibitor) and leukemia inhibitory factor. Such cells showed an improved capability of differentiation into mature oligodendrocytes, which suggest that the naïve-like conversion of iPSCs endow them with a higher differentiation capacity.

Maintenance of pluripotent cells in vitro into the naïve state (either ESCs or iPSCs), is challenging and has been also object of a number of studies, most of them focusing on the addition of different compounds to the culture media with the aim of achieving the maintenance of the broadest possible pluripotency potency. Mouse ESCs can be maintained long term in the naïve state when cultured in the presence of serum plus leukemia inhibitory factor (LIF) (Niwa et al., 2009). To note, LIF alone is in many cases unable to prevent differentiation of mESCs and is even more unefficient with iPSCs. This limitation is partially overcome by the addition of two small molecule kinase inhibitors termed "2i" with LIF. The 2i components include a specific inhibitor of extracellular signal-regulated kinase (ERK1/2)/mitogen-activated protein kinase (MAPK) signal transduction pathway (MEKi, PD0325901) and a specific inhibitor of glycogen synthase kinase 3 beta (GSK3βi, CHIR99021) that can protect pluripotent cells from pro-differentiation stimuli and select against differentiating cells (Ying et al., 2008). International Application WO2012087965 discloses a similar method to maintain or increase the potency of cells wherein pluripotent cells are cultured in a feeder-free environment where at least one small molecule is present which is selected from inhibitors of TGF-β, GSK3, MEK or ROCK, which method achieves mainly an increase in the viability and an increase in potency, which increase in the potency is characterized by one or more of the following features: a) expression of at least one pluripotent stem cell marker selected from the group consisting of endogenous Oct4, Nanog, SSEA4, Sox2, Klf4, Tra181, and Lin28; b) pluripotent stem cell morphology; c) ability to contribute to germline transmission; d) teratoma formation; e) ability to differentiate or transdifferentiate into a lineage different from the starting lineage; and f) in vitro trilineage differentiation, which can be considered markers of naïve status of pluripotent stem cells.

Other research groups have focused on modifications of the culture media of iPS cells in order to improve the efficiency of differentiation into specific lineages and/or select cells that are more appropriate for the desired differentiation process. Most of them are based on the addition of compounds such as those mentioned above. Thus, for instance, WO2014201254A1 discloses methods involving microRNAs for deriving cardiomyocytes from iPSCs or ESCs, wherein microRNAs of the let-7 family are described as important microRNAs for in vitro cardiac maturation. EP249071A2 discloses methods and compositions for the production of cardiomyocytes from pluripotent stem cells wherein the pluripotent cells are differentiated into cardiomyocytes in the presence of ROCK inhibitors. WO2014200030A1 discloses a method for obtaining hematopoietic stem cells and/or hematopoietic precursor cells from pluripotent stem cells which comprises culturing the pluripotent stem cells in the presence of IGF2 and the selection of induced pluripotent stem cells having a high capacity for differentiating into hematopoietic stemcells on the basis of the level of expression of one or more genes. EP2646543A1 discloses a method of generating corneal cells wherein human pluripotent stem cells are cultured in corneal fibroblast-conditioned medium on a solid surface comprising an extracellular matrix component. KR2017011676A discloses methods for differentiating stem cells to hepatocytes using a culture composition comprising a bio-compatibility solubilization scaffold extract derived from the decellularized organ tissue. WO2017062374 discloses compositions and methods for generating oligodendrocyte precursors from pluripotent stem cells using a three-dimensional culture system comprising a biocompatible polymer and a combination of at least two factors that promote differentiation into oligodendrocytes selected from an agonist of the Sonic hedgehog signaling pathway, a wnt signaling pathway agonist, retinoic acid and a dual-Smad inhibitor.

Some group has reported having achieved improvements in pluripotent stem cell differentiation into multiple lineages adding a single molecule to the culture medium. Chetty et al., in 2013, described improvements in the competency for directed differentiation into multiple lineages in more than 25 stem cell lines after culturing pluripotent stem cells in dimethylsulfoxide (DMSO), increasing the proportion of cells in the early G1 phase of the cell cycle and, consequently, improving competency for directed differentiation and even promoting terminal differentiation into functional derivatives. Nevertheless, none of those strategies properly achieve the naïve state of the obtained pluripotent cells, since the stemness capacity of those cells is never demonstrated (none of the features described above characteristic of naïve cells are examined in those cases), the differentiation improvements are not substantial and in general the former studies lack stringent pluripotency assays such as 4n complementation or chimeras contribution.

Thus, despite of the recent improvements in culturing pluripotent cells in vitro by adding new small molecules (such as LIF, 2i, bFGF, TGFβ, JNKi, p38i, ROCKi, Activin A) and/or sustained expression of transcription factors (such as KLF4, KLF2, OCT4, SOX2, NANOG), improving the differentiation potential of pluripotent cells remains to be an unsolved issue and an important goal to achieve, either during the reprogramming protocol or once pluripotent cells are established. Before cultured pluripotent cells can be considered for use as a clinical tool, their efficiency in generating differentiated cells must improve substantially: clinical application of pluripotent cells will require safe and highly efficient generation of stem cells that can differentiate into diverse cell types with a potential to generate replacement cells in the quest to repair diseases tissues. The improvement of the quality of pluripotent cells is also important for becoming a useful research tool to analyze the mechanisms that regulate cell-fate decisions, or to develop disease models to explore how various human diseases originate as a result of specific mutations and epimutations and, with that information, to develop new drugs to cure or even prevent such diseases.

Although the method of improving differentiation potential based on the addition of DMSO means a promising approach, alternative methods should preferably be developed.

Thus, there is a need of a method that improves the quality of pluripotent cells, particularly iPSCs, by increasing their stemness properties and/or differentiation potential into different cells types. Preferably, the method should be easy to perform, not requiring complicate devices or very expensive products and, if possible, it should be feasible to put it into practice with molecules as safe as possible.

The present invention provides a solution to such problem.

SUMMARY OF THE INVENTION

The present invention is based in the surprising finding, disclosed in the present application, that transient expression or increase of the levels of a single microRNA, microRNA-203, can improve the function of either iPSCs or ESCs in several assays. The effect of a transient exposure to miR-203 is two-fold. First, increased levels of miR-203 in iPSCs induce a transcriptional profile closer to ES cells (a naïve or naïve-like state) including upregulation of the stemness signature. This increase in stemness properties is also observed when using a reported of the 2C-like stage, characteristic of totipotent cells in 2-cell embryos. Second, transient expression or increased of levels of miR-203 in pluripotent cells results in enhanced differentiation in vitro and in vivo to multiple lineages, including the three embryonic layers, as shown in the embryoid bodies generated in vitro or in teratomas and embryo-like structures observed after the injection of these cells in mice. Exposure to miR-203 improved the generation of unusual differentiated tissues, such as pancreas, bone marrow or trophoblast, even although these structures were formed many weeks after the transient exposure to miR-203 in pluripotent cells. Specific differentiation into cardiomyocytes suggests that miR-203 exposure not only favors differentiation but also maturation and functionality in the resulting cells.

Thus, the present invention, in a first aspect, refers to a method for enhancing stemness and/or differentiation potential of pluripotent cells, which comprises a step wherein the cells are exposed to increased levels of microRNA-203 or an analogue thereof. Preferably, the pluripotent cells are induced pluripotent stem cells (iPSCs) in culture, but they can also be embryonic stem cells (ESCs) in culture. Also preferably, the cells are exposed to the increased levels of microRNA-203, or an analogue thereof, transiently, for instance, during 3-5 days. The increase in the levels of microRNA-203 to which the cells are exposed can be achieved by transducing or transforming the cells with an expression vector which expresses microRNA-203 (and inducing such expression, if the expression is inducible), or by adding microRNA-203 or an analogue thereof to the culture medium of the iPSC, if they are in culture. Among the possible analogues, small RNA molecules with at least a fragment with a high degree of homology with the sequence of the mature form of microRNA-203 (SEQ ID NO:1) and, preferably, with chemical modifications, are preferred possible embodiments, including among the analogues double stranded RNA mimics. Said method of the invention is compatible with having obtained the iPSCs by any method, such as, for instance, the original Yamanaka method (contacting somatic differentiated cells, preferably fibroblasts, with a nuclear reprogramming factor comprising a gene product of each one of the following families: Oct family, Klf family, Myc family and Sox family) or variations thereof.

As indicated above, it is a preferred embodiment of the method of the present invention, compatible with all other embodiments, that the cells that are exposed to increased levels of microRNA-203 or an analogue thereof are exposed to at least the mature form of miR-203 which originates from the 3' arm or an analogue thereof. Such mature form can be the miR-203 mature form of any mammal species. As the pluripotent cells that are exposed to increased levels of miR-203 are preferably of human or mouse origin, exposure to at least hsa-miR-203a-3p (SEQ ID NO:1) or mmu-miR-203-3p (SEQ ID NO:4) or an analogue thereof is preferred, which can be alone or in combination with other forms of miR-203, including combinations of analogues of hsa-miR-203a-3p, and/or mmu-miR-203-3p, mature forms of miR-203 originating from the 5' arm (such as hsa-miR-203a-5p* and/or mmu-miR-203-5p*) or analogues thereof. The cells can be exposed to said mature forms even when the added molecule is the pre-miRNA of miR-203 or an analogue thereof, due to the processing of said pre-miRNA in the cells, As commented before, miR-203 is expressed in vivo as a pre-miRNA (which is represented by SEQ ID NO.2 in the case of the human molecule and by SEQ ID NO:3 in the case of the mouse molecule), which pre-miRNA can give rise to two different mature forms, one originating from the 5' arm of the pre-miRNA and the other one from the 3' arm. The mature form originating from the 3' arm is the most abundant and, according to one of the assays of Example 1, is the form which is responsible, to a higher degree, of the effects of the present invention, at least those related to embryo-body formation. As can be seen in FIG. 10, the sequence of miR-203 is highly conserved among different mammalian species, particularly the seed regions related to Dnmt3a and Dnmt3b. Thus, for the purposes of the present invention, unless it is specified the reference to a particular species or to a particular form of the microRNA, the term "miR-203" or "microRNA-203" encompasses the microRNA-203 expressed by any mammal and any of its possible forms, that is: the pre-miRNA and/or the mature forms originating either from the 5' arm (represented by SEQ ID NO:53 in the case of the human molecule, hsa-miR-203a-5p, and by SEQ ID NO:54 in the case of the mouse molecule) or from the 3' arm (represented by SEQ ID NO:1 and SEQ ID NO:4, which are identical, either for the human molecule, hsa-miR-203a-3p, or for the mouse molecule, mmu-miR-203-3p). The combination of two or more of said forms of miR-203, and very specially the combination of the two mature forms originating from the 5' arm and from the 3' arm, as in most of the Examples of the present application, is also encompassed by the term "miR-203" or "microRNA-203". The term "an analogue of miR-203" or, when the antecedents justify it, "an analogue thereof", is envisioned to encompass one molecule or a mixture of molecules, each of them being an analogue of any of the molecules encompassed by term "microRNA-203" or "miR-203"; preferably, the molecule or at least one of the molecules of the mixture will be an analogue or mimic, as defined hereinafter, of one mature form originating from the 3' arm of a pre-miRNA-203; most preferably, the molecule or at least one of the mixture of molecules defined by the term "analogue" will be an analogue of hsa-miR-203a-3p (SEQ ID NO:1) or mmu-miR-203-3p (SEQ ID NO:4).

Another possible aspect of the invention are the pluripotent cells that are obtained after having carried out the method of the invention, particularly after transient exposure to an increased level of miR-203, which are different from the reprogrammed iPSCs that are used as starting material. When such naïve pluripotent cells are subjected to differentiation protocols (both in vitro and in vivo), they exhibit an expanded cell fate potential, generating cells characterized by Nanog, Oct and Sox2 expression (well-established markers of pluripotency), although cells expressing Nestin, Gata4 or Cd34 (well-established markers of differentiation) appear to co-exist with them in the same culture population. It is important also to point out that they show signs of being naïve-like cells, such as the characteristic cell morphology of naïve cells, the capability of contributing to chimeras and germ line transmission.

The naïve pluripotent cells resultant from the method of the invention show an improved differentiation and maturation outcome, which can be observed particularly, when differentiated specifically to cardiomyocytes. Taking this into account, another aspect of the invention is the use of said cells of the invention for obtaining differentiated cells such as cardiomyocytes. Other possible embodiments are: cells of the nervous system (neurons and glial cells, for instance), chondrocytes, or pancreatic beta cells.

Therefore, the method of the invention can be considered a strategy for obtaining naïve pluripotent cells with improved stemness capacity and expanded differentiation potential as well as differentiated and/or mature cells. The differentiated or mature cells obtained by the method of the present invention are also comprised within the scope of the invention.

Representative images of EBs derived from wild-type ESCs transfected with control mimics, miR-203a-3p or miR-203a-5p mimics, at different time points during the differentiation process. Scale bars, 500 µm.

Figure 6:
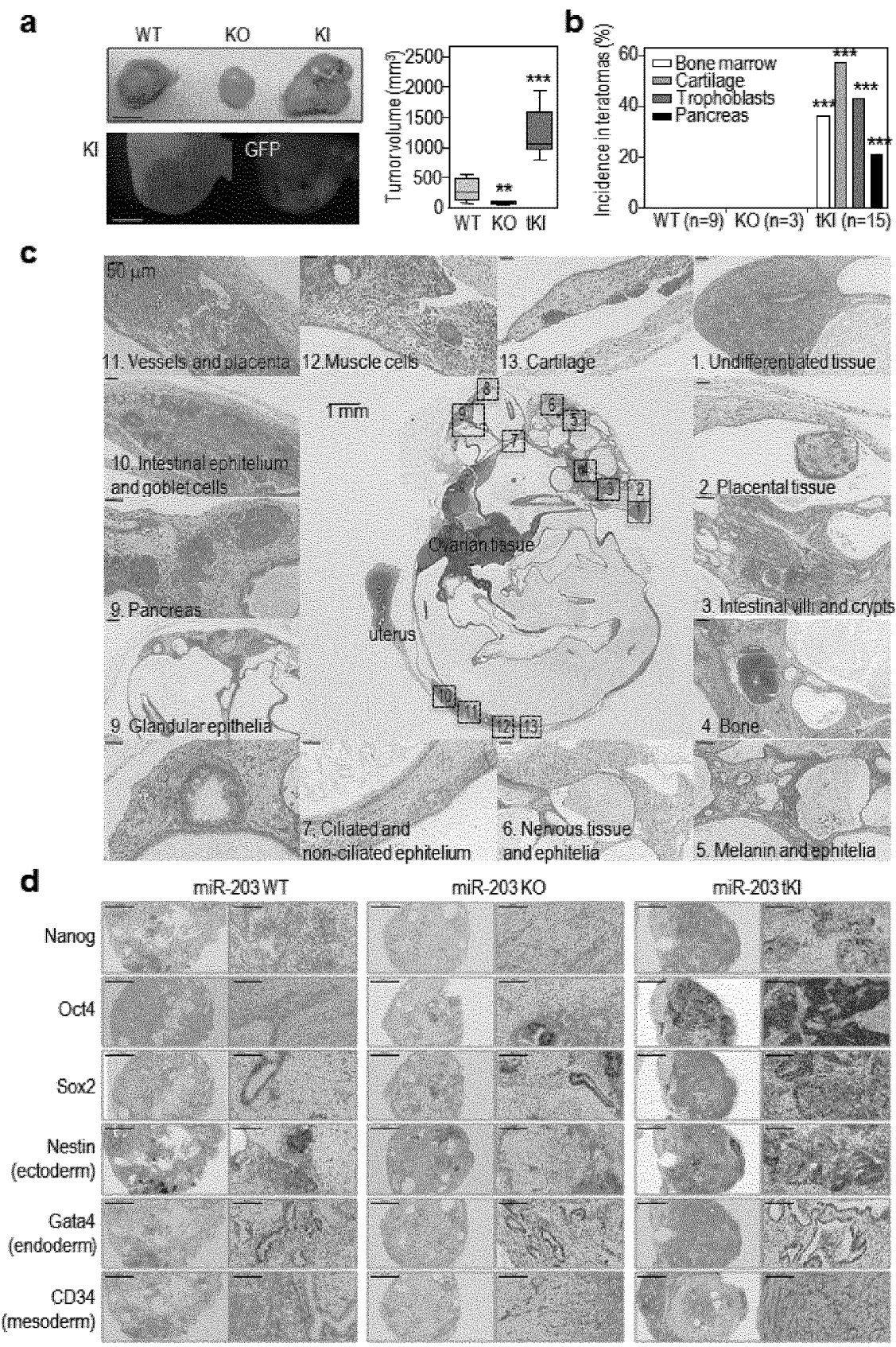

FIG. 6. Transient exposure of iPSCs to miR-203 results in complex teratomas in vivo. a, Representative images of teratomas generated 20-25 days after subcutaneous injection of WT, KO and tKI (expressing GFP) iPSCs. Scale bar, 5 mm. Bottom pictures show an example of a tKI iPSC-derived embryo-like structure, expressing GFP. Scale bar, 1 mm. Right plot shows tumor volume ($mm^3$) measured at the end of the experiment. Data are represented as mean±s.e.m. (n=8 tumors per genotype). b, Incidence of specific highly differentiated tissues in teratomas. The number of tumors included in the analysis is indicated in the panel. c, Representative example of a highly differentiated teratoma generated from tKI iPSCs after i.p. injection in nude mice. Most of these complex teratomas were detected in the proximity of the uterus or as ovarian cysts in the host mice. The panel shows higher magnifications (H&E staining) of several differentiated tissues and cells observed in the teratoma. Scale bars, 1 mm (central image) or 50 µm (insets). d, Immunohistochemical detection of pluripotency markers (Nanog, Oct4, Sox2), and markers of differentiation to the three germ layers (Nestin, Gata4, CD34) in teratomas derived from WT, KO and tKI iPSCs. Scale bars, 2000 µm and 100 µm for higher magnifications. In a and b, P<0.01; *P<0.001 (Student's t-test).

Figure 7:
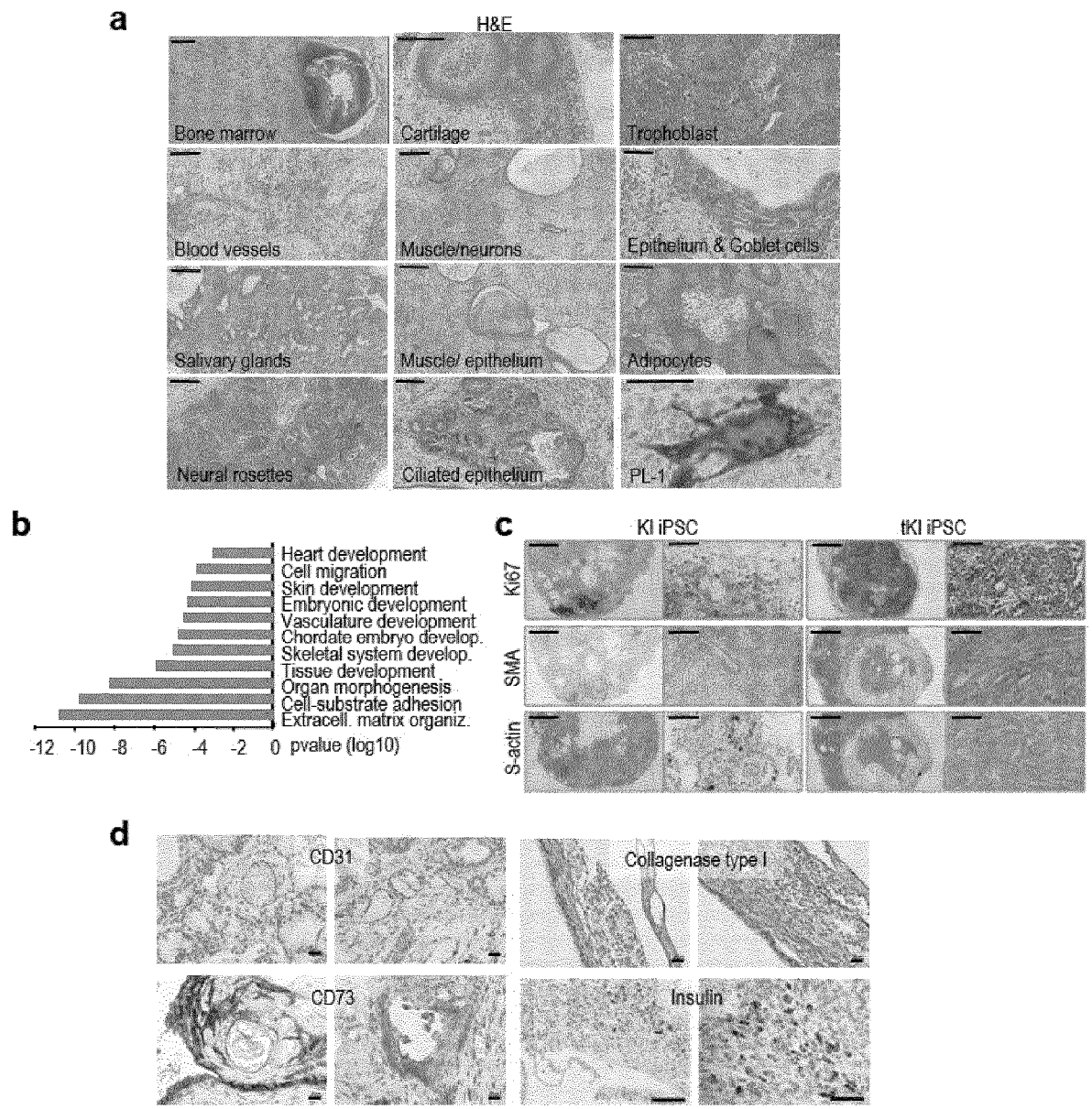

FIG. 7. Differentiation properties in teratomas generated from miR-203 tKI iPSCs. a, Histopathological examples (H&E staining) of specific tissues found in tKI iPSCs-derived teratomas. Scale bars, 100 µm. A magnification of trophoblasts stained with Placental Lactogen-1 (PL-1) is also shown (scale bar, 50 µm). b, Gene Ontology Analysis of genes significantly altered in miR-203 tKI-derived teratomas compared to wild-type teratomas. c, Immunohistochemical analysis of teratomas derived from wild-type, KO or tKI iPSCs. Antibodies against the proliferation marker Ki67 or terminal differentiation to smooth muscle or skeletal muscle markers (actin) were used. Scale bars, 2000 µm and 100 µm for higher magnifications. d, immunodetection of CD31 (bone marrow), CD73 (pancreas), collagenase type I (cartilage) and insulin (in-producing cells) in teratomas generated from tKI iPSCs. Scale bars, 20 µm.

Figure 8:
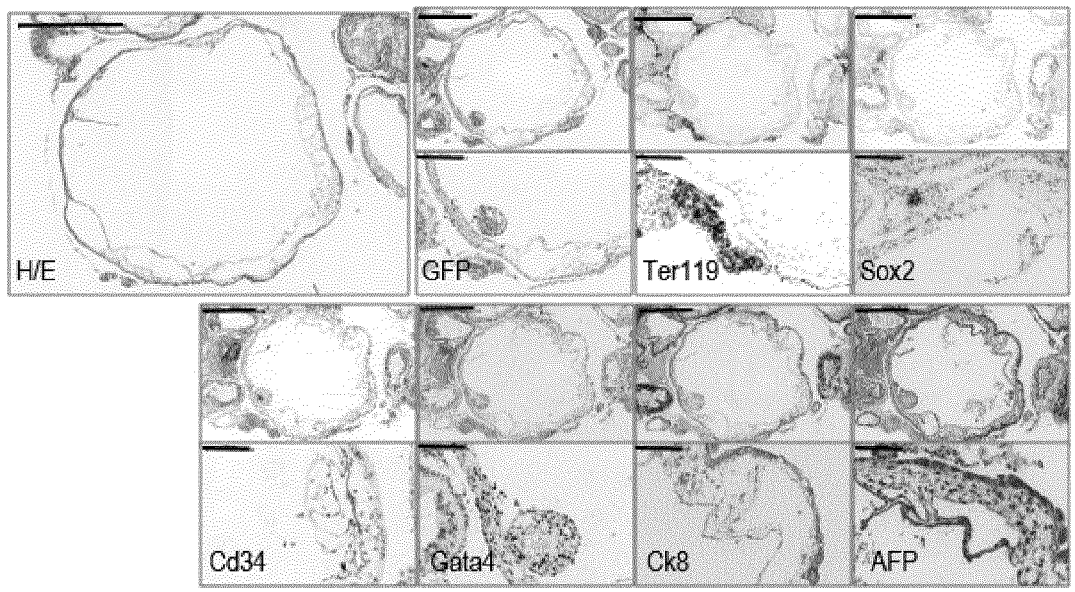
Figure 8:
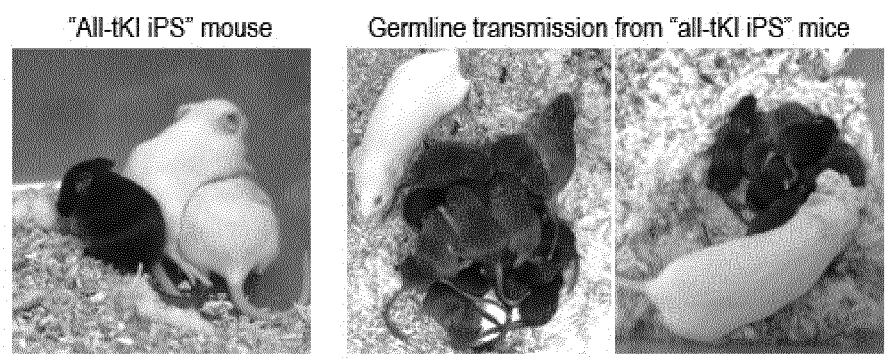

FIG. 8. Transient exposure to miR-203 in vitro results in embryo-like structures in host mice similar to those induced by iPSCs generated in vivo. a, Representative example of E-Ls generated after i.p. injection of tKI GFP-expressing iPSCs. H&E, hematoxylin and eosin. The following antigens were detected by immunohistochemistry: GFP, Sox2 (ectoderm), Cd34 (mesoderm), Gata4 (endoderm), AFP and CK8 (visceral endoderm of the yolk sac) and Ter119 (nucleated erythroid cells). Scale bars, 500 µm and 100 µm for higher magnifications. b, Photograph of a representative example of a viable all-iPSC mouse (black) generated from tKI iPSCs in the embryo tetraploid complementation assays.

Figure 9:
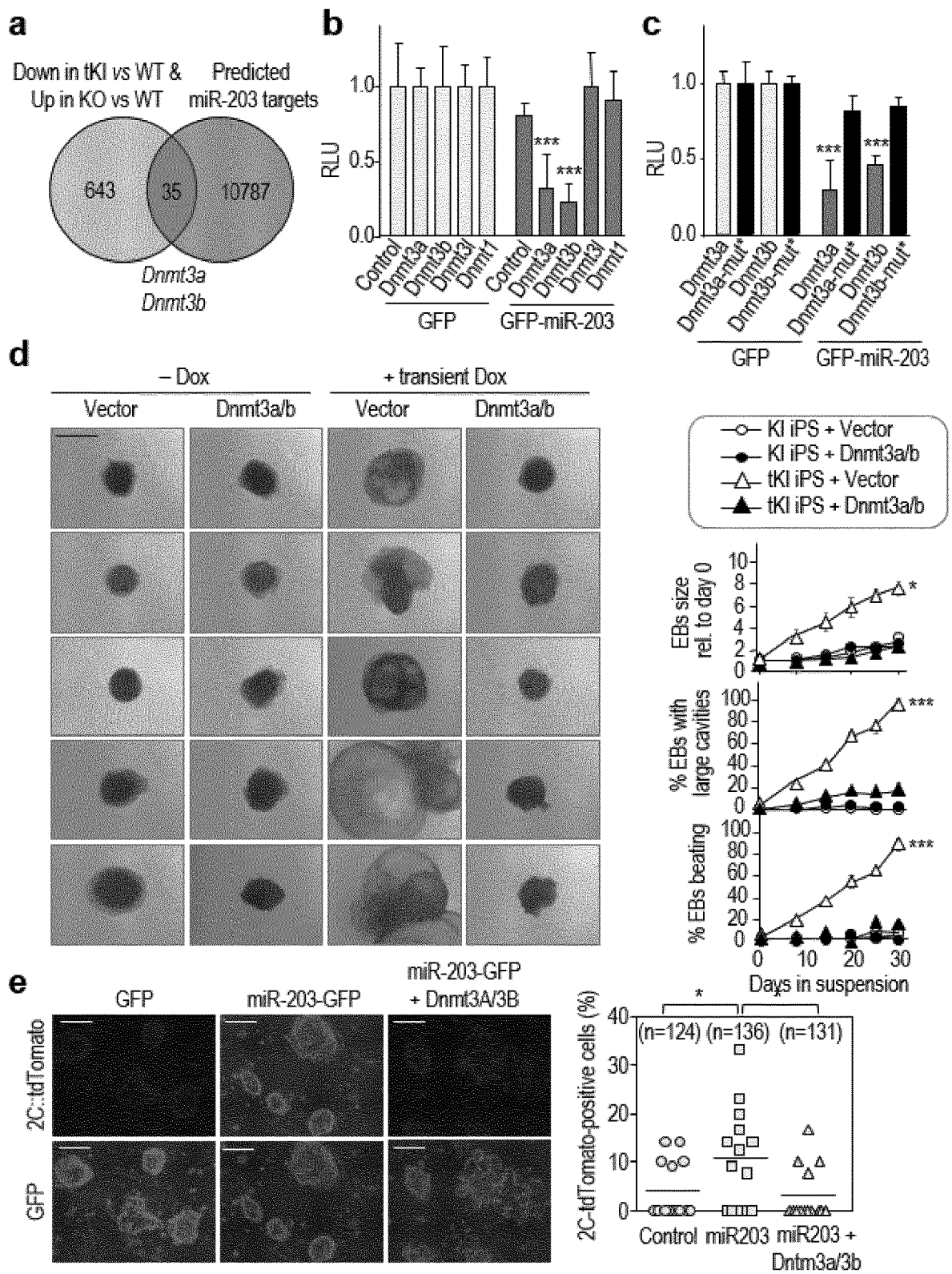
Figure 9:
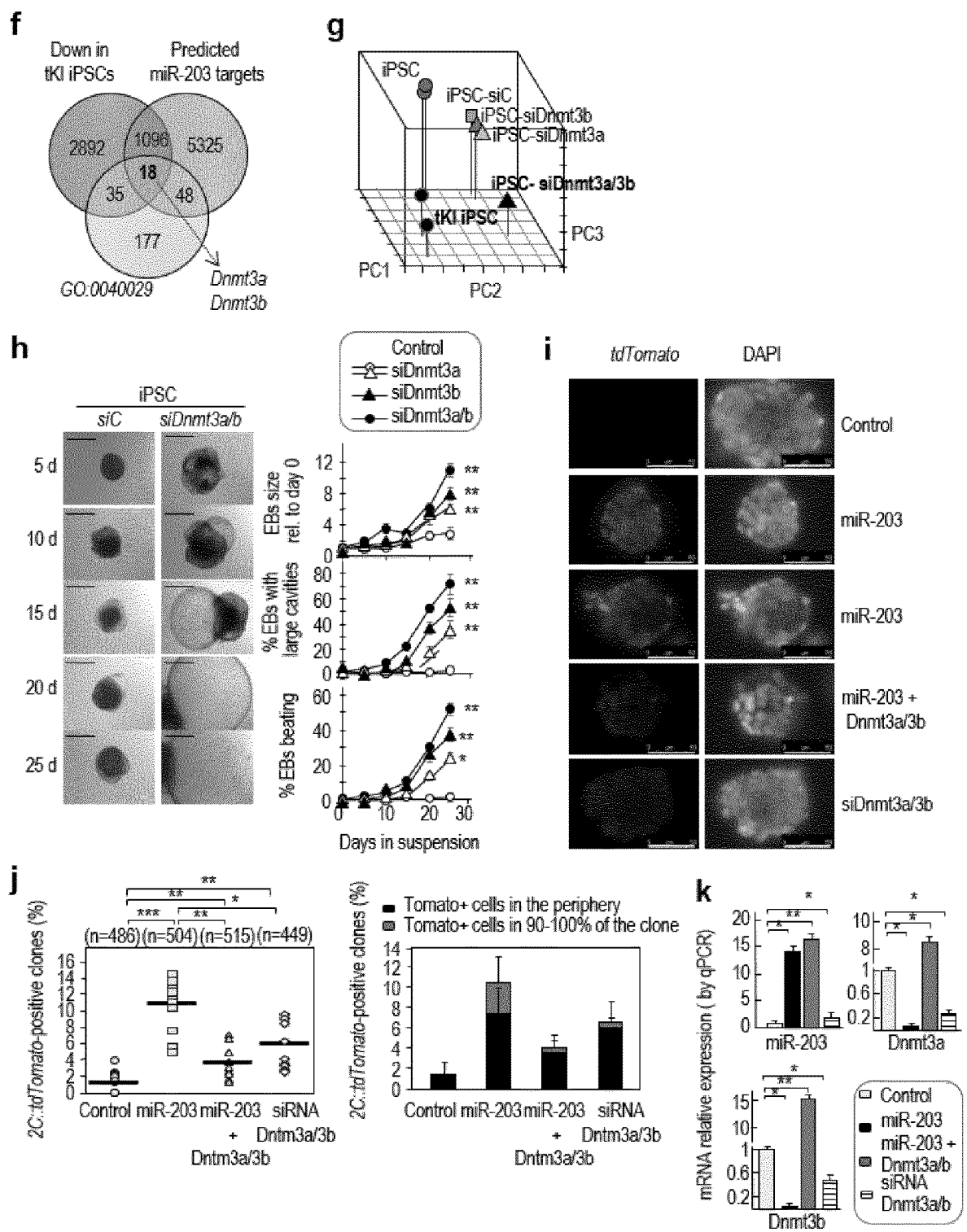

FIG. 9. DNA methyltransferases 3a and 3b are miR-203 targets involved in the control of pluripotency and differentiation. a, Venn Diagrams representing the common genes down-regulated in tKI vs. WT iPSCs, up-regulated in KO vs. WT iPSCs, and predicted as miR-203 targets (show Table 6 for a list of the common 35 transcripts (including Dnmt3a and Dnmt3b). b,c, Relative Luciferase Units (RLU; normalized to Renilla luciferase and relative to DNA amount) in 293T cells transfected with DNA constructs carrying the wild-type 3'UTRs from the indicated transcripts (b) or the mutated versions of Dnmt3a and Dnmt3b 3'UTRs, downstream of the luciferase reporter (c). Cells were co-transfected with Renilla luciferase as a control of transfection, and a plasmid expressing GFP or miR-203-GFP. Data are represented as mean±s.d. (n=3 independent experiments). d, Representative images of embryoid bodies (EBs) derived from tKI iPSCs that were transiently and simultaneously transduced with Dnmt3a and Dnmt3b cDNAs or empty vectors, and treated with vehicle or Dox as indicated. Scale bars, 500 µm. Histograms show the quantification of EBs with long cavities, beating EBs and EB size at different time points. e, Immunodetection of GFP or tdTomato in ESCs stably expressing the 2C::tdTomato reporter, and transiently transduced with either pMCSV-GFP, pMCSV-miR-203-GFP or pMCSV-miR-203-GFP+Dnmt3a/b cDNAs. Scale bar, 16 µm. The plot shows the percentage of Tomato-positive cells out of the total GFP-positive cells. Data are represented as mean±s.e.m (n=3 independent experiments). f, Venn Diagrams representing common genes down-regulated in tKI iPSCs, predicted as miR-203 targets and also involved in the epigenetic regulation of gene transcription (GO:0040029). g, Principal Component Analysis from RNAseq data including profiles from wild-type iPSCs, tKI iPSCs, and wild-type iPSCs transfected with either control siRNAs (siC), or siRNAs specific against Dnmt3a (siDnmt3a), Dnmt3b (siDnmt3b) or both (siDnmt3a/b). h, Representative images of embryoid bodies (EBs) derived from wild-type iPSCs in which the expression of Dnmt3a and Dnmt3b was transiently repressed by siRNAs. Scale bars, 500 µm. Histograms show the quantification of the size of EBs and the percentage of EBs with large cavities or beating at different time points during the differentiation process. i, Detection of tdTomato and DAPI in ESCs stably expressing the 2C::tdTomato reporter, and transiently transfected with either control mimics, miR-203 mimics, miR-203 mimics+Dnmt3a and Dnmt3b cDNAs or siRNA against both Dnmt3a and Dnmt3b transcripts. Scale bar, 50 µm. j, The left histogram shows the percentage of Tomato-positive cells in the assays in panel i) five days after transfection. The right histogram shows the percentage of Tomato-positive colonies in which Tomato is expressed only in the periphery of the clone (black) or in the majority of the cells constituting the colony (grey). Data are mean±s.e.m. (n=3 independent experiments; 486 colonies for control mimics, 504 colonies for miR-203 mimics, 515 colonies for miR-203 mimics+Dnmt3a/3b cDNA and 449 colonies for Dnmt3a/3b siRNAs). k, miR-203, Dnmt3a and Dnmt3b transcript expression in wild-type iPSCs transiently transfected as indicated in (i). RNA expression was measured 24 hours after the transfection protocols and was normalized by a control miRNA (miR-142) or GAPDH mRNA, respectively. In b-e, h, j, k, *P<0.05; P<0.01; *P<0.001 (Student's t-test).

Figure 10:
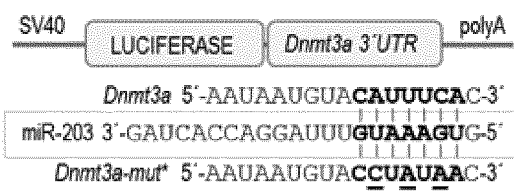
Figure 10:
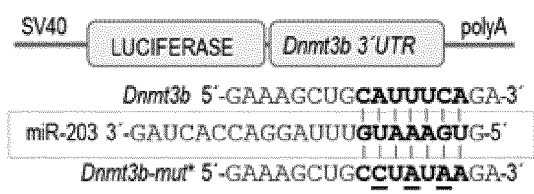

FIG. 10. Alignment between miR-203 and Dnmta/b 3'-UTR sequences. a, Dnmt3a and Dnmt3b 3'UTR alignment in several representative species (Hsa: *Homo sapiens*; Mmu: *Mus musculus*; Rno: *Rattus norvegicus*; Ocu: *Oryctolagus cuniculus*; Ptr: *Pan troglodytes* (chimpanzee); Mml: *Macaca mulatta*; Oga: *Otolemur garnetti*; Tbe: *Tupaia belangeri*; Eeu: *Erinaceus europaeus*; Cfa: *Canis familiaris* (dog); Eca: *Equus caballus*; Bta: *Bos taurus* (cow); Ete: *Echinops telfairi*; Fca: *Felis catus* (domestic cat). The seed region of the miR-203 target site contained in these 3'-UTRs is highlighted in bold font and aligned with the corresponding miR-203 seed sequence. b, Schematic representation of the luciferase reporter, carrying the wild-type Dnmt3a (left) or Dnmt3b (right) complete 3'-UTRs or the corresponding mutated versions, downstream of the luciferase gene. The mutated residues are shown underlined.

Figure 11:
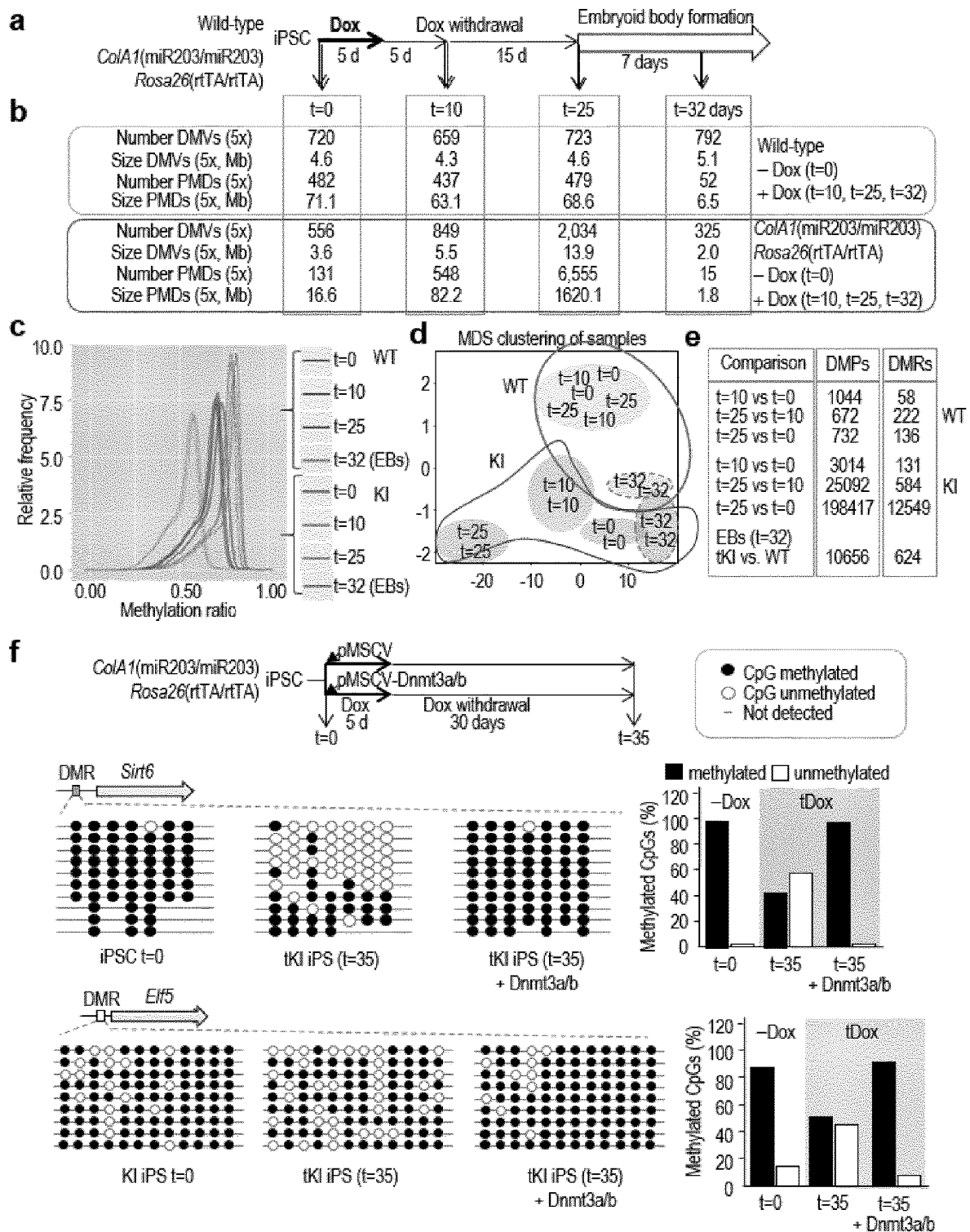

FIG. 11. Transient expression of miR-203 induces genome-wide hypomethylation in iPSCs. a, Experimental design for the genome-wide DNA methylation analysis of WT and tKI iPSC and embryoid bodies (EBs) derived from them. Cells (two independent tKI clones and two WT technical replicates) were transiently treated with Dox for 5 days and then subjected to Dox withdrawal for 20 additional days before starting the EB formation protocol. Samples for DNA and RNA analysis were collected at the indicated time points before Dox (t=0), 5 days after Dox withdrawal (t=10), 20 days after Dox withdrawal (t=25) or 7 days after starting the EB generation protocol (t=32 days). b, Genome-wide DNA methylation data showing the number and size of DNA methylation valleys (DMVs) and partially methylated domains (PMDs). c, DNA methylation distribution of the indicated samples, smoothed over 100 kb-blocks. d, Principal Component Analysis showing the distribution of the different methylation profiles in the indicated samples (wt and tKI samples are grouped separately for clarify). e, Number of differentially methylated single CpG sites (DMPs) and differentially methylated regions (DMRs) in the indicated comparisons. f, Experimental protocol followed to test DNA methylation rescue by miR-203-resistant Dnmt3a/b cDNAs. Specific differentially methylated regions (DMRs) at the Sirt6 and Elf5 loci were analyzed by PCR amplification and sequencing of bisulphite-modified DNA. The quantification of methylated vs. unmethylated CpGs is shown in the histogram.

Figure 12:
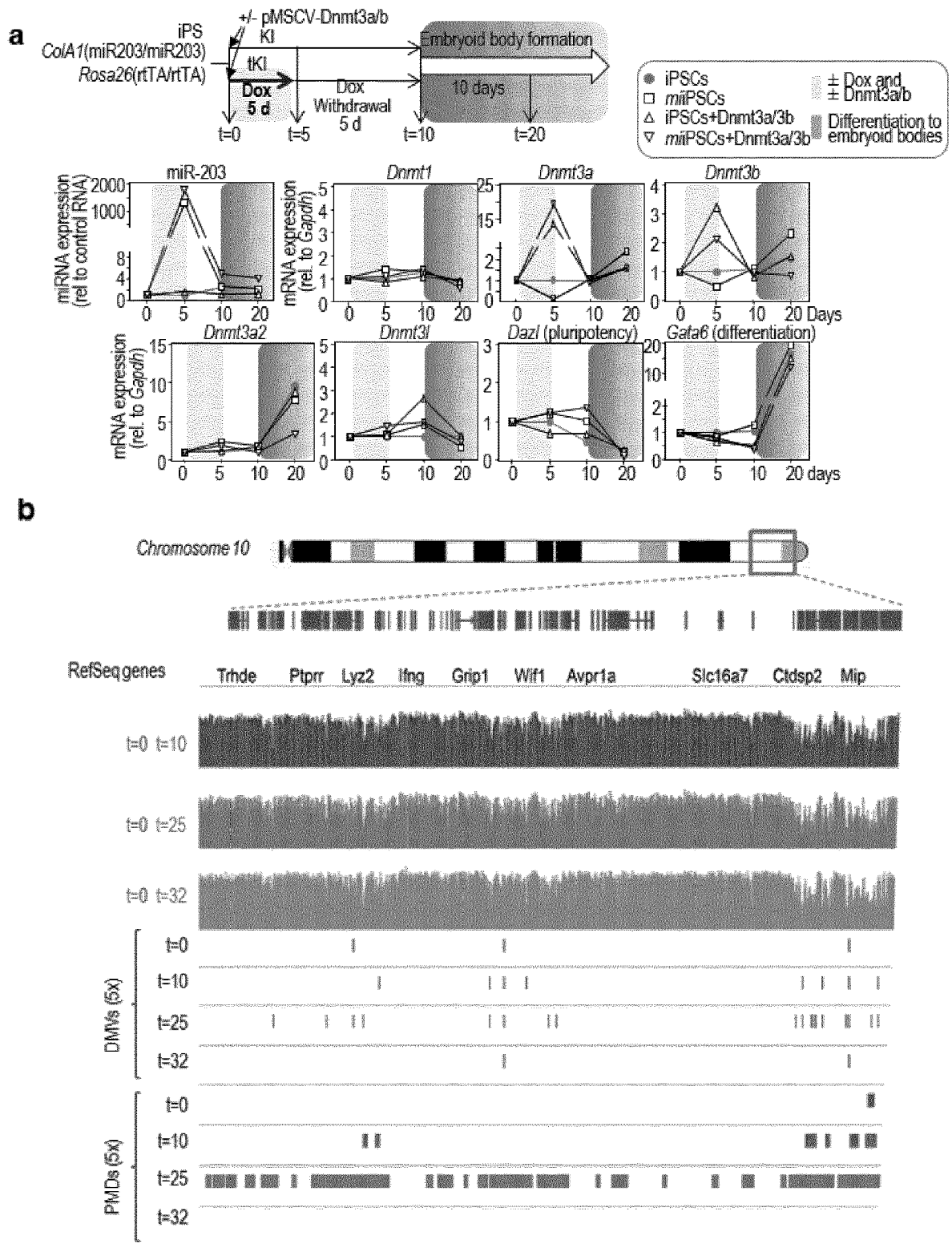

FIG. 12. Genome-wide methylation of iPSCs or embryoid bodies after transient exposure to miR-203. a, Expression levels, as determined by quantitative PCR, of miR-203, and transcripts for the DNA methyltransferases Dnmt1, Dnmt3a, Dnmt3b, Dnmt3a2 and Dnmt3l, or pluripotency (Dazl) and differentiation (Gata6) markers. KI iPSCs treated or not with doxycycline (Dox) and simultaneously transduced with Dnmt3a/b cDNAs or empty vector were used as shown in the schematic representation of the experimental design. The first shadow beginning from the left (light gray, pink in the original) indicates the time-lapse in which the cells were treated or not with Dox and transduced or not with Dnmt3a/b cDNAs. The second shadow from the left (dark gray, orange in the original) indicates the differentiation process to embryoid bodies. Data are represented as mean of three technical replicates per experiment (n=2 independent experiments). b, Representative genomic region (telomeric to chromosome 10) showing the methylation pattern in tKI iPSCs and embryoid bodies. Times refer to FIG. 11a. DMV, DNA methylation valley; PMD, partially methylated domain.

Figure 13:
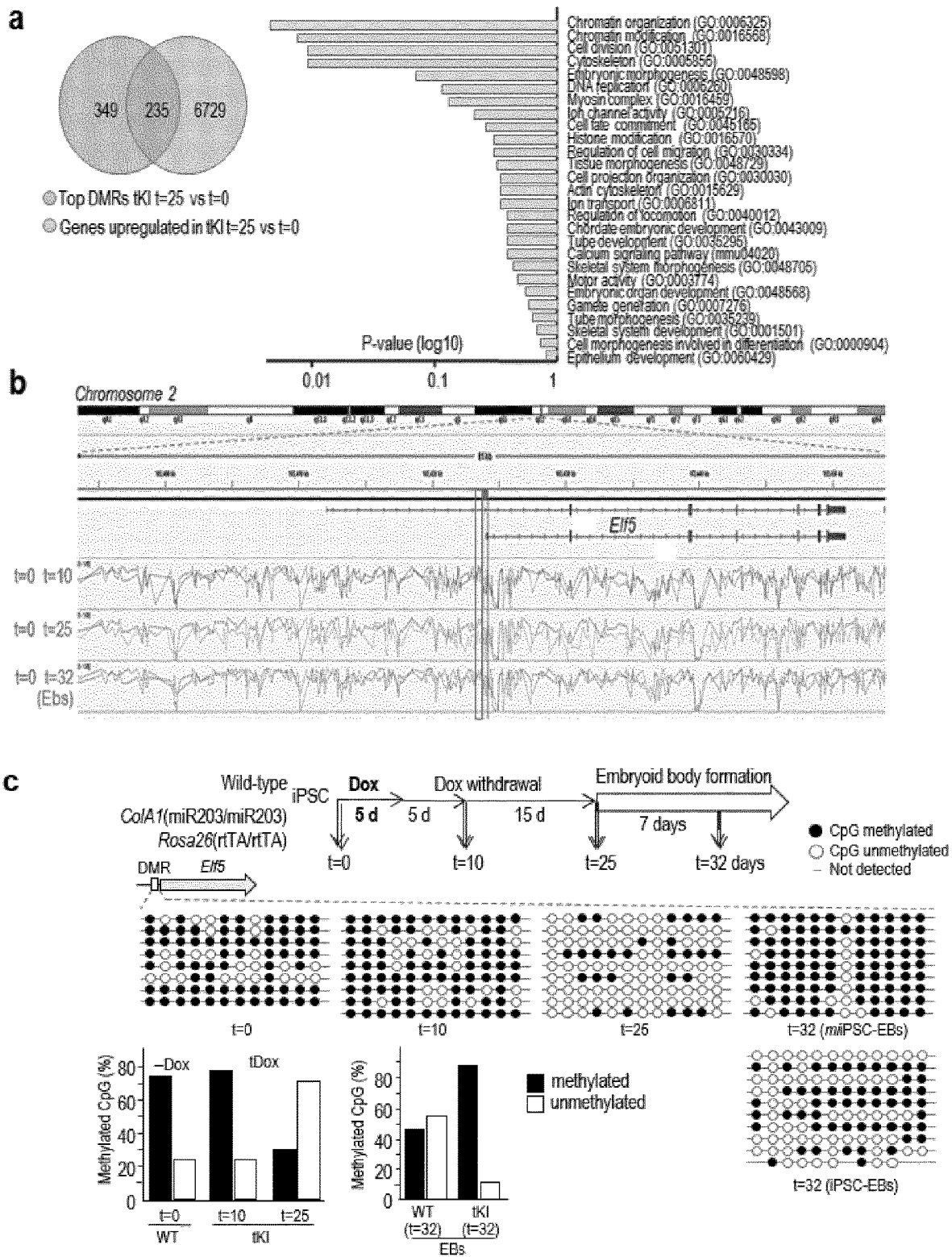

FIG. 13. Genome-wide methylation and gene expression changes in iPSCs or embryoid bodies. a, Venn Diagrams representing the common genes up-regulated (data from RNA seq studies) and hypomethylated (data from genome-wide methylation studies) in tKI iPSCs 20 days after Dox withdrawal. A total of 235 genes were both DNA-hypomethylated and upregulated in such conditions. Gene Ontology Analysis of this list is presented in the right panel. b, Methylation data in the Elf5 genomic region in KI iPSCs before induction (t=0, upper line), 10 or 25 days after transient miR-203 induction (lower signals) and in embyoid bodies (EB, t=32), following the experimental design shown in FIG. 11a. Two Elf5 transcripts are shown. c, Experimental design used for the validation of methylation data in the indicated Elf5 differentially methylated region (DMR; box in b and first part of the arrow representing Elf5 in c). DNA was isolated as indicated and sequenced after bisulfite modification. Eight to ten independent clones were sequenced per condition. Histograms show the percentage of DNA methylation at the Elf5 DMR in the different conditions.

Figure 14:
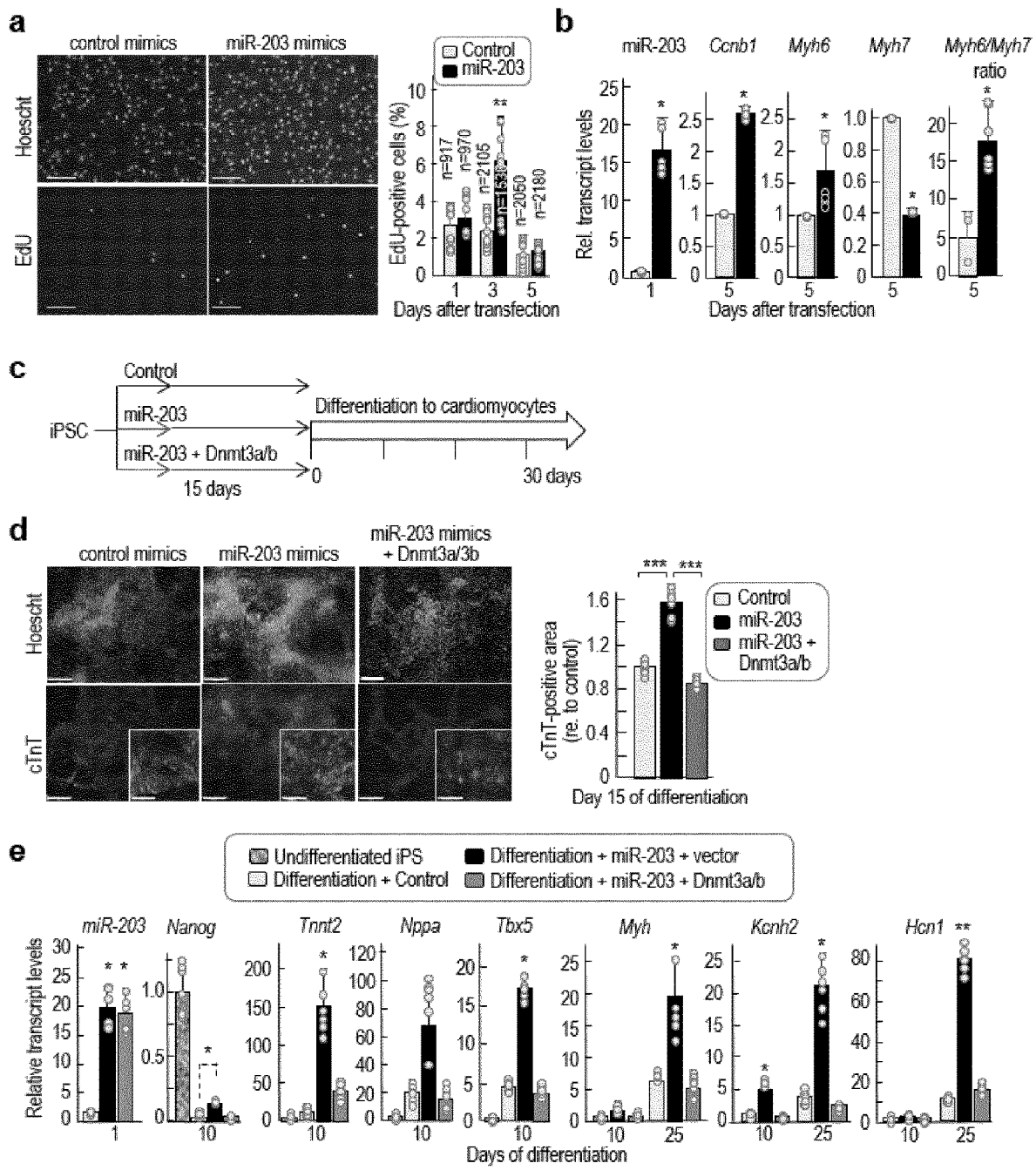

FIG. 14. Transient exposure of progenitor cells to miR-203 mimics enhances posterior differentiation to mature cardiomyocytes. a, Representative immunofluorescence showing EdU (green in the original) and nuclei (DAPI, blue in the original) staining of primary cardiomyocytes extracted at postnatal day 1 and transiently transfected with control or miR-203 mimics 24 hours after extraction. Pictures were taken three days after transfection. Scale bar, 60 μm. The histogram shows the percentage of EdU-positive cells at different days post-transfection. Data are mean±s.d. (n=2 independent experiments with 6 replicates each). b, RNA expression as determined by quantitative PCR of miR-203 (24 hours after transfection) and Ccnb1, Myh6 and Myh7 transcripts (5 days after transfection). The Myh6/Myh7 ratio is calculated as an indicator of cardiomyocyte maturation. Data are mean±s.d. (n=3 independent experiments). c, Experimental protocol followed for the differentiation of cardiomyocytes from iPSCs in the absence or presence of miR-203 mimics and Dnmt3a/b cDNAs. d, Representative immunofluorescences showing cardiac Troponin T (cTnT, green in the original) and nuclei (DAPI, blue in the original) staining of in vitro-generated cardiomyocytes derived from WT iPSCs transiently transfected with either control mimics, miR-203 mimics or miR-203 mimics+Dnmt3a/b cDNAs. Pictures were taken at day 15 of differentiation. Lower panels show a magnification detail of cTnT staining in each condition. Scale bars, 68 μm (inset, 25 μm). The cTnT-positive area in these cardiomyocytes is shown in the right histogram. Data are represented as mean±s.d. (n=2 independent experiments with 6 replicates each). e, miRNA or mRNA levels as determined by quantitative PCR of the indicated transcripts at different time points during cardiomyocyte differentiation in the indicated samples. Data are represented as mean±s.d. (n=2 independent experiments with 6 replicates each). In a, b, d, e, *P<0.05; P<0.01; *P<0.001 (Student's t-test).

Figure 15:
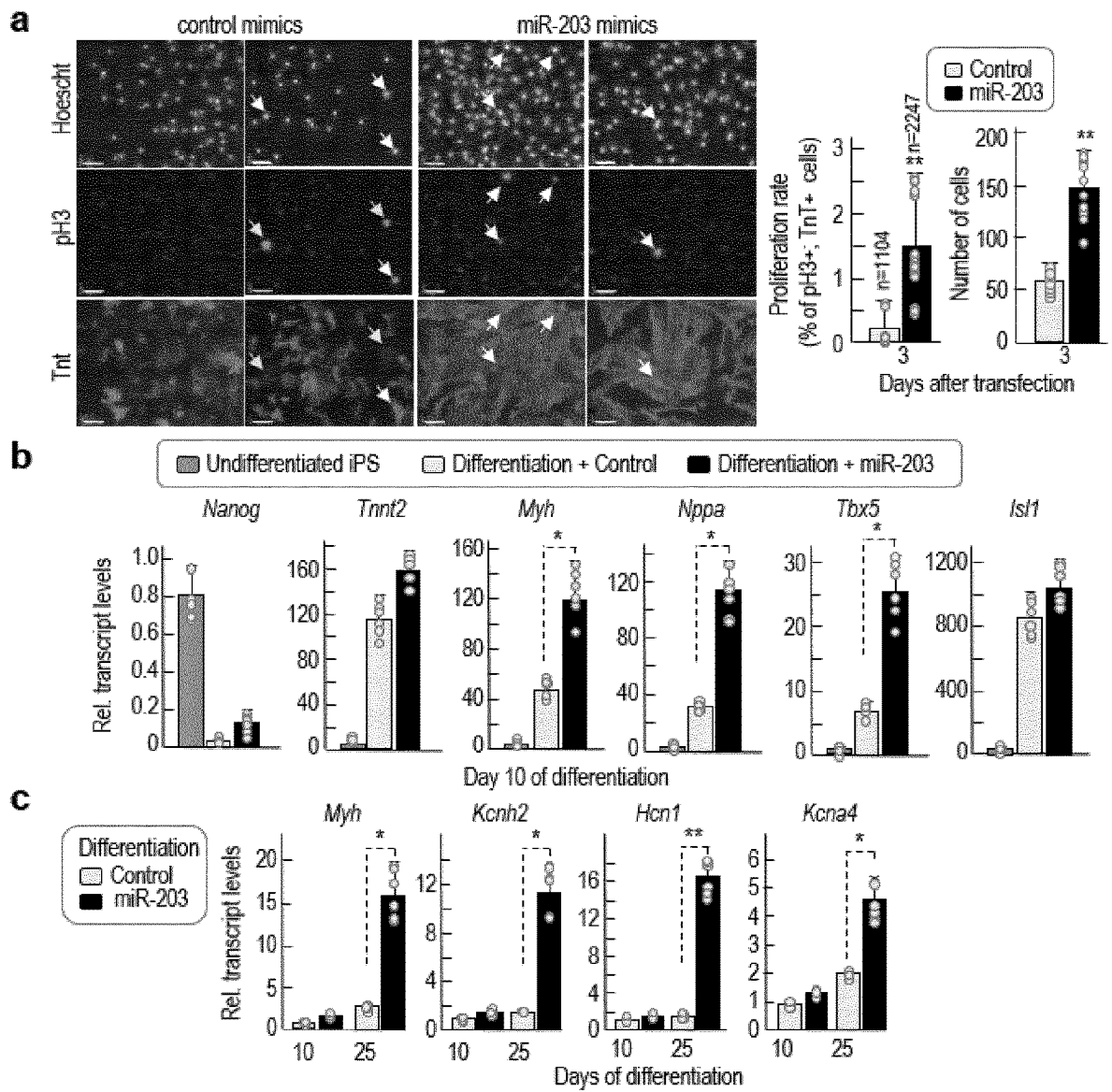

FIG. 15. Improved cardiomyocyte differentiation and maturation after transient expression of miR-203. a, Representative immunofluorescence showing phospho-Histone 3 (Ser-10; pH3) (in green in the original), cardiac Troponin T (cTnT, in red in the original) and Hoescht for nuclei staining (in blue in the original), as indicated in the left side of the imagenes, in primary cardiomyocytes extracted at postnatal day 1 and transiently transfected with control or miR-203 mimics 24 h after extraction. Images were taken three days after transfection. Scale bars, 64 μm. White arrows point to cardiomyocytes positive for pH3. Middle histogram shows the proliferation rate measured as the percentage of pH3 positive cells respect to the total number of cTnT positive cells at day 3 post-transfection. Data are mean±s.d. (n=2 independent experiments). The plot on the right shows the total number of cells at day 3 post-transfection. Data are represented as mean±s.d. (n=2 independent experiments). b, mRNA levels as determined by quantitative PCR of the indicated transcripts at different time points before and during cardiomyocyte differentiation. iPSCs were transfected either with control mimics or miR-203 mimics, maintained during 15 days in culture and then differentiated in vitro. c, Left panels: mRNA levels of the indicated transcripts at different time points during cardiomyocyte differentiation. Right panel: The beating frequency (measured as number of beats per 5 seconds) of these cardiomyocytes at day 15 of differentiation is also shown (n=8 different clones). In b-c, data are represented as mean±s.d. (n=2 independent experiments with 6 replicates each). In a-c, *P<0.05, **P<0.01 (Student's t-test).

Figure 16:
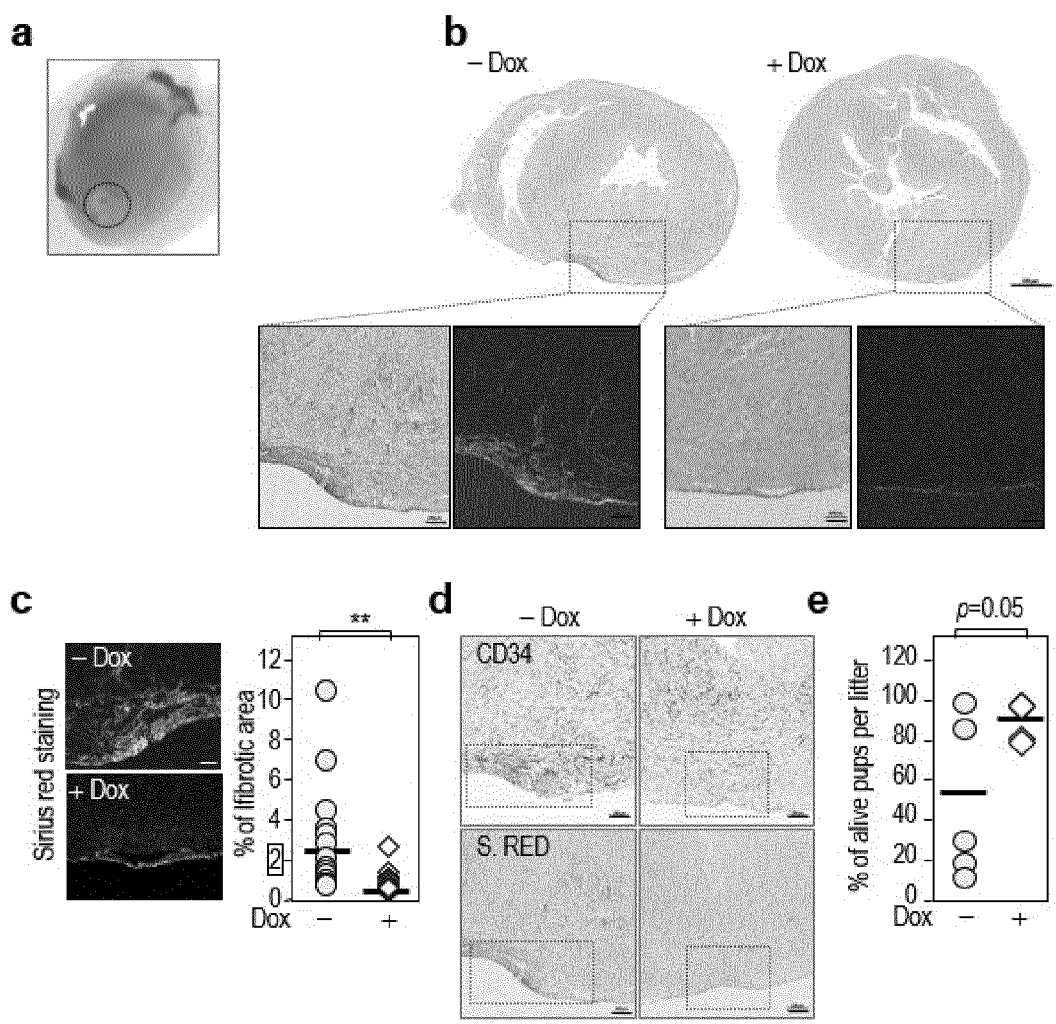

FIG. 16. Transient exposure to miR-203 enhances differentiation into mature cardiomyocytes and improves cardiac regeneration. a, Representative image of a postnatal-day-8 heart, 7 days after the cryoinjury. The area of cryolesion is highlighted. b, Representative images of heart sections from vehicle and Dox-treated mice stained with Sirius Red (scale bars, 500 µm). The magnification details show the fibrotic area in white (left) and polarized (right) light. Scale bars of the insets, 100 µm. c, Representative "black and white" images of the heart sections stained with Sirius Red from representative vehicle- or Dox-treated mice, showing in white the fibrotic area 7 days after the cryoinjury. Scale bar, 250 µm. The histogram shows the quantification of the percentage of fibrotic area relative to the total heart area in n=15 mice per condition, 7 days after the cryoinjury. **P<0.01 (Student's t-test). d, Immunohistochemical detection of Cd34 (mesodermal progenitors) and Sirius Red staining of heart sections from vehicle and Dox-treated mice. Representative images from 3 different mice are shown. Scale bars, 100 µm. The fibrotic area is highlighted. e, Quantification of the percentage of living pups per litter one day after the cryolesion. 5 litters were tested per condition. P=0.053 (Student's t-test).

Figure 17:
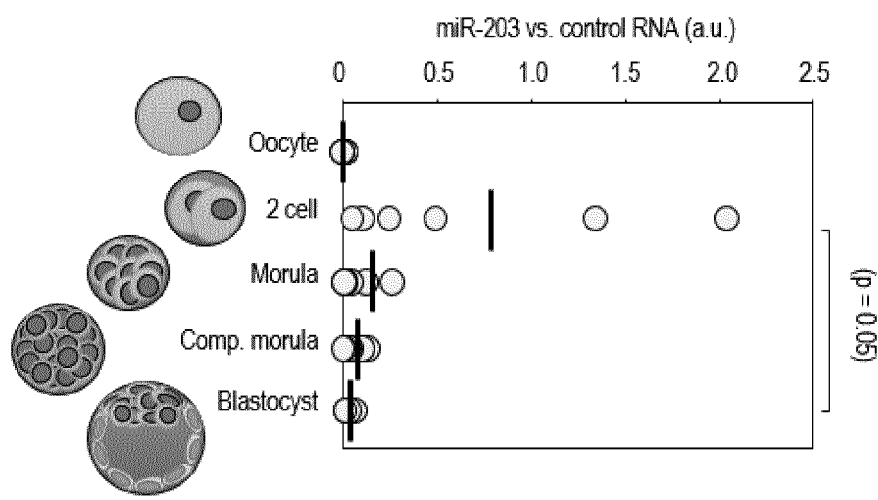

FIG. 17. miR-203 is induced at the 2C stage during embryonic development. miR-203 expression, as determined by qPCR, in five different stages of normal early development: oocyte, 2-cell embryo, morula, compacted morula and blastocyst. RNA was extracted from 30 different embryos and pooled in two independent groups for analysis by qPCR. RNA expression is normalized by a control miRNA (miR-16). Data represent 6 different qPCR measures. P=0.05 (Student's t-test) comparing 2C/morula versus compacted morula/blastocyst.

Figure 18:
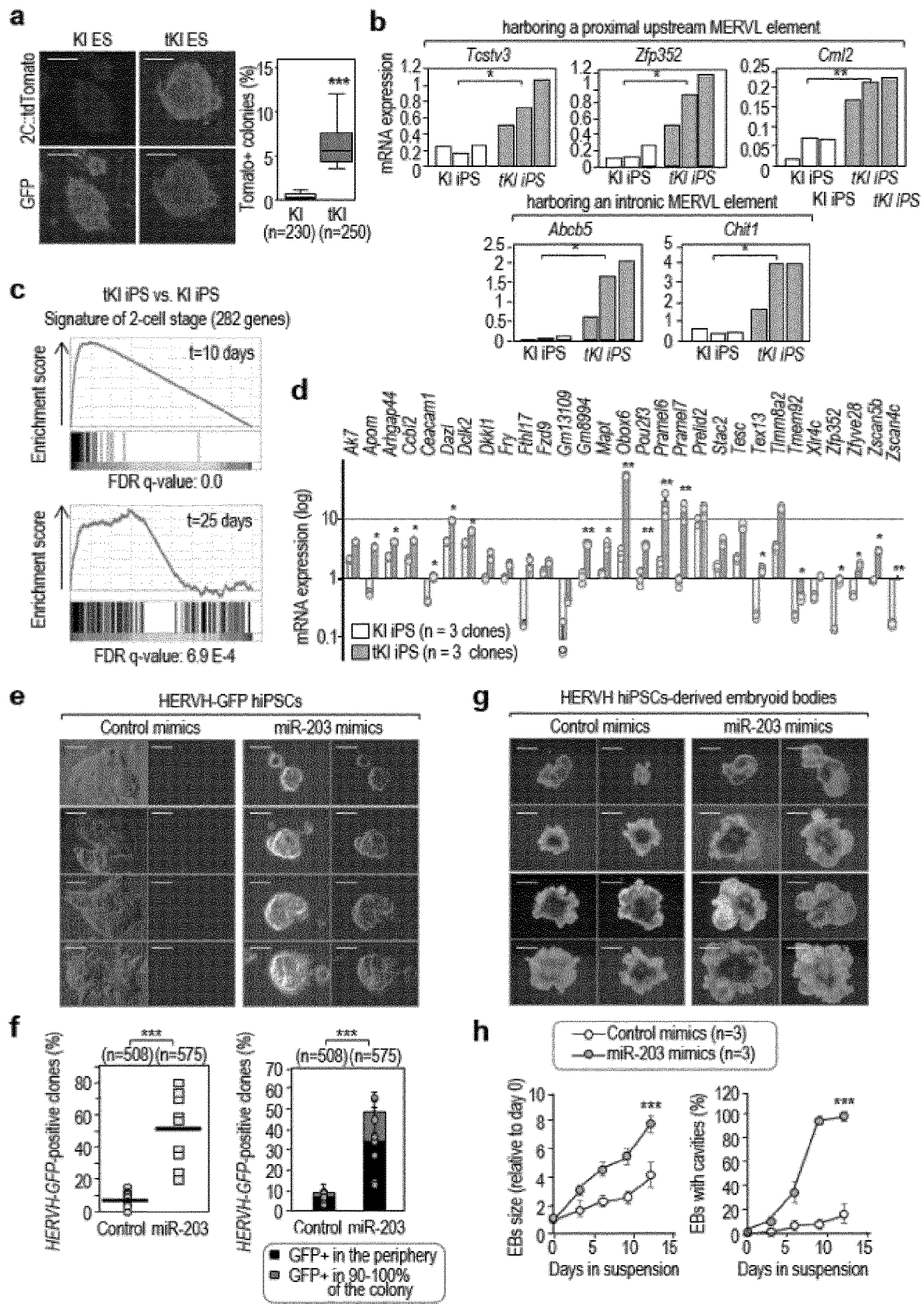

FIG. 18. Transient exposure to miR-203 induces 2-cell-like markers. a, representative immunofluorescence analysis of ESC colonies stably expressing the 2C::tdTomato reporter, and transiently transduced with GFP or miR-203-GFP viruses. Scale bar, 10 µm. Right plot shows the percentage of tdTomato-positive colonies out of the total GFP-positive colonies, 24 h after transduction. Data are represented as mean±s.e.m. (n=3 independent experiments). ***P<0.001 (Student's t test). b, RNA expression as determined by RNA sequencing of the indicated transcripts, known to be harboring a proximal upstream MERVL element (Tcstv3, Zfp352 and Cm12) or an intronic MERVL element (Abcb5 and Chia). Data show three independent wildtype iPSC (blue) or tKI iPSCs (red) clones. *P<0.05; **P<0.01 (Student's t-test). c, Enrichment plots of the 282-gene 2-cell signature (Biase et al., 2014) in tKI iPSCs 10 and 25 days after Dox withdrawal. d, Expression, as determined by RNA sequencing, of the indicated transcripts included in the 2C-signature. Data are mean±s.e.m (n=3 independent experiments). *P<0.05; P<0.01 (Student's t-test). e Representative images of human pluripotent stem cells (hiPSCs) expressing a long terminal repeat (LTR7) of HERVH endogenous retrovirus tagged by GFP. Cells were transfected with either control (left) or miR-203 mimics (right). White field and GFP expression for the same colonies are shown. Scale bars, 10 µm. f, Left plot shows the percentage of HERVH-GFP-positive colonies in the assay described in panel (E), five days after the miRNA transfection. Right plot shows the percentage of HERVH-GFP-positive colonies in which GFP is expressed only in the periphery of the clone (black) or in the majority of the cells constituting the colony (grey). Data are mean±s.e.m. (n=3 independent experiments; as indicated, 508 colonies for control mimics and 575 colonies for miR-203 mimics were counted). *P<0.001 (Student's t-test). g, Representative images of EBs derived from HERVH hiPSCs transiently transfected with either control (left) or miR-203 mimics (right) as indicated in (E,F), at different time points during the differentiation process. Scale bars, 500 µm. h, Quantification of EB size from panel g) and the percentage of EBs presenting internal large cavities during the indicated time course of differentiation. Data are mean±s.e.m. (n=3 independent experiments). ***P<0.001 (Student's t-test).

Figure 19:
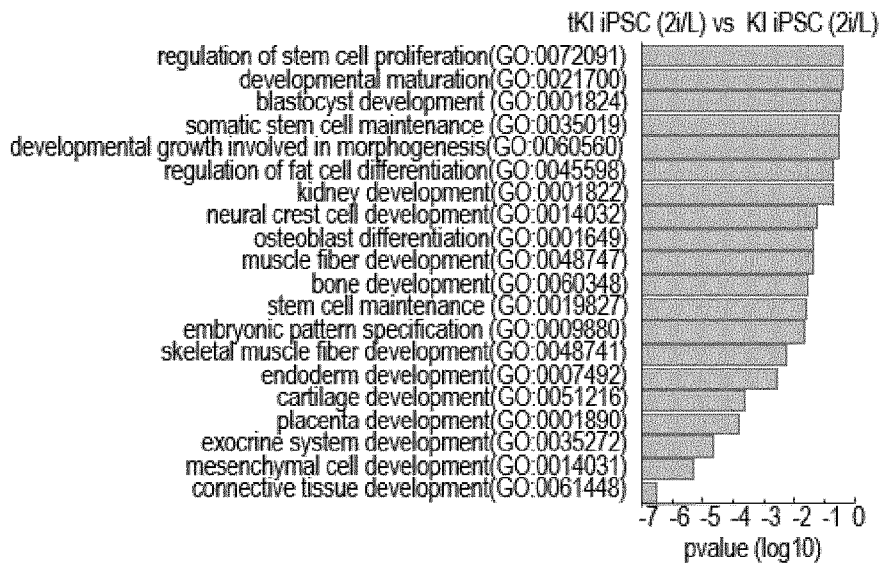
Figure 19:
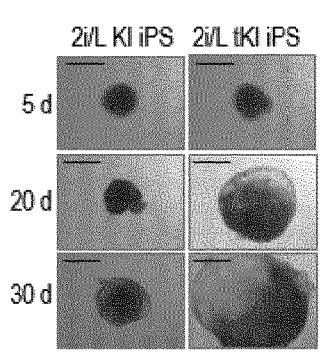
Figure 19:
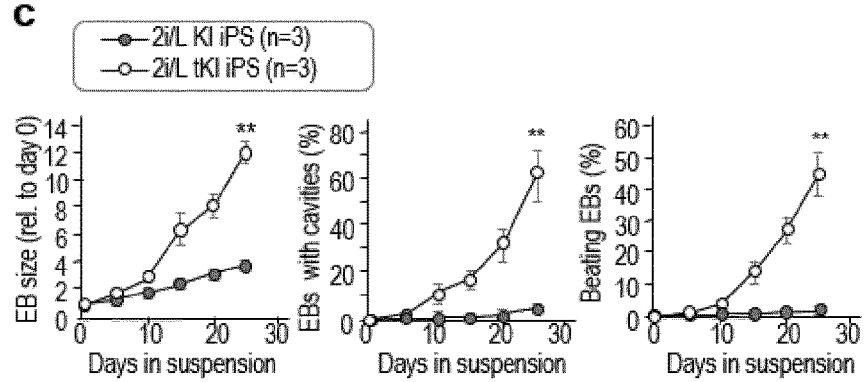

FIG. 19. miR-203 induces naïve pluripotency in cells cultured in 2i/LIF medium. a, Pathways from the Gene Ontology Database significantly deregulated in tKI iPSCs (doxicicline-induced iPSCs) versus un-induced iPSC, both cultured on 2i/L conditions. b, Representative images of EBs derived from un-induced iPSCs or doxicicline induced iPSCs (tKI iPSCs), cultured in 2i/L conditions during 10 passages, at different time points of the differentiation process. Micrographs are representative of three different experiments. Scale bars, 500 µm. c, Quantification of EBs size and the percentage of EBs presenting internal large cavities or beating from the same cells used in panels a) and b). Data are mean±s.e.m. (n=3 independent experiments). **P<0.01 (Student's t-test).

Figure 20:
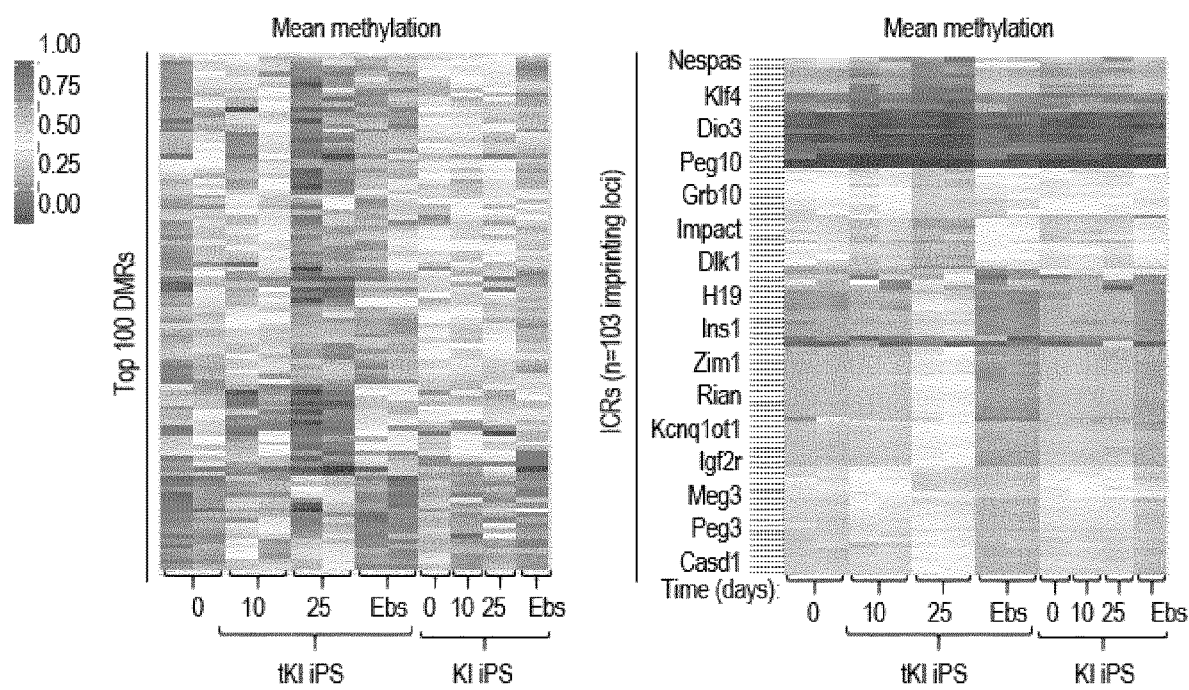

FIG. 20. miR-203 induces mild hypomethylation on imprinted genes. Heatmaps representing the methylation levels at the top Differentially Methylated Regions (DMRs; n=100; left panel) or the Imprinting Control Regions (ICRs; n=103 different imprinting loci; right panel) in the indicated samples. The scale of grey is applicable to both heatmaps. Left panel: In tKI iPSCs, t=0 has a methylation level proximal to 1.00, while in t=10 is gradually reduced and in t=25 the methylation level is closer to 0.00. In control KI iPSCs, the methylation levels are between 0.75 and 1.00 in all the time points indicated. Right panel: a slight hypomethylation is observed for the ICRs in tKI iPSCs t=25, not comparable to the one detected in the DMRs shown in left panel.

DETAILED DESCRIPTION OF THE INVENTION

The present invention, as indicated above, provides a method for improving the efficiency of pluripotent cells, particularly iPSCs, and therefore, generating naïve pluripotent cells more suitable for therapeutic approaches, very specially for their differentiation and maturation into differentiated cells useful for regenerative purposes.

The invention is based in the results of the assays disclosed in the Examples of the present application, which assays demonstrate that just a transient exposure to miR-203 sequences strengthen stemness potential of pluripotent cells and favours differentiation.

In the Examples below it is shown how transient overexpression of a single microRNA (miR-203), or an analogue thereof, potentiates differentiation of pluripotent cells (both embryonic stem cells and induced pluripotent cells) maintaining at the same time their stemness capacity. miR-203 significantly improves not only stem cell markers expression, teratoma formation containing cell types from the three primitive embryonic layers, and differentiation efficiency to any lineage. Even more importantly, miR-203 transient expression on iPSCs notably favors the stemness capacity of those cells to produce live-born progenies, as ESCs do. Both chimera contribution (of particular interest, in tetraploid complementation assays) and germline transmission are dramatically increased when iPSCs or ESCs have been exposed to a transient induction of the microRNA. Thus, it can be said that the pluripotent cells resulting from applying the method of the present invention to iPSCs (that is, by submitting iPSCs to an increased level of miR-203 transiently) show properties that are proper of pluripotent cells in the naïve state, so that the resulting cells can be considered naïve pluripotent cells. These results are consistent with the additional study carried out by the present inventors and disclosed in the present application, where miR-203 is identified as a microRNA preferentially expressed in the 2C-morula stages during preimplantation development in the mouse embryo.

It is remarkable that the mentioned effects, particularly the expansion of differentiation potential of pluripotent cells and the strengthening of the stemness potential, are achieved by increasing the level of miR-203 to which the cells are exposed (by transient expression from a vector previously introduced in the cell or by addition of miR-203 to the culture media of the cells), because miR-203 was considered by some authors as a stemness repressor (see Yi et al., 2008; Volinia et al., 2014) which limits stemness potential in the skin and the asymmetry hsa-miR-302(high)/has-miR-203a (low) has been found to be associated with stemness. In the same line, even though one skilled in the art had had knowledge of the review of Huang et al. (Huang et al., 2011) and had read that miR-203 cooperatively modulate Sox2 and Klf4 without having verified what it is commented indeed in the cited source of information for that statement (Wellner et al., 2009, where, as commented above, it is said that miR-203 cooperates with miR-200c and miR-183 to suppress stem factors), that one skilled in the art would have expected that an increase in miR-203 would lead to deficient stemness, because miR-203 represses targets. It can be said that every information in the prior art would lead to predict that miR-203 expression, whatever the environment or differentiation state of the cell, would repress, and not enhance, stemness potential.

Thus, it was not expectable that an increase in miR-203 levels will lead to improved stemness in ESCs or iPSCs that could be considered truly pluripotent and had not begun the process of commitment to a particular differentiated cell type or tissue, such as keratinocytes. In connection to that, it is important to remark that the assays disclosed in the present application and the results obtained are different from those described by Nissan et al. (Nissan et al., 2011) and do not interfer with them, because Nissan et al., as discussed above, reported that miR-203 becomes relevant in keratinocyte differentiation once the hESCs have been already committed to epidermal differentiation by an additional treatment (specifically, treatment with BMP4), which are conditions in which miR-203 becomes a critical factor involved in early keratinocyte commitment and that can be considered already known since 2008 (see Yi et al., 2008). And this is different from what is disclosed in the present application, where it is shown that the transient induction of miR-203 is relevant for pursuing a pluripotent naïve state, which is deriving lately in improved differentiation commitment. These two concepts are completely different, as well as their implications in regenerative medicine. In other words: transient expression of miR-203 acts as a stimulator of stemness potential of pluripotent cells, whatever their subsequent differentiation commitment is. This is shown, for instance, in the assays of the present application related to embroid body and teratoma, where it can be observed an improved differentiation capacity to the three germ layers of those pluripotent cells shortly exposed to miR-203, compared to their control counterparts.

Moreover, the results of the assays disclosed in the present application were also difficult to conceive having knowledge of the conclusions achieved after studies of the influence of miR-203 in nuclear survivin levels in hESCs (Kapinas et al., 2015), which studies had led to propose miR-203 as an inhibitor of pluripotency acting by negatively regulating survivin expression.

It is significant that de novo DNA methyltransferases likely play an important role in the effects observed after miR-203 transient overexpression. Significant improvement of the efficiency of iPS cells in the generation of quimeras and tetraploid complementation assays, that allow these cells to form complex teratomas and embryo-like structures in vivo, seem to be mediated, mechanistically, by direct miR-203-dependent repression of de novo DNA methyltransferases Dnmt3a and Dnmt3b, leading to erasure of global DNA methylation of pluripotent cells.

DNA methylation dynamics have been previously widely described, controlling both pluripotency and differentiation processes. General DNA hypomethylation and maintenance of genomic imprints are known to be essential to assure chimeric contribution and germline transmission, as proof of pluripotency. While the naïve pluripotent state is characterized by global DNA hypomethylation, the differentiation status is correlated with higher levels of methylation and upregulation of the de novo methyltransferases Dnmt3a and Dnmt3b, as well as their counteracting protein Dnmt3l.

Interestingly, downregulation of those de novo Dnmts is observed in cells of early preimplantation epiblasts, accompanying upregulation of pluripotency-related genes. Those features are recapitulated in the naïve state, and can be sustained in vitro under certain conditions. The derivation of embryonic stem cells in vitro with intact genomic imprints, even in the context of global DNA hypomethylation, is not easy to achieve. Imprint instability is normally assessed in some ESC lines and cultures, and the DNA methylation landscape is commonly altered, leading to low to medium efficiency in chimera contribution, germline transmission and differentiation. However, in our system, we have observed a global DNA hypomethylation in miR-203 transient-overexpressing pluripotent cells, while genomic imprints remain unaltered. We have described in detail how miR-203 targets the de novo methyltransferases Dnmt3a and Dmt3b, reducing global DNA methylation and therefore favoring naïve pluripotency. Dnmt1 remains unaffected in these conditions, presumably avoiding DNA methylation erase on genomic imprints. This is another proof of concept of the naïve state of miR-203 transient over-expressing IPSCs and ESCs.

Lack of these DNA methyltransferases in ESCs is known to induce progressive hypomethylation of chromatin with passages (Liao et al., 2015). Expression of miR-203-resistant Dnmt3a and Dnmt3b cDNAs rescue the phenotypes induced by miR-203 (FIGS. 9-15). Of note, whereas the severe and irreversible hypomethylation observed in Dnmt3a/b knockout cells blocks differentiation (Jackson et al., 2004; Okano et al., 1999), the hypomethylated state induced by miR-203 is reversible and differentiation is highly efficient and accompanied of potent DNA methylation (FIG. 7).

Therefore, the method of the present invention has several important differences with the previously known methods directed to improve the quality of cultured pluripotent cells that can be summarized as follows:

i) The method can be used in already-established pluripotent clones (iPSCs and ESCs) and it is therefore an additive procedure to the methods discussed above, and combinable with them. This is an important difference with regard to most variants of Yamanaka's original protocol, where the efficiency or the safety of the method are trying to be increased by replacing some of original Yamanaka's factors by other compounds or by adding additional compounds in order to carry out the reprogramming process. In the present case, the additional compound, miR-203, is added to already-established iPSCs or ESCs.

ii) Pluripotent cells exposed to miR-203 display enhanced function both in vitro and in vivo in the generation of differentiated and functional cells.

iii) The effect of the exposure to pluripotent cells to increased levels of miR-203 can also be achieved easily by using synthetic small RNA molecules that are analogues of miR-203, such as specific mimics, that are commercially available.

iv) Mechanistically, miR-203 has been observed to exert its effect by erasing the epigenetic memory of pluripotent cells, a factor known to act as a barrier in the establishment of pluripotent cells. This is another important difference with the methods where demethylases, for instance, are used during the reprogramming process to pluripotent cells, because that demethylation is irreversible or induces cytotoxicity, what makes the obtained cells useless for regenerative medicine. The present method, transiently exposing already-established iPSCs or ESCs to increased levels of miR-203 (or an analogue thereof), provokes a transient genome-wide hypomethylation that improves their pluripotency and, since such hypomethylation is transient and reversible, it also permits an expansion of their differentiation potential. Thus, the present method gives rise to naïve pluripotent cells that might be useful for obtaining gold differentiated cells applicable in regenerative medicine.

v) The exposure of already-obtained pluripotent cells to increased levels of miR-203 (or analogues thereof) levels (for instance, and preferably, by transient expression) means a safer alternative to some known methods, such as the methods where DNA methylation inhibitors such as AZA are used during reprogramming, since AZA is known to induce cell death. In that sense, it must be also pointed out that, differentially to other factors, miR-203 is a well established tumor suppressor, whose use also allows avoiding concerns related to the use of oncogenic factors during reprogramming (Tapia et al., 2016).

As can be seen in the Examples below, the pluripotent cells obtained after carrying out the method of the present invention exhibit improved stemness potential, when compared with their control counterparts, which can be observed thanks to the following features, which are characteristic of pluripotent cells in a naïve state:

(i) In vitro differentiation to embryoid bodies (EBs) is significantly increased compared to control iPSCs. EBs generated from iPSCs which have undergone the steps of the method of the invention (specifically, tKI iPSC-derived EBs) grow faster, differentiate better, show a higher percentage and efficiency at beating and exhibit a perfect architecture of the three germ layers. The differentiation and functionality of their cells is also revealed by the formation of long cavities, which is rarely found in control iPSC-derived EBs;

(ii) In vivo differentiation to teratomas is also dramatically improved when iPSCs that have undergone the steps of the method of the invention (specifically, tKI iPSCs) are injected in mice, when compared with their respective controls. The level of differentiation of the three germ layers is notorious, and some atypical tissues such as pancreas, bone marrow, cartilage or even extra-embryonic tissue (placenta) are easily found in tKI iPSC-derived teratomas. When these tKI iPSCs are injected intraperitoneally in mice, they are able to develop complex embryo-like structures, never found in wild-type iPSC injections. Those structures are characterized by the expression of several markers of embryonic development, the three germ layers and extra-embryonic tissues;

(iii) The expression of embryonic 2-cell-stage markers, such as certain retrotransposons, is higher in tKI iPSCs when compared to their WT counterparts. Moreover, the transcriptomic profile of those iPSCs illustrates how tKI iPSCs activate a number of signalling networks involved in development, morphogenesis, stemness maintenance, chromatin organization and cell fate commitment, proving their naïve state. Of interest, Principal Component Analysis, Hierarchical Clustering and Heatmap analysis of the RNA sequencing samples demonstrated the significant proximity between naïve tKI iPSCs and ES cells, compared to WT iPSCs. Tetraploid complementation assay is the most stringent assay to test pluripotency potential of iPSCs. There, tetraploid blastocysts are produced via the fusion of 2-cell stage embryos and are developmentally defective by only forming extraembryonic tissues in vivo. As expected, ES cells with full pluripotency compensate for the developmental deficiency of tetraploid embryos, and a full-term organism can be produced from ESCs together with extraembryonic tissues derived from such tetraploid embryos. While the efficiency to generate live-born progenies is around 20% for ESCs in such assays, iPSCs usually fail this stringent test and do not support "all-iPSC" mice. However, miR-203 transiently-expressing iPSCs proficiently generate live-born pups by 4n complementation, to a similar extent of that achieved using WT ESCs. Even more, those ESCs that have been exposed to transient miR-203 induction exhibit a significant higher competency in this test when compared to WT ESCs. The data clearly asserts that miR-203 improves the efficiency of iPSC technology.

(iv) Chimera contribution is definitely the best proof of concept to demonstrate the value of pluripotent (iPS or ES cells). The experiments of cell aggregation and even more importantly, tetraploid complementation assays show how tKI iPSCs contribute to chimera generation and germline transmission significantly more than their respective control iPSCs.

Additional data reinforcing the finding that exposure of iPSCs of ESCs to increased levels of miR-203 promotes naïve pluripotency and that the method of the present invention is advantageous with regard to other previously described methods aimed to sustain pluripotency in vitro are the following ones:

(i) miR-203 expression peaks at the 2-cell stage and in morula, in agreement with the data showing that this microRNA favors the expression of transcripts typical of the 2-cell stage. This observation supports the fact that miR-203 is relevant for acquiring naïve pluripotency in vivo, and thus it might be used as an advantage for boosting naive pluripotency in vitro.

(ii) Expression of miR-203 in PSCs induces the expression of genes typically expressed in the embryonic 2-cell stage. In addition to a specific 2-cell reporter, the expression of transcripts included in the "2-cell transcriptome" have been analysed in detail. The fact that miR-203 induces 281 out of the top 282 genes included in the 2-cell signature is a remarkable finding. Again, these observations reinforce the idea of miR-203 promoting naïve pluripotency.

(iii) miR-203 also significantly improves developmental potential in 2i/LIF conditions, the former standard for maintaining stemness potential. In addition, the analysis of Imprinting Control Regions shows that miR-203 has little effect in these regions compared to 2i/L conditions, thus explaining the significant improvement of miR-203-treated cells in multiple in vivo assays. These results support the preferable use of miR-203 over the former methods aimed to sustain pluripotency in vitro (iv) The effect of miR-203 has been also tested in human cells, showing similar effects in the expression of 2-cell markers, and differentiation potential. Thus, observations in mouse pluripotent cells are extended to human pluripotent cells.

(v) The relevance of Dnmt3a/b as relevant targets is shown by rescue assays as well as Dnmt3a/b knockdown in WT PSCs, thus mimicking miR-203. These data reinforce the identification of de novo DNA methyltransferases as miR-203 targets responsible for the described phenotype.

Additionally, pluripotent cells exposed to miR-203 displayed enhanced differentiation and maturation potential, as is demonstrated by the following found effects:

(i) The number of tissues and level of differentiation is increased in tKI cells (pluripotent cells that have undergone the steps of the method of the present invention), as observed in the embryoid body differentiation assays, formation of complex teratomas and embryo-like structures including differentiated tissues usually not observed such as bone marrow, placental tissues or exocrine pancreas. In addition, teratomas derived from tKI cells, but not control teratomas, contain cells positive for the hormone insulin, suggesting the presence of differentiated pancreatic beta cells, and further illustrating the expanded capacity of tKI cells in differentiation to multiple cellular lineages.

(ii) Differentiation and maturation of iPSCs into cardiomyocytes is improved as detected by the expression of maturation markers as well as functional assays.

(iii) Differentiation of neonatal cardiomyocytes is improved as well as the maturation level they reach after exposure to miR-203.

(iv) Tissue regeneration assays (assays that typically are not included in reports of improved pluripotent cells, given the complication for cells improved in vitro in performing properly in complex regeneration assays in vivo show that miR-203 expression significantly potentiates heart regeneration and overall survival after cardiac injury, a result that strengthen the differentiation potential of pluripotent cells submitted to miR-203 treatment and their functionally in vivo and that suggests the relevance of this microRNA in regeneration medicine.

It is remarkable that the method of the present invention differs from the methods and means for deriving cardiomyoctes from iPSCs or ESCs disclosed in International Patent Application WO2014201254A1 in that microRNAs of the let-7 family are the only ones mentioned in said International Patent Application as important microRNAs for in vitro cardiac maturation starting from pluripotent cells and other microRNAs are not mentioned. Then, the present invention provides an alternative and not previously suggested method for cardiomyocyte differentiation, starting from pluripotent cells that have been previously submitted to a transient increased of level of miR-203 (either by transient expression in the cells or transient exposure of the cells to miR-203 or an analogue thereof by addition to their culture medium), which pluripotent cells are later submitted to cardiomyocyte differentiation achieving an improve in effectiveness, since the resulting cardiomyocytes are mature and functional.

Given their potential utility for feature clinical applications, it can be considered that it is an important embodiment of the method of the present invention that one wherein the enhancement of differentiation potential of the cells is characterized by an improvement of differentiation efficiency, for instance to cardiomyocytes, but also to other differentiated cells, specially those of clinical interest such as cells of nervous system (neurons and glial cells, for instance), chondrocytes, pancreatic beta cells . . . .

miR-203 improves the potential of already-established ES and iPS cells to contribute to multiple cell lineages. Thus, the method of the present invention can be also defined as a method to improve the stemness properties/potential of already-established pluripotent cells, (since it works with embryonic stem cells and with induced pluripotent stem cells), and/or as method to enhance differentiation and/or maturation potential of pluripotent cells. Thus, the pluripotent cells that have undergone by the steps of the method of the invention exhibit a) higher percentage, faster growing, better differentiation, better efficiency at beating and better architecture of the three germ layers compared to control cells, when differentiated to embryoid bodies; b) improvement of in vivo differentiation to teratomas; and c) higher expression of 2-cell-stage markers. Now, regarding the enhancement of differentiation and/or maturation potential, pluripotent cells that have underwent by the steps of the method of the invention exhibit: a) an increased number of tissues and higher level of differentiation compared to control, when differentiated to embryoid bodies; b) formation of complex teratomas and embryo-like structures that include differentiated tissues usually not observed in control conditions; c) improved differentiation and maturation potential when specifically differentiated to cardiomyocytes, including faster and increased expression of maturation markers and faster acquisition of their functionality.

As commented above, the effects of the exposure to increased levels (by overexpression or addition to the culture medium) of miR-203, or an analogue thereof, can be seen both in induced pluripotent stem cells (iPSCs) and embryonic stem cells (ESCs). For the purposes of the present invention, both the iPSCs and the ESCs can be cells derived of any mammal. Human ESCs can be optionally excluded. When the ESCs are human ESCs, it is preferred that the human ESCs used in the method of the invention have been obtained by a method that does not imply the destruction of the embryos, such as the method described in Chung et al., 2008. But, in order to above moral or legal concerns related to the use of human ESCs and for handling reasons, it is preferred that the method of the invention is carried out with iPSCs. For easiness of generation and handling, it is particularly preferred that the iPSCs are in culture when the method of the invention is applied on them, and it is also preferred that the generation of said iPSCs has occurred in vitro, from cultured differentiated cells such as fibroblasts, although the use of in vivo generated iPSCs (Abad et al., 2013) is compatible with the method of the present invention and can be considered included in its scope. For obtaining in vitro (in culture) generated iPSCs, any of the known reprogramming procedures can be used, including the original Yamanaka method (contacting somatic differentiated cells with a nuclear reprogramming factor comprising a gene product of each one of the following families: Oct family, Klf family, Myc family and Sox family) and any of its variants.

The Examples of the present invention contained some assays wherein the increased levels of microRNA-203 are obtained thanks to its genetically-induced overexpression in the iPSCs cells, due to fact that such cells have been reprogrammed in vitro from differentiated cells (fibroblasts) that have been extracted from a mouse model wherein a Doxyclycline-inducible cassette for miR-203 expression is included. Then, in that case, the increased levels result directly from the intracellular overexpression of miR-203; such increase occurs transiently due to the fact that doxycycline is added only for 3-5 days. Other assays, as some of the assays described in Example 4, have been performed with wild-type iPSCs in culture and the exposure of the iPSCs to the increased levels/amounts of miR-203 has been achieved by the addition of a miR-203, specifically a chemically-modified double-stranded miR-203, to the culture media; the results obtained with this mimic of natural miR-203 show that the addition of miR-203 to the culture medium is a possible embodiment of the method of the present application that also solve the same technical problem. As the miR-203 or its analogue or mimic has to enter the cell to exert its effect, adding to the endogenous miR-203 amount (naturally present in the cell) the miR-203 amount resulting from the penetrance of the added compound from the culture medium, the result is analogously that cells are exposed to increased level of miR-203 (or an analogous compound with the same kind of activity). For that reason, the step that is necessary to take to perform the method of the present invention has been defined as exposing the cells to increased levels of miR-203. Even if the starting level could be considered to be zero (0) (as might be the case in the culture medium or in some of the models used in the Examples below), it could be considered an increase in the levels: from 0 to a certain amount.

Such increase of miR-203 levels can be achieved by the use of expression vectors well known in the state of the art, wherefrom miR-203 can be expressed, for instance, because a coding sequence of the immature progenitor form (for instance, hsa-miR203, represented by SEQ ID NO:2, in the case of human beings or mmu-miR-203, represented by SEQ ID NO:3, in the case of *Mus musculus*), which form will give rise to the corresponding mature form in the cell (hsa-miR-203a-3p, represented by SEQ ID NO:1, for human beings, or mmu-miR-203-3p, represented by SEQ ID NO:4, for *Mus musculus*). It can be seen that the human and the mouse mature forms are identical, so the use of precursor forms and/or mature forms of one species which is different from the species of origin of the pluripotent cells is compatible with the method of the invention and comprised in its scope, specially among human beings, both when the microRNA is directly added to the culture media or when is produced from or as a expression product from a vector.

Also possible embodiments are those that start with a mutated differentiated cell that has inserted in its genome an expression cassette wherefrom the microRNA or its precursor is expressed, as in some Examples of the present invention.

As transient expression in preferred (for instance, 3-5 days), it is preferable that the coding sequence giving rise to the microRNA or its precursor is under the control of an inducible promoter, as the tetracycline inducible promoter (inducible, for instance, by doxycycline) used in Examples of the present application, so that the time of expression in easily controllable and stoppable by removing the inducible compound. It is also possible, and can be considered another possible embodiment, that the expression vector is a plasmid or a non-integrative virus-derived vector, such as those derived from viruses such as adenoviruses of adeno-associated viruses, which facilitates a transient expression by themselves without additional control.

The product of the expression can be an mRNA that exhibits a part that corresponds to the molecule of the miRNA and a coding sequence of a tag or a protein usable, for instance, as marker.

Another possible embodiment, which is one of the preferred ones, is adding miR-203, or an analogue thereof, to the culture medium of the already-generated pluripotent cells. and, when transient exposure is desired, removing it from the culture medium when the desired exposure time (for instance, 3-5 days, as previously commented) is completed. Transient transfection of such microRNA mimics permits transient exposure (around 3-5 days, as previously commented). In that case, both the mature or the precursor molecule of miR-203 can be added. As discussed above, in the case of miR-203, the most abundant mature form is the one originating from the 3' arm of the pre-miRNA (hsa-miR-203a-3p in human beings and mmu-miR-203-3p in mice), which is the form responsible, at least in a high level, for the effects described in the present application; therefore, it is the form preferentially used in the present method, it is a possible embodiment of the present method to submit the pluripotent cells to a mixture of both mature forms, the one originating from the 3' arm and the one originating from the 5' arm, like in some assays of the present application, so that the endogenous scenario in the cells is faithfully mimicked faithfully.).

The use of synthetic compounds instead of the natural molecule of miR-203 is possible, as it is demonstrated in some Examples of the present invention. It is particularly considered the use of "analogues". RNA analogues are molecules that are similar to the natural microRNAs, but which contain at least a modification that makes them different and distinct. Included in the definition of RNA analogues are those RNA molecules where at least one nucleotide is replaced by another one: given that the complementarity among an microRNA and the fragment of the mRNA 3'UTR with which they base-paired is hardly ever complete (100%), changes in the microRNA sequence are admissible, provided that there are still base-pairing, so that an RNA analogue can be at least 50-60% similar to a natural microRNA, provided that its function is still accomplished. To that aim, it must be taken into account that there is always a region of 6-8 nucleotides, known as the seed region, where the complementarity among microRNA and mRNA 3'UTR is complete (100%) or almost complete (see FIG. 10 for the seed region with regard to Dnmt3a and Dnmt3b 3'UTR), so that it is advisable not to modify nucleotides of the seed region.

More frequently, but compatible with the previous modifications, there are chemical modifications in the nucleotides (the units of the microRNA), that give rise to analogues of nucleotides. Such modifications are usually made to increase stability and/or resistance to nucleases, facilitate entry into the cell, increase the strength of interaction among microRNA and mRNA, increase the desired activity of the microRNA and/or bias the processing of the microRNA through a particular cellular pathway (such as RISC, the RNA-induced silencing complex, that incorporates one strand of a small interfering RNA or a microRNA, uses it as a template for recognizing complementary mRNA and, thereafter, activates RNase and cleaves the RNA). Such modifications are usually in the sugar moiety and/or in the phosphate bond, and include the addition of one or more non-nucleotide moieties. Some common modifications are: the commonly used phosphorothyoate bonds instead of the phosphate bonds; modifications at the 2' position of the sugar moiety such as 2'-O-methyl or 2'-O-methoxyethyl modifications; modifications where the ribose exhibits a link connecting the oxygen at 2' with the carbon at 4', thus blocking the ribose in the conformation 3'-endo (LNAs: locked nucleic acids) or 2'-O, 4'-C ethylene bridged nucleic acids (ENA); the replacement of the sugar backbone by an amide-containing backbone such as an aminoethylglycine backbone, as in peptide nucleic acids (PNAs); use of PMOs (nucleic acids where the ribose moiety is replaced by a morpholine group); and other modifications well known by those skilled in the art that can be found reviewed, for instance, by Kole et al. (2012). As the nitrogenous bases are the element less commonly modified in the analogues of nucleotides, the comparison of their homology or identity with regard to fragment or the whole sequence of natural oligonucleotides or polynucleotides is more properly done with regard to the sequence of nitrogenous bases. Modifications at at least one of the strand ends, such as the addition of one of more unities of moieties of compounds such as cholesterol, cholestanol, stigmasttrol, cholanic acid and ergosterol and, also optionally and additionally, a linker moiety that attaches the conjugate moiety to the strand, are also common, specially to facilite the entry of the microRNA analogue into the cell.

Also included within the microRNA analogues, as the term is used in the present application, are the RNA mimics, specifically microRNA mimics (miRNA mimic). An RNA mimic, as commented above with regard to US20130345289A1, is a synthetic miRNA that has enhanced stability due to modified nucleotides or structural modifications (e.g. bulges or loops), and also those small, chemically modified double-stranded RNAs that mimic endogenous miRNAs and enable miRNA functional analysis by up-regulation of miRNA activity. MicroRNA mimics added to culture media are incorporated by the cells and act directly as double stranded molecules (cell expression is not required) that copycat faithfully their respective microRNA, miR-203 in the present case. The method where miR-203 mimics (only one or a mixture thereof) are added to the culture medium of the iPSCs, as in some Examples of the present invention (such as Example 4), is a preferred embodiment of the present invention, especially when the mimic is characterized by:
  a. being an RNA-modified molecule wherein at least one of the nucleotides is replaced by a chemically modified nucleotide, wherein the chemical modification is selected from the group of:
    i. replacing one or more phosphate bonds by phosphorothyoate bonds,
    ii. one or more modifications at the 2' position of the sugar moiety selected from 2'-O-methyl or 2'-O-methoxyethyl modifications; and/or
    iii. one or more modifications in the ribose moiety selected from the group of: those that give rise to a link connecting the oxygen at 2' with the carbon at 4', thus blocking the ribose in the conformation 3'-endo (LNAs: locked nucleic acids) or 2'-O, 4'-C ethylene bridged nucleic acids (ENA); the replacement of the sugar backbone by an amide-containing backbone such as an aminoethylglycine backbone, as in peptide nucleic acids (PNAs); and use of PMOs (nucleic acids where the ribose moiety is replaced by a morpholine group), and combinations thereof;
  b. being a double stranded molecule with a duplex region of between 16 and 31 nucleotides in length and which contains a fragment which is at least 50% identical in their sequence to the sequence of nitrogenous bases of the RNA molecule represented by SEQ ID NO:1 (hsa-miR-203a-3p) or SEQ ID NO:4 (mmu-miR-203-3p), and
  c. optionally, additionally comprising at at least one end of at least one of the strands a conjugate moiety comprising one or more units of cholesterol, cholestanol, stigmasttrol, cholanic acid and ergosterol and, also optionally and additionally, a linker moiety that attaches the conjugate moiety to the strand, and
  d. also optionally and additionally, presenting one or more mismatches among the two strands.

Examples of specific microRNA mimics can be also found, for instance, in United States Patent applications US 2009/0209626 and US 2011/0263675, both of them of Dharmacon, Inc., where the mimics are specific cases of the mimics described above. Very preferred are microRNA mimics such as the miR-203 mimics of the miRIDIAN series of Dharmacon (http://dharmacon.gelifesciences.com/rnai-and-custom-rna-synthesis/microrna/miridian-microrna-mimics/) used in assays of the present application that commercializes mimics of miR-203 of *Homo sapiens, Mus musculus* and other species such as *Rattus norvegicus*. miRIDIAN mimics are chemically enhanced with the ON-TARGET modification pattern to preferentially program RISC with the active microRNA strand. This modification includes an RNA where the first and second nucleotide of the sense region each has a 2'-O-methyl moiety, and the antisense strand is phosphorylated at its 5' end, wherein such an on-target modification also refers to a proprietary modification coined On-Target™ (Dharmacon, Inc.). In any event, on-target modifications can be used to help reduce off-target effects by blocking the sense (passenger) strand from being taken up by the RISC process. In any case, other examples of microRNA mimics can be found for instance in Sigma Aldrich, which commercializes also hsa-miR-203a mimics (HMI0357).

The naïve pluripotent cells resulting from putting into practice the method of the invention starting from iPSCs are different from said starting iPSCs, as can be seen in Table 3. The obtained naïve pluripotent cells, when subjected to well-established differentiation protocols, continue to express pluripotency markers such as Nanog, Oct and Sox2, while they co-exist with cells that express differentiation markers such as Nestin, Gata4 and CD34. Thus, the resultant population of cells is characterized by expressing both pluripotency markers and differentiation markers are also a goal of the present invention, particularly those obtained by the method of the present invention.

The assays disclosed in the Examples below show that controlling transient miR-203 expression in iPSCs and also in ESCs improves the ability of these cells to differentiate into multiple cells lineages and to reach further maturation properties without interfering with there self-renewal properties. Thus, the method of the present invention and the pluripotent stem cells obtained from it open new possibilities for the clinical application of pluripotent stem cells and solve some of the difficulties that remained to be solved in order to seriously think and planify their use for clinical purposes.

Pluripotent stem cells have the potential to become research and clinical tools to understand and model diseases, develop and screen candidate drugs, and deliver cell-replacement therapy to support regenerative medicine. Reprogramming technology offers the potential to treat many diseases, including neurodegenerative diseases, cardiovascular disease, diabetes, and amyotrophic lateral sclerosis (ALS). In theory, easily accessible cell types (such as skin fibroblasts) could be biopsied from a patient and reprogrammed, effectively recapitulating the patient's disease in a culture dish. Such cells could then serve as the basis for autologous cell replacement therapy. Because the source cells originate within the patient, immune rejection of the differentiated derivatives would be minimized. Yet while iPSCs have great potential as sources of adult mature cells, much remains to be learned about the processes by which these cells differentiate. The method of the present invention and the pluripotent cells obtained from it can be seen as a new and improved research tool that may be of use for understanding the process by which pluripotent cells differentiate and, also, a useful improvement that facilitates and makes more feasible the clinical application of said cells, after their differentiation, specially for regenerative medicine. Therefore, the use of the pluripotent cells of the present invention for obtaining differentiated cells, the methods for obtaining differentiated cells that use as starting material the pluripotent cells of the present invention, as well as the methods for obtaining differentiated cells from iPSCs which comprise a step such as the characterizing step of the method of the present invention (the exposure of the cells to increased level of miR-203) are comprised with the scope of the present invention.

Possible uses of the present technology, (the methods of the present invention and the cells obtained form them), include:

The field of cardiac regeneration. iPSCs created from human and murine fibroblasts can give rise to functional cardiomyocytes that display hallmark cardiac action potentials. However, the maturation process into cardiomyocytes is impaired when iPSCs are used—cardiac development of iPSCs is delayed compared to that seen with cardiomyocytes derived from ESCs or fetal tissue. Furthermore, variation exists in the expression of genetic markers in the iPSC-derived cardiac cells as compared to that seen in ESC-derived cardiomyocytes. Therefore, iPSC-derived cardiomyocytes demonstrate normal commitment but impaired maturation, and it is unclear whether observed defects are due to technical (e.g., incomplete reprogramming of iPSCs) or biological barriers (e.g., functional impairment due to genetic factors).

Neural regeneration, including the modelling and treatment of neurodegenerative diseases, such as Parkinson's disease, Huntington's disease, amyotrophic lateral sclerosis or spinal muscular atrophy. Patient-derived iPSCs can be rewound to affected neuronal subtypes via in vitro differentiation or repaired iPS cells using gene targeting to repair disease-causing mutation. Still, the protocols for applying IPSC-based regeneration in neurodegenerative disorders are far from reality. Also, greater progress has been made in generating matured populations of distinct neurons and glia for the purpose of screening drugs and replacement therapy. However, these cells may not truly reflect the cellular responses to compounds that the body would have at a physiological level. Lastly, researchers still face the problems of low efficiency conversion and laborious to conduct. The average conversion efficiency of such methods is less than 1%, which further restrict the extensively use of the technology.

Remodelling in a cartilage regeneration system. Since articular cartilage is not restored by natural healing, many attempts have been made to improve the quality of this tissue repair. Autologous chondrocyte transplantation has changed the paradigm of the treatment of cartilage defects from repair to regeneration, and this has been demonstrated in randomised trials proving the concept of regenerating tissue in a cell-based therapy approach. In this scenario, the present inventors speculate that miR-203 treatment in autologous chondrocytes prior transplantation might facilitate the remodelling of the damaged tissue and its full regeneration.

As controlling transient miR-203 expression in iPSCs and also in ESCs improves the ability of these cells to differentiate into multiple cells lineages (in particular, to cardiomyocytes) and to reach further maturation properties without interfering with there self-renewal properties, the method of the present invention means an important improvement for the generation of differentiated cells applicable in the above mentioned fields. Thus, the use of the pluripotent cells obtained by the method of the present invention for obtaining differentiated cells applicable in the above mentioned fields (cardiac regeneration, neural regeneration and cartilage regeneration) that is, cardiomycytes, neural or glial cells, chondrocytes and insulin-producing cells, is a preferred embodiment of the use of the pluripotent cells of the present invention.

It must be pointed out that transient exposure to miR-203 sequences improves both functional differentiation and maturation, as it is shown in the Examples of the present application, especially Example 4, related to differentiation and maturation of cardiomyocytes. Therefore, the possible therapeutic uses of this microRNA in regenerative medicine, such as neural regeneration, cartilague regenation, replacement of insulin-producing cells and, very especially, cardiac regeneration, are supported by the assays disclosed in the present application.

Together, it can be concluded that modulating the DNA methylation landscape of pluripotent cells by exposure to small microRNA mimics may enhance the performance of these cells in multiple functional assays, including the differentiation and maturation to multiple cellular lineages of interest in regenerative medicine.

The present invention will be explained in more detail by means of the Examples and Figures set forth below.

EXAMPLES

Summary of the Experimental Procedure

The present inventors have generated a mouse model in which miR-203 expression can be modulated by Doxycicline (DOX) treatment. Their knock in animal model (Co-1A_miR203; Rosa 26_rtTA) permits an over-expression of more that 100 fold of this microRNA whenever the animal-or the cells derived from the animal—are exposed to Doxycycline treatment. Their first approach was extracting the mouse embryonic fibroblasts from those mice, reprogram them in vitro using the Yamanaka factors and generate miR-203 knock in inducible pluripotent cells (miR-203 KI iPSCs). Those iPSCs were then treated with DOX for 3 to 5 days, and then exposed to DOX withdrawal for several passages. Those iPSCs have been named as "transient KI (tKI) iPSCs" to simplify. Then, several readouts were analysed to demonstrate how those tKI iPSCs exhibit an improved stemness potential, when compared with their control counterparts (the very same iPSC clone treated with vehicle): (i) In vitro differentiation to embryoid bodies (EBs) is significantly increased in tKI compared to control iPSCs. tKI iPSC-derived EBs grow faster, differentiate better, show a higher percentage and efficiency at beating and exhibit a perfect architecture of the three germ layers. The differentiation and functionality of their cells is also revealed by the formation of long cavities, which is rarely found in control iPSC-derived EBs; (ii) in vivo differentiation to teratomas is also dramatically improved when tKI iPSCs are injected in mice, when compared with their respective controls. The level of differentiation of the three germ layers is notorious, and some atypical tissues such as pancreas, bone marrow, cartilage or even extra-embryonic tissue (placenta) are easily found in tKI iPSC-derived teratomas. When these tKI iPSCs were injected intraperitoneally in mice, they were able to develop complex embryo-like structures, never found in WT iPSC injections. Those structures are characterized by the expression of several markers of embryonic development, the three germ layers and extra-embryonic tissues; (iii) the expression of 2-cell-stage markers, such as certain retrotransposons, is higher in tKi iPSCs when compared to their WT counterparts. Moreover, the transcriptomic profile of those iPS cells illustrates how tKI iPSCs activate a number of signalling networks involved in development, morphogenesis, stemness maintenance, chromatin organization and cell fate commitment, proving their naïve state. Of interest, Principal Component Analysis, Hierarchical Clustering and Heatmap analysis of the RNA sequencing samples demonstrated the significant proximity between tKI iPS and ES cells, compared to WT iPSCs; (iv) chimera contribution is definitely the best proof of concept to demonstrate the value of iPS or ES cells. The provided experiments of cell aggregation and even more importantly, tetraploid complementation assays showed how tKI iPSCs contribute to chimera generation and germline transmission significantly more than their respective control iPSCs.

The inventors' secondary approaches to further validate the data were directed to reproduce those proofs of concept in some other different models. Thus, it was demonstrated that the very same effects were observed when the miR-203 was transiently over-expressed in a number of clones of WT IPSCs or WT ESCs. The quality of transient miR-203 pluripotent cells (either iPSCs or ESCs) was in all cases better than their control counterparts. The over-expression was reproduced also using retroviruses (pMCSV) that are silenced in pluripotent cells after a few days from transduction, allowing a transient expression of the microRNA. Finally, and very important, the data were reproduced transfecting the miR-203 by using microRNA mimics and ordinary methods for RNA transfection, such as Lipofectamine RNAi Max (Invitrogen) or Dharmafect (Dharmacon).

Figure 1:
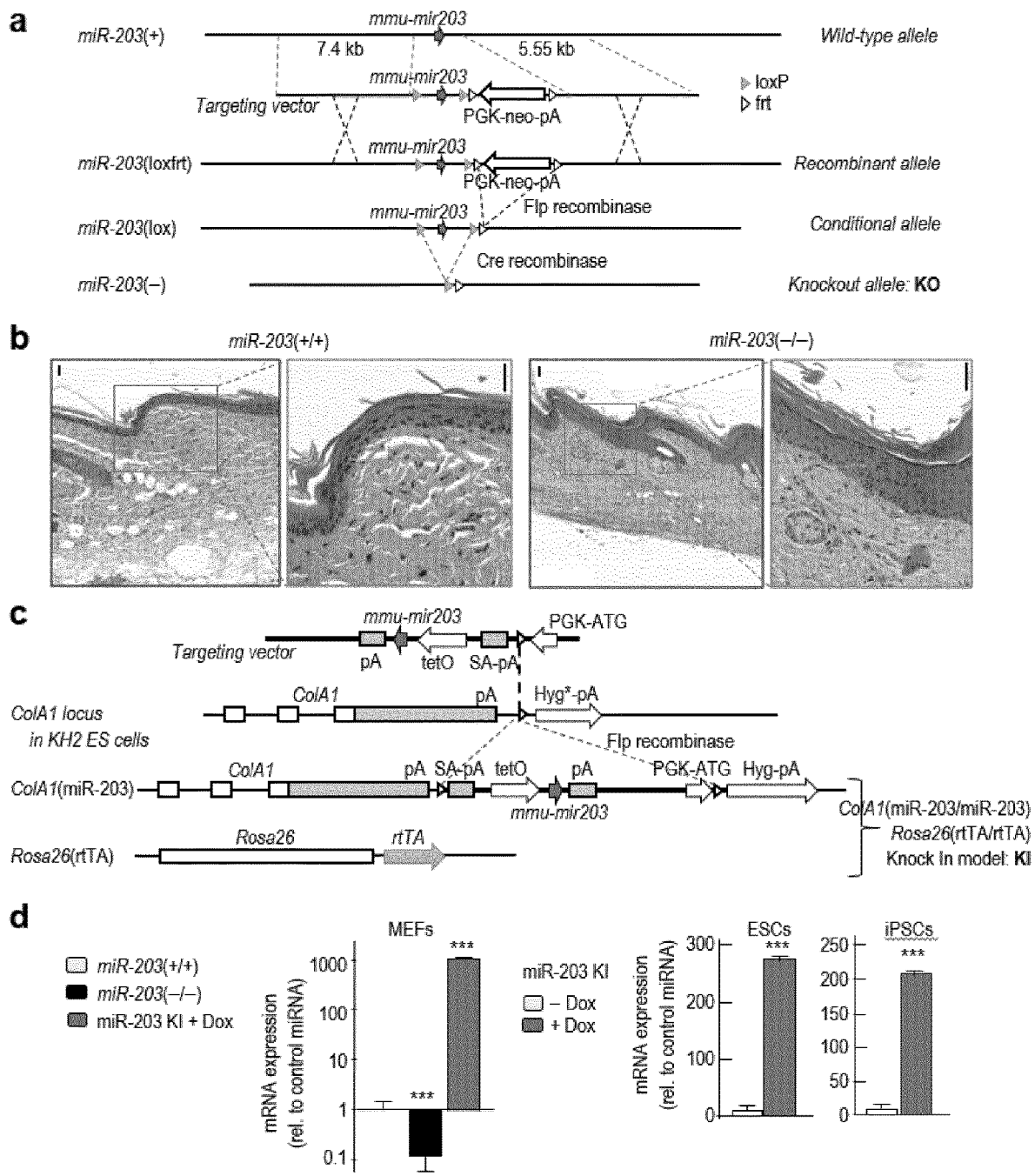
FIG. 1. Mouse alleles generated for the assays. a, Schematic representation of the different alleles generated at the mouse mu-miR203 locus for this application. b, Representative micrographs showing underdeveloped tail skin in miR-203(−/−) mice. Hematoxylin and eosin staining; Scale bars, 50 μm. c, Schematic representation of the miR-203 inducible knockin model generated in this work. In the miR-203 KI [ColA1(miR-203/miR-203); Rosa26(rtTA/rtTA)] model, the reverse tetracycline transactivator is expressed from the Rosa26 locus, whereas miR-203 is driven by the tetracycline operator downstream of the ColA1 locus. d, miR-203 RNA expression, as determined by quantitative PCR, in miR-203 WT, KO and KI (after induction with doxycycline; Dox) MEFs (left panel), or miR-203 KI ESCs and iPSCs treated or not with doxycycline (right panel). RNA expression is normalized by a control miRNA (miR-142). ***P<0.001 (Student's t-test).

The assays of the Examples set forth below were performed with the following materials and methodologies:

Animal Models and Procedures.

miR-203 conditional knockout model was generated by flanking the mmu-mir203 locus with loxP sites (ET recombination; Genebridges, Heidelberg, Germany) using homologous recombination into ES cells (FIG. 1a). A neo-mycin-resistant cassette was used for selection of recombinant clones. Recombination of frt sites was achieved using CAG-Flpe transgenics (Rodriguez et al., 2000) and loxP sites were recombined using a EIIa-Cre transgene (Schwenk et al., 1995) resulting in the miR-203(−/−) allele (FIG. 1a). The miR-203 inducible model was generated by cloning a genomic mmu-mir203 sequence (chr12: 112130880-112130955; miRBase Database release 21.0.) into the pBS31 vector for recombination into the ColA1 locus in ES cells following the strategy reported previously (Beard et al., 2006). The resulting knockin allele [ColA1(miR-203)] was combined with a Rosa26-M2rtTA allele [Rosa26(rtTA)] for doxycycline-dependent induction as described previously (Beard et al., 2006) (see FIG. 1c for details). These animals were maintained in a mixed C57BL6/J×129×CD1 genetic background.

Animal experimentation was performed according to protocols approved by the CNIO-ISCIII Ethics Committee for Research and Animal Welfare (CEIyBA).

For subcutaneous teratomas, iPSCs were trypsinized and 2-3 million cells were suspended in 100 μl PBS supplemented with 0.1% glucose and were subcutaneously injected into both flanks of athymic nude mice Crl:NU(NCr)-Foxn1nu (provided by Charles River). Teratomas were daily controlled and measured by a caliper and finally isolated when their diameters reached 1.5 cm. Animals were euthanized at that point and teratomas were weighted and processed for RNA extraction or histopathological analysis.

For intraperitoneal injections, wild-type athymic mice were injected with 4-5×$10^5$ iPSCs resuspended in 100 μl PBS supplemented with 0.1% glucose. Mice were supervised daily from the day of the injection. Usually, 30 or 40 days after injection mice were euthanized and the visceral teratomas and embryo-like structures were isolated and processed, either for RNA extraction or histopathological analysis.

For chimera generation, iPSCs or ESCs (5-7 cells per embryo, 10 passages) were microinjected into C57BL/6J-Tyrc-2J/J blastocysts and transferred to Crl:CD1 (ICR) pseudo-pregnant females.

For tetraploid complementation studies, zygotes were cultured overnight until they reached the 2-cell stage, or 2-cell stage Hsd:ICR(CD-1) embryos were harvested from pregnant females at E1.5 and electrofused, at which point they were electrofused in 0.3 M mannitol using a BLS CF-150/B cell fusion instrument with a 250 μm electrode chamber. The electric pulse conditions were 30 V amplitude, 31 μs width and 1.5 AC voltage. One hour later, 1-cell (tetraploid) embryos were carefully identified and separated from embryos that had failed to fuse, cultured in KSOM for another 1 or 2 days. Next day, 4-cell stage embryos were selected and aggregated with ESC or iPSCs. Aggregated embryos were then injected to pseudo-pregnant females 24 hours later.

To study the contribution to germline, black ES-iPS mice (from tetraploid complementation assays) or chimeras (from diploid embryo Es-iPS microinjection) were crossed with Albino B6 or C57BL/6J-Tyrc-2J/J females and the color of the progeny was tested.

Cell Culture and Gene Expression.

Primary mouse embryonic fibroblasts (MEFs) were obtained from embryos at E13.5 and cultured in DMEM supplemented with 10% of FBS and Penicillin/Streptomycin. Cultures were routinely tested for mycoplasma. Reprogramming was induced on these MEF cultures by Oct4-Sox2-Klf4-cMyc (OSKM) lentiviral transduction (Takahasi & Yamanaka, 2006). For lentiviral transduction, HEK293T cell were transfected with Tet-O-FUW-OSKM (Addgene #20321) and packaging vectors using Lipofectamine 2000 (Invitrogen). Viral supernatants were collected twice a day on two consecutive days starting 24 h after transfection and were used to infect MEFs, previously plated at a density of 250000 cells per well in 6-well plates. Previous to infection, polybrene was added to the viral supernatants at a concentration of 2 µg/ml. Infected MEFs were then cultured in IPSCs medium, containing KO-DMEM (Gibco), 2-Mercaptoethanol 50 mM (Invitrogen), non-essential aminoacids MEM NEAA (Invitrogen), Penicillin and Streptomycin (5000 µg/ml, Invitrogen), LIF (Leukemia Inhibitor Factor, ESGRO, Millipore) and 20% knock-out serum replacement (KSR, Invitrogen). Medium was changed every 24 h and plates were stained for alkaline phosphatase activity to assure the efficiency of reprogramming (AP detection kit, Sigma-Aldrich). Once colonies were picked, IPSCs were cultured in IPSCs media over mitomycin C (Roche) inactivated feeder cells. G4 ESCs were cultured over mitomycin C-inactivated feeders and in the presence of ESCs medium containing KO-DMEM, 2-Mercaptoethanol, non-essential aminoacids, Glutamax, Penicillin and Streptomycin, LIF and 10% Fetal Calf Serum (Hyclone). When indicated, the culture media for pluripotent cells included 2i factors (MEK inhibitor PD0325901 1 µM, Gsk3 inhibitor CHIR99021 3 µM) and mouse LIF (as above) in N2B27 medium, as described previously (Ying et al., 2008).

For inducing transient miR-203 over-expression in miR-203 KI cells, (ColA1(miR-203/miR-203), Rosa26(rtTA/rt/TA) iPSCs or ESCs cultures were treated with doxycycline (1 µg/ml; Invitrogen) during 5 days. After that, doxycycline withdrawal was standardized for the cultures during following several passages (15-30 days). Doxycycline treatment was also applied to wild-type ESCs or iPSCs to evaluate the effect of the treatment itself.

For over-expression experiments, miR-203 and full-length cDNAs of Dnmt3a and Dnmt3b were subcloned into the retroviral vector pMCSV-PIG (Available through Addgene plasmid 21654: https://www.addgene.org/21654/) (Abad et al., 2013) by restriction-directed subcloning, using pCMV-Sport6-mDnmt3a (MGC clone:5662) and attB-mCh-mDnmt3b-Poly (A)-NeoR (Addgene plasmid 65553) plasmids as templates, respectively. When transduced with these retroviral vectors, both ESCs and iPSCs cells were sorted by FACS and GFP-positive cells were selected for subsequent cultures and analysis.

For retroviral transduction, we transfected HEK293T cells with the respective pMCSV-PIG vector (Abad et al, Nature 2013) expressing a GFP reporter (including either only GFP; miR-203-GFP; Dnmt3a-GFP or Dnmt3b-GFP) and the packaging vector pCL-ECO, using Lipofectamine 2000 (Invitrogen). Viral supernatants were collected twice a day on two consecutive days starting 24 h after transfection and were used to infect either ESCs or IPSCs, previously plated over feeders in 6-well plates. Preceding the infection, polybrene was added to the viral supernatants at a concentration of 2 µg/ml.

For transfection with mimics, the present inventors used miRIDIAN microRNA human hsa-miR-203a-5p (C-302893-00)/hsa-miR-203a-3p (C-300562-03) mimics or mimic transfection control with Dy547 (CP-004500-01), from Dharmacon, so that the cells were subjected to a mixture of analogues/mimics of both mature forms of microRNA-203, just to mimic faithfully the endogenous scenario in the cells. Transfection was performed using either Dharmafect transfection reagent (Dharmacon) or Lipofectamine RNAiMAX (Invitrogen) following the manufacturer's instructions. Transfection efficiency was evaluated 24 hours post-transfection by Dy547 fluorescence, and experiments were then performed as indicated in the figures.

For RNA interference assays, ON-TARGETplus SMART-pool for Non-targeting control siRNA (D-001810-01, 02, 03, 04), Dnmt3a siRNAs (J-065433-09, 10,11, 12) and Dnmt3b siRNAs (J-044164-05, 06, 07, 08) from Dharmacon were used. Transfection was performed using Darmafect transfection reagent (Dharmacon) following the manufacturer's instructions. Transfection efficiency was evaluated 24 hours post-transfection by pPCR, using the primers indicated in Table 2.

Luciferase reported assays were performed in HEK293T cells. Briefly, 200.000 cells per well were seeded on 6-well plates and the day after, cells were transfected using Lipofectamine 2000 (Invitrogen), following the manufacturer's instructions. The 3'UTR regions from the murine genes Dnmt3a, Dnmt3b, Dnmt3l and Dnmt1 were amplified by PCR with specific primers (Dnmt3a_EcoRI-Fw: 5'-GAATTCAGGGACATGGGGGCAAACTGAA-3' (SEQ ID NO:55); Dnmt3a_NdeI-Rv: 5'-CATATGCTGAGGCAGTCATTTTAGATTCAT-3' (SEQ ID NO:56); Dnmt3b_EcoRI-Fw: 5'-GAATTCTTTTAGCTCACCTGTGTGGGG-3' (SEQ ID NO:57); Dnmt3b_NdeI-Rv: 5'-CATATGCCAGAAAGGTAAACTCTGGGCA-3' (SEQ ID NO:58); Dnmt3l_EcoRI-Fw: 5'-GAATTCGAAATGAATCACCATAAGATGAAAG-3' (SEQ ID NO:59); Dnmt3_NdeI-Rv: 5'-CATATGAACAATCCTATGATATATTTGAAAAA-3' (SEQ ID NO:60); Dnmt1 EcoRI-Fw: 5'-GAATTCGTGCTCTCACCCAGAGCCCCA-3' (SEQ ID NO:61); Dnmt1 NdeI-Rv: 5'-CATATGGCTTGACAGAAGCGCTTTATTTTG-3') (SEQ ID NO:62) using cDNA clones (pCMV-Sport6-mDnmt3a, cDNA clone MGC:5662; pBluescript-mDnmt3l, RIKEN clone: 2410006021; pYX-Asc-mDnmt1, MGC clone:62302) or mouse cDNA (in the case of Dnmt3b). PCR products were verified by sequencing and ligated into the pGL3-Control vector (Promega), downstream of the luciferase reporter gene. Mutations in the miR-203 binding sites (FIG. 10) were generated by site-directed mutagenesis and subsequently verified by sequencing. Transfections were performed with either pMCSV-GFP or pMCSV-miR-203-GFP vectors, in combination with the pGL3-derived vectors, and Renilla as a control. Luciferase measurement was achieved 48 hours post-transfection using a luminescence microplate reader (Biotek). Finally, the ES cells expressing the 2C::tdTomato reporter to detect endogenous expression of the 2C-stage-retrotransposon MuERV-L were cultured in 2i media over feeders as reported previously (Macfarlan et al., 2012). This retrotransposon is specifically induced in totipotent 2-cell blastomeres. MERVL expression can be rarely detected in pluripotent stem cells in culture, but only at very low proportions (less than 0.5% of the culture).

Human iPSCs expressing the long terminal repeat (LTR7) of HERVH endogenous retroviruses fused with GFP reporter (Wang et al., 2016) were cultured in mTeSRTM1 media (Stem Cell Technologies) over a Matrigel basement (Corning). Experimentation with human cells was performed according to protocols approved by the ISCIII Ethics Committee for Research (CEI; number PI 61_2017).

Embryoid Body Generation.

Briefly, when wild type iPSCs or ESCs were used, they were previously transduced with retroviruses expressing miR-203 (pMSCV-miR-203) or transfected with miRNA mimics for transient expression of miR-203, as can be seen in the schematic representation of FIG. 4a. iPSCs or ESCs were trypsinized and resuspended to a concentration of 200.000 cells/ml in the presence of complete growth medium lacking leukemia inhibitory factor (LIF). Small drops of this suspension (~25 µl) were collected and seeded on the lid of a 10 mm plate, generating hanging drops of approximately 5000 cells per drop. After 4 days, the aggregates were already visible at the bottom of the drops and were picked and transferred to a non-adherent plate, containing DMEM and 10% Fetal Calf Serum. There they were maintained in suspension for the indicated times and beating, size and cavity formation were assessed as described in the figures. Briefly, embryoid bodies were observed every five days and measured for size, beating and cavity formation. Between 20 and 30 EBs were analyzed per condition and the percentages of "EBs beating" or "EBs with cavities" were calculated for every time point. The EBs size was measured using the Image J software.

Immunofluorescence and Immunohistochemistry.

Cells previously seeded in cover slips were fixed in 4% paraformaldehyde for 15 min, permeabilized using PBS 0.1% Triton X-100 for 15 min and blocked in BSA for 1 h at room temperature. Primary antibody incubation was performed overnight at 4° C. in all cases, followed by secondary antibody incubation for 1 hour at room temperature. Nuclear staining was included in the last PBS wash, using Hoescht or DAPI. Primary antibodies used in this study were against Cd34 (Abcam), Gata4 (Santa Cruz), Pax6 (Abcam), Nestin (Millipore), cTnT (Abcam) and phospho-histone H3 (Millipore). Table 1 below shows detailed information about said antibodies and other antibodies used in the assays of the present application. Cells were examined under a Leica SP5 microscope equipped with white light laser and hybrid detection.

For immunohistochemistry, tissue samples were fixed in 10% formalin, paraffin-embedded and cut in 3-µm sections, which were mounted in super-frost-plus porta-objects and rehydrated. Consecutive sections were stained with hematoxylin and eosin (H&E) or subjected to immunohistochemistry using automated immunostaining platforms (Ventana Discovery XT, Roche or Autostainer Plus Link 48). Antigen retrieval was first performed with high or low pH buffer depending on the primary antibody (CC1m, Roche or low pH antigen retrieval buffer, Dako), endogenous peroxidase was blocked (peroxide hydrogen at 3%) and slides were incubated with primary antibodies against Nanog (Cell Signalling Biotechnology, 8822), cytokeratin 8 (CK8; CNIO Monoclonal Antibodies Core Unit, AM-TROMA I), GFP (Roche, 11814460001), Sox2 (Cell Signaling Technology, 3728), alpha-fetoprotein (AFP; R&D Systems, AF5369), Oct4 (Santa Cruz Biotechnology, sc-9081), KI-67 (Master Diagnostica, 0003110QD), Nestin (Millipore MAB353), Cd31 (Abcam), Cd34 (ABCAM ab8158), Cd73 (Cell Signaling Technology), Collagenase Type I (Rockland), Gata4 (Santa Cruz Biotechnology, sc-1237), Insulin (Dako A0564), Smooth muscle actin (Thermo Scientific RB-9010-PO), skeletal actin (Dako, M0635), and Ter119 (LY-76; BD Bioscience, 550565) were used. Detailed information about them can be also found in Table 1 below. Slides were then incubated with the corresponding secondary antibodies conjugated with horseradish peroxidase (OmniRabbit Ventana, Roche) and the immunohistochemical reaction was developed using 3,30-diaminovenzidine tetrahydrochloride (DAB) as a chromogen (Chromomap DAB, Ventana, Roche or DAB solution, Dako) and nuclei were counterstained with Carazzi's hematoxylin. Finally, the slides were dehydrated, cleared and mounted with a permanent mounting medium for microscopic evaluation. For Sims red staining, Weigert's Hematoxylin was incubated for 8 min and Picro/Sirius Red for 1 h, followed by a wash (10 min) with water. The images were acquired with a slide scanner (AxioScan Z1, Zeiss). Sirius red staining was measured using both bright-field and polarized lights. Images were captured and quantified using the Zen Software (Zeiss).

TABLE 1

Antibodies used in the assays of the present application

| Antigen | Catalog Number | Clone number | Source Ig | Source |
|---|---|---|---|---|
| AFP | AF5369 | — | goat | R&D Systems |
| Cd31 | AF28364 | — | rabbit | Abcam |
| Cd34 | Ab8158 | MEC14.7 | rat | Abcam |
| Cd73 | 13160 | D7F9A | rabbit | Cell Signaling Technology |
| CK8 | AM-TROMA I | — | mouse | CNIO Monoclonal Antibodies Core Unit |
| Collagenase type I | 600-401-103S | — | rabbit | Rockland |
| Gata4 (C-20) | Sc-1237 | — | goat | Santa Cruz Biotechnology |
| GFP | 11 814 460 001 | 7.1 + 13.1 | mouse | Roche |
| Histone 3 (phospho-Ser10) | 06-570 | — | rabbit | Millipore |
| Insulin | A0564 | — | Guinea pig | Dako |
| Ki67 | 0003110QD | SP6 | rabbit | Master Diagnostics |
| Nestin | MAB353 | RAT401 | mouse | Millipore |
| Nanog | 8822 | D2A3 | rabbit | Cell Signaling Technology |
| Oct4 | Ab19857 | — | rabbit | Abcam |
| Pax6 | Ab5790 | — | rabbit | Abcam |
| Skeletal muscle actin | M0635 | HHF35 | mouse | Dako |
| Smooth muscle actin | RB-9010-PO | — | rabbit | Thermo Scientific |
| Sox2 | 3728 | C70B1 | rabbit | Cell Signaling Technology |
| Ter119 (LY-76) | 550565 | Ter119 | rat | BD Bioscience |
| Troponin T | Ab8295 | 1C11 | mouse | Abcam |

Analysis of mRNA and microRNA Levels.

RNA was extracted from cell or tissue samples with Trizol (Invitrogen) or by using the miRVana miRNA isolation kit (Thermo Fisher), following the manufacturer's recommendations. Retrotranscription into cDNA was performed using M-MLV Reverse Transcriptase (Promega) following the manufacturer's protocol. Quantitative real time PCR was performed using Syber Green Power PCR Master Mix (Applied Biosystems) in an ABI PRISM 7700 Thermocycler (Applied Biosystems). The housekeeping gene Gapdh was used for normalization. The oligonucleotide primers used in the assays of the present application are listed in the Table 2 below.

TABLE 2

Oligonucleotides used as primers

| Gene | Forward Oligonucleotide (5'-3') | SEQ ID No | Reverse Oligonucleotide (5'-3') | SEQ ID No |
|---|---|---|---|---|
| qRT-PCR (mouse genes) | | | | |
| Dazl | ggttttaccacccgaactctg | 5 | tgtggttgctgatgaagactg | 6 |
| Dnmt1 | cagagactcccgaggacaga | 7 | tttacgtgtcgtttttcgtctc | 8 |
| Dnmt3a | aaacggaaacgggatgagt | 9 | actgcaattaccttggattct | 10 |
| Dnmt3a2 | gggcaaactgaagtagtgatga | 11 | ttacacggcacctgctga | 12 |
| Dnmt3b | ccctcccccatccatagt | 13 | tctgctgtctccatcattgt | 14 |
| Dnmt3l | aagtgaaccgacggagcat | 15 | ccgagtgtacacctggagagtt | 16 |
| Ecat1 | tgtggggccctgaaaggcgagctgagat | 63 | atgggccgccatacgacgacgctcaact | 64 |
| Eras | actgcccctcatcagactgctact | 65 | cactgccagtactcgggtagctg | 66 |
| Esg1 | gaagtctggttccttggcaggatg | 67 | actcgatacactggcctagc | 68 |
| Fgf4 | cgtggtgagcatcttcggagtgg | 69 | ccttcaggtccgcccgttctta | 70 |
| Gapdh | aggtcggtgtgaacggatttg | 25 | tgtagaccatgtagttgaggtca | 26 |
| Gata6 | accttatggcgtagaaatgctgagggtg | 27 | ctgaatacttgaggtcactgactcggg | 28 |
| Gdf3 | gttccaacctgtgcctcgcgtat | 71 | agcgaggcatggagagagcggagcag | 72 |
| Hcn1 | tgaagctgacagatggctat | 31 | ctggcagtacgacgtcctttt | 32 |
| Isl1 | ttgtacgggatcaaatgcgccaag | 33 | aggccacacagcggaaaca | 34 |
| Kcna4 | tcattgctctgacctgatgc | 35 | tcactcagctccctcaggat | 36 |
| Kcnh2 | acgcttactgccagggtgac | 37 | gccgactggcaaccagag | 38 |
| Myh | ctcaagctcatggccactct | 39 | gcctcctagctataccact | 40 |
| Nanog | caggtgtttgagggtagctc | 41 | cggttcatcatggtacagtc | 42 |
| Nppa | gaaccagaggggagagacagag | 43 | ccctcagcttgcttttttaggag | 44 |
| Tbx5 | aaatgaaacccagcataggagctggc | 45 | acactcagcctcacatcttaccct | 46 |
| Tnnt2 | ggcagcggaagaggatgctgaa | 47 | gaggcaccaagttgggcatgaacga | 48 |
| qrt-pcr (rat genes) | | | | |
| Ccnb1 | ggagatgaagattctgagagttctg | 73 | gtatgctgctccacatcgac | 74 |
| Gapdh | ggcaagttcaatggcacagt | 75 | tggtgaagacgccagtagactc | 76 |
| Myh6 | gggctggagcactgagag | 77 | gagagaggaacaggcaggaa | 78 |
| Myh7 | atggcggatcgagagatg | 79 | ggtcaaagggcctggtct | 80 |
| dna methylation analysis (mouse genes) | | | | |
| Elf5 (a) | taaaggttgtaatgaatagatattaggtt | 81 | aactacttacttaaaaacaaataataactaaa | 82 |
| Elf5 (b) | taaaggttgtaatgaatagatattaggtt | 83 | aaataataactaaatccaaacaaaaaa | 84 |
| Sirt6 | tttggttttttttaggttatgttaggattt | 85 | cacttacctctacctcccaataaaaaa | 86 |

For reverse transcription of microRNAs, the Taqman small RNA assay (ThermoFisher Scientific, 4366596) was used, including the specific commercial oligonucleotides for mmu-miR-203-5p and 3p (ThermoFisher Scientific, 002580 and 000507) and the housekeeping RNAs sno-202 or sno-142 (ThermoFisher Scientific). Conditions for miRNA amplification were as follows: 30 minutes at 16° C.; 30 minutes at 42° C. and a final step of 5 minutes at 85° C. Quantitative real time PCR was then performed using the Taqman Universal PCR Master Mix (434437) following the manufacturer's instructions in an ABI PRISM 7700 Thermocycler (Applied Biosystems).

For RNAseq, total RNA was extracted using the miRVana miRNA isolation kit (ThermoFisher), following the manufacturer's recommendations. Between 0.8 and 1 μg of total RNA was extracted from iPSCs, ESCs or teratomas, with RIN (RNA integrity number) numbers in the range 7 to 10 (Agilent 2100 Bioanalyzer). Poly A+ fractions were purified and randomly fragmented, converted to double stranded cDNA and processed using the Illumina's "TruSeq Stranded mRNA Sample Preparation Part #15031047 Rev. D" kit. The adapter-ligated library was completed by PCR with Illumina PE primers (8-11 cycles) and the resulting directional cDNA libraries were sequenced for 50 bases in a single-read format (Illumina HiSeq2000) and analyzed with nextpresso (available at http://bioinfo.cnio.es/nextpresso/) (Graña et al., 2017). Reads were quality-checked with FastQC (http://www.bioinformatics.babraham.ac.uk/projects/fastqc) and aligned to the mouse genome (GRCm38/mm10) with TopHat-2.0.10 (available at https://ccb.jhu.edu/software/tophat/) (Trapnell et al., 2012), using Bowtie 1.0.0 (downloadable from different Internet resources, such as https://slackbuilds.org/repository/14.2/academic/bowtie/) (Langmead et al., 2009) and Samtools 0.1.19 (https://sourceforge.net/projects/samtools/files/samtools/0.1.19/) (Li et al., 2009), allowing two mismatches and five multihits. Transcripts assembly, estimation of their abundances and differential expression were calculated with Cufflinks 2.2.1 (available at http://cole-trapnell-lab.github.io/cufflinks/releases/v2.2.1/) (Trapnell et al., 2012), using the mouse genome annotation data set GRCm38/mm10 from the UCSC Genome Browser (https://genome.ucsc.edu/) (Rosenbloom et al., 2015). A false discovery rate (FDR) of 0.05 is used as threshold for significance in differential expression. Heatmaps were later built using GENE-E (http://www.broadinstitute.org/cancer/software/GENE-E/index.html). RNAseq data have been deposited in the GEO repository (accession number GSE81571).

Bisulphite Conversion, Genome-Wide DNA Methylation and Validation of DMRs.

DNA samples were prepared for whole genome bisulphite sequencing using the TrueMethyl® Whole Genome Kit (CEGX®) according to the manufacturer's instructions. Briefly, 200 ng of genomic DNA was sheared to 800 bp using M220 Focused-Ultrasonicator™ (Covaris®). Then the fragmented DNA was denatured and oxidised by a chemical oxidant to convert 5-hydroxymethyl cytosine to 5-formylcytosine (5fC). The purpose of the oxidation was to ensure that we purely captured the information for 5' methyl cytosine methylation and not an indistinguishable pattern combination of 5'methyl cytosine and 5'hydroxymethyl cytosine. Following oxidation, the DNA was subjected to bisulphite conversion for the deamination of cytosines and 5fC to uracils. Bisulphite converted DNA was desulfonated and purified to then proceed to library preparation. In this "post-bisulphite conversion" library preparation method, the fragmented single stranded bisulphite converted DNA was adapted with sequencing adaptors at the 3'end followed by an extension step and finally ligation of adaptors at the 5' end of the molecules. Finally, the libraries were indexed and amplified. The PCR was performed for 10 cycles followed by bead-based purification. An additional purification and size selection step using Agencourt AMPure XP beads (Beckman Coulter, Cat: A63881) was performed to remove adaptor dimers. The purified library was eluted in a final volume of 14 µl pure water. Quality of the library obtained was checked using the DNA High sensitivity chip on the Agilent Bioanalyzer. The library was quantified using Qubit and KAPA Biosystems Library quantification kit (#KK4824) according to manufacturer's instructions. A total of 1 2 pMol of multiplexed libraries were loaded on a 125 bp PE rapid run on Illumina HiSeq2500. Adapter sequences were removed using cutadapt version 1.9.1 (Martin, 2011) in paired-end mode with parameters "-m 15 -u 6 -U 6". Bwa-meth (Pedersen et al., 2014) was then used to align reads to mm10 using default parameters. PCR duplicates were removed using Picard v1.91 (http://broadinstitute.github.io/picard). Count tables of the number of methylated and unmethylated bases sequenced at each CpG site in the genome were constructed using the "tabulate" module of bwa-meth and BisSNP-0.82.2 (Liu et al., 2012) with default parameters. All libraries passed basic quality control checks with a minimum of 82.7% of read pairs aligning uniquely. DMRs were called using the WGBS module of DMRcate (Peters et al., 2015) with parameters lambda=1000 and C=50, DMPs were called using DSS(Feng et al., 2014), PMDs, LMRs and UMRs were called using MethylSeekR (Burger et al., 2013) and PMDs were called using the R package 'aaRon' (https://github.com/astatham/aaRon).

For the validation of DMRs, clonal bisulphite sequencing was performed at two particular loci: Elf5 (chr2: 103, 423, 778-103, 424, 180) and Sirt6 (chr10: 81, 624, 595-81, 625, 547) promoter regions (Genome Browser: Mouse mm10 Dec. 2011. Genome Reference Consortium GRCm38). 100 ng of DNA was bisulphite treated using EZ DNA-Methylation-Lighting™ kit (Zymo Research) following manufacturer's instructions. Bisulphite converted DNA was then analyzed by bisulphite PCR analysis. Triplicate PCR amplifications were performed using semi-nested bisulphite conversion specific primers listed in the last part of Table 2 ("DNA methylation analysis (mouse genes)"), following the PCR conditions previously described for Elf5 (Lee et al., 2011) or using the following protocol: 95° C. 4 min; 5 cycles (95° C. 45 sec, 54° C. 1.5 min, 72° C. 2 min); 25 cycles (95° C. 45 sec, 54° C. 1.5 min; 72° C. 1.5 min) and final extension at 72° C. 4 min, for Sirt6. The methylation status of the PCR amplicons was determined by Sanger clonal sequencing of the pooled PCR products to ensure representative clonal analysis using between 8-10 clones per sample. The analysis of the methylation status of the clones was performed using BiQ Analyzer (Bock et al., 2005).

Neonatal Cardiomyocyte Isolation and Differentiation Studies.

Neonatal mouse and rat cardiomyocytes were prepared as described previously (Huang et al., 2015). Briefly, neonatal cardiomyocytes were isolated by enzymatic disassociation of 1-day-old neonatal mouse or rat hearts with the Neonatal Cardiomyocyte Isolation System (Cellutron Life Technology). Cardiomyocytes were pre-plated for 2 hours to remove fibroblasts. Cells were then plated on 1% gelatin-coated plates in medium containing 10% horse serum and 5% fetal calf serum. Eighteen hours after plating, cells were changed into serum-free medium and then transfected with 50 nM miR-203a-3p & miR-203a-5p mimics or control mimics (all of them from Dharmacon) by using Lipofectamine RNAiMAX transfection reagent, following the manufacturer's instructions. Six hours later, media with transfection reagent were removed and substituted by media containing 1% serum. Different time points (as indicated in FIG. 13a: 1, 3 or 5 days after transfection) were collected for subsequent RNA extraction and EdU staining/immunofluorescence. For EdU staining, we used the Click-iT EdU staining Kit (Invitrogen) following the manufacturer's recommendations. After that, immunofluorescence of cardiomyocytes markers (Troponin T) was performed and Hoescht was finally used for nuclei staining.

For in vitro differentiation from mouse iPSCs to cardiomyocytes, wild-type mouse iPSCs were transfected with either control or miR-203a-3p/-5p mimics prior to differentiation. In some experiments, additionally pMCSV-Dnmt3a and 3b or empty pMCSV vector were transiently transduced, 24 hours after mimics transfection. iPSCs were then maintained in culture under the standard conditions (under 2i/LIF media) for 15 days, before differentiation started. Then, cells were plated in Matrigel pre-coated 6-well plates. Once they become confluent, the media was changed to RPMI 1640/B27 medium (Thermo Fisher Scientific, 61870127 for the RPMI 1640 media and A1895601 for B27) with CHIR99021 5 µM (Stem Cell Technologies, 72054). After two days, cells were washed and media without CHIR99021 was added. At day 3 of differentiation, media was supplemented with IWR1 5 µM (Stem Cell Technologies, 72564) and maintained in these conditions for 2 more days. At day 7 of differentiation, the media was changed to RPMI 1640/B27 plus insulin. Then, from day 9 to day 15, cells were cultured in RPMI 1640/B27 and the media was changed every 2 days. From day 16 to day 18 of differentiation, cells were cultured in DMEM without glucose and with lactate 4 mM. From day 18 to day 21, the media was changed to RPMI 1640/B27 and changed every day. Finally, from day 22 to day 28, monolayer cells can be isolated into cell clusters and kept in low attachment for another week.

Cardiac Cryoinjury in Neonatal Mice

The neonatal mouse cardiac cryoinjury experiments were performed as described previously (Polizzotti et al., 2016). Briefly, at postnatal day 1, neonates were placed on a heated water blanket set to 37° C. and covered with bedding from mother's nest. They were then anesthetized by placing the pups into an ice-water bath for 3 minutes. After that, the pups were dried using a sterile gauze pad and placed in the surgical area in the supine position, immobilized at the arms legs and tail. A transverse skin incision across the chest was made using a pair of micro-scissors and then carefully, a lateral thoracotomy was performed, by making a small incision at the fourth or fifth intercostal space. The pericardial sac was then carefully removed and the heart was exteriorized by gently pressing the abdomen. The left ventricle was identified and then the precooled cryoprobe was applied on the ventricle surface for just 2 seconds. To close the chest wall we used 8-0 Non-absorbable Prolene sutures and to close the skin, we used Webglue sutures. After closure, the surgical area was washed with wet gauzes to remove any residual blood. Rapidly, the pup was warmed for several minutes, returned to the heating blanket with the other pups and covered with bedding from the mother's cage. Once all the pups had fully recovered from the surgery, they were swapped in the mother's cage. Seven days after the cryoinjury, the pups were euthanized by decapitation and the hearts were collected and fixed in formaldehyde. The hearts were then processed normally for paraffin embedding as indicated above.

Statistics.

Normal distribution and equal variance was confirmed before using the Student's t-test (two-tailed, unpaired) to estimate statistical significance. For contingency tables, we used the Fisher's exact test. Statistical analysis was performed using Prism (GraphPad Software, La Jolla, Calif.).

Example 1. miR-203 Enhances the Function of Pluripotent Cells In Vitro

To study miR-203 in vivo, the inventors first generated a conditional knockout mouse model in which the miR-203 encoding gene could be eliminated after expression of Cre recombinase (see FIG. 1a). Genetic ablation of miR-203 in the mouse did not result in major abnormalities although miR-203-null mice [miR-203(−/−); KO] displayed mild developmental defects in the skin (FIG. 1b).

A knockin inducible model (KI: ColA_MiR203; Rosa 26_rtTA) was also generated, where the miR-203-encoding sequence was inserted downstream of the type I collagen gene under the control of the tetracycline-responsive sequences [ColA1(miR-203/miR-203)] in the presence of tetracycline reverse transactivator expressed from the Rosa26 locus [Rosa26(rtTA/rtTA)] (FIG. 1c). Thus, the KI model permits an overexpression of more than 100 fold of miR-203 whenever the animal—or the cells derived from the animal—are exposed to doxycycline treatment.

The first approach was extracting the mouse embryonic fibroblasts (MEFs) from those mice (KO and KI), reprogramming them in vitro using the viral version of the Yamanaka factors and generating miR-203 knock in inducible pluripotent cells (miR-203 KI iPSCs).

Treatment of mouse embryonic fibroblasts (MEFs) isolated from these mice with doxycycline led to a 1000-fold-induction in the levels of miR-203 (FIG. 1d).

Figure 2:
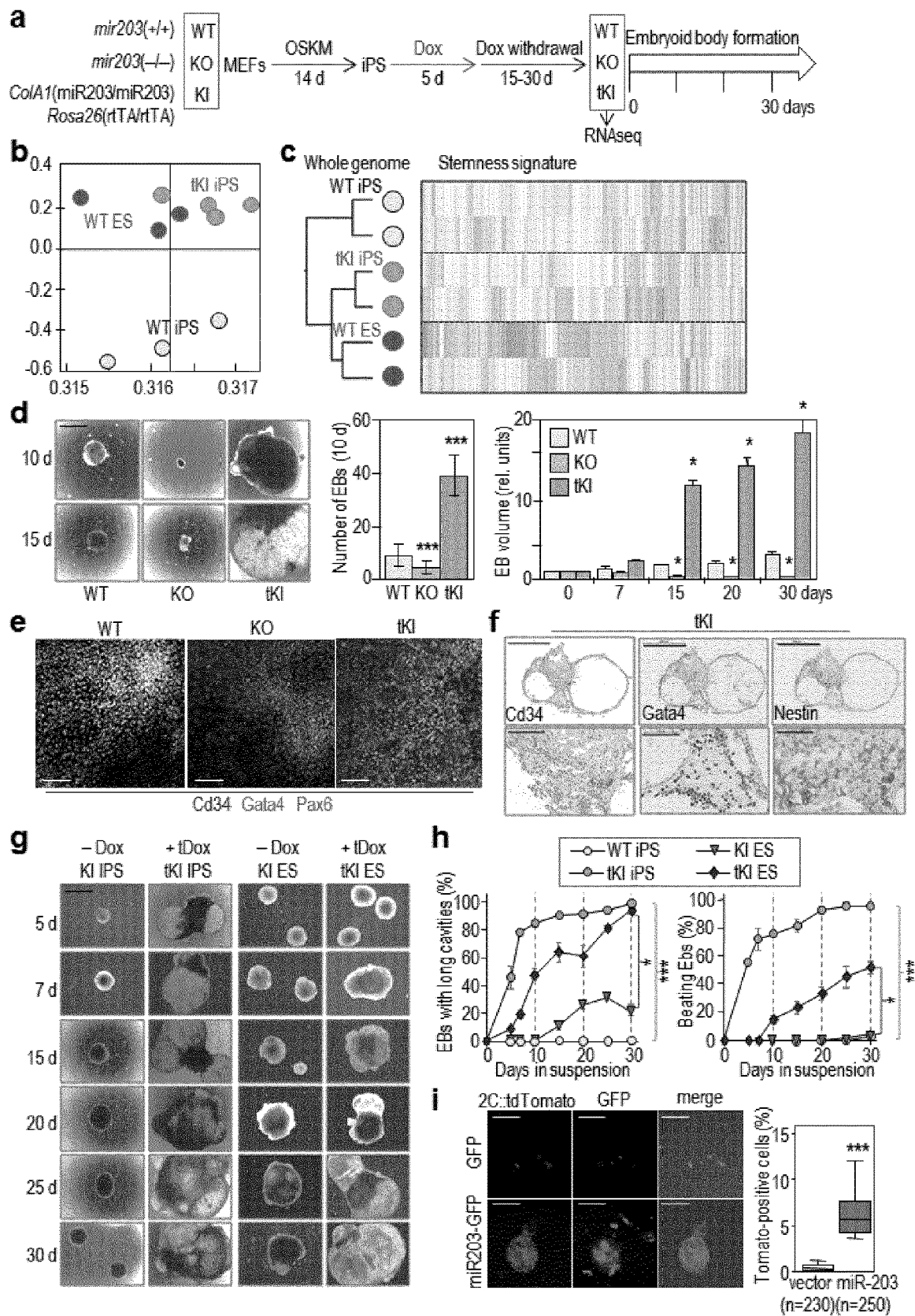
FIG. 2. Effects of transient induction of miR-203 in iPSC and ESC pluripotency and differentiation potential. a, Protocol for reprogramming of miR-203 mutant MEFs into pluripotent iPSCs and subsequent differentiation into embryoid bodies. Wild-type (WT), knockout (KO) and knockin (KI) MEFs were transduced with viruses expressing Oct4, Sox2, Klf4, and c-Myc (OSKM). The resulting iPSCs were then treated with doxycycline (Dox) 1 μg/ml during 5 days. tKI indicates transient miR-203 expression in the knockin cells during the indicated 5 days. Dox was removed for 15-30 days before starting the embryoid body generation protocol. Samples for RNA sequencing were taken 30 days after Dox withdrawal. b, Principal Component Analysis of RNAseq data from WT iPSCs (n=3 clones), tKI iPSCs (n=4) and WT ESCs (n=3). c, Unbiased clustering of genome-wide RNAseq data (left) and heatmap plot showing the comparative expression of 450 genes associated with pluripotency (stemness signature; 2 clones per sample). The profile of tKI iPS is similar to the one observed in ES cells, as the hierarchical tree demonstrates. d, Representative images of embryoid bodies (EBs) derived from WT, KO and tKI iPSCs after 10 or 15 days of differentiation. Scale bars, 500 μm. Middle histogram shows the number of EBs generated from the three genotypes at day 10 of differentiation. Data are mean±s.d. (n=9 independent experiments). The increase in EB size (relative to day 0 of differentiation) is shown in the right panel. Data are represented as mean±s.d. (n=3 independent experiments). e, Representative immunofluorescence detection of Cd34 (mesoderm; green), Gata4 (endoderm; red) and Pax6 (ectoderm; blue) in EBs derived from WT, KO and tKI iPSCs. Scale bar, 20 μm. f, Immunohistochemical detection of Cd34 (mesoderm), Gata4 (endoderm) and Nestin (ectoderm) in tKI EBs. Scale bars are 500 μm for the upper images and 100 m (Cd34, Gata4) or 50 μm (Nestin) for the lower images. g, Representative images of EBs derived from KI iPSCs and ESCs treated with vehicle (KI) or Dox (tKI) at different time points during differentiation. Scale bars, 500 μm. h, Quantification of the percentage of EBs presenting internal long cavities and EBs beating during the indicated time course. Data are represented as mean±s.e.m. (n=3 independent experiments). i, Representative immunofluorescence analysis of ESCs stably expressing the 2C::tdTomato reporter, and transiently transduced with GFP or miR-203-GFP viruses. Scale bar, 10 μm. Right plot shows the percentage of tdTomato-positive cells out of the total GFP-positive cells. Data are represented as mean±s.e.m. (n=3 independent experiments). In d, h and i, *P<0.05; P<0.01; *P<0.001 (Student's t-test).

To directly study the effect of miR-203 expression in pluripotent cells, iPSCs were generated from MEFs isolated from these miR-203 KO and KI models. Wild-type, KO and un-induced KI MEFs were transduced with lentiviral vectors expressing Oct4, Sox2, Klf4 and Myc to generate iPSCs, and KI cultures were later treated with doxycycline (DOX) for 3-5 days, and then exposed to DOX withdrawal for several passages, thus obtaining iPSCs that were named transiently induced KI or, in abbreviated form, tKI iPSCs (see FIG. 2a for a schematic representation of the protocol used).

Although it was previously proposed that miR-203 prevents the stemness potential of skin progenitors (Yi et al., 2008), RNA sequencing of these iPSC clones as well as wild-type ES cells (ESC) unexpectedly revealed that tKI cells were transcriptionally closer to ESCs than WT iPSCs (FIG. 2b), both at the genome-wide level and when considering a naïve pluripotency signature defined previously (Chung et al., 2012) (FIG. 2c).

Figure 3:
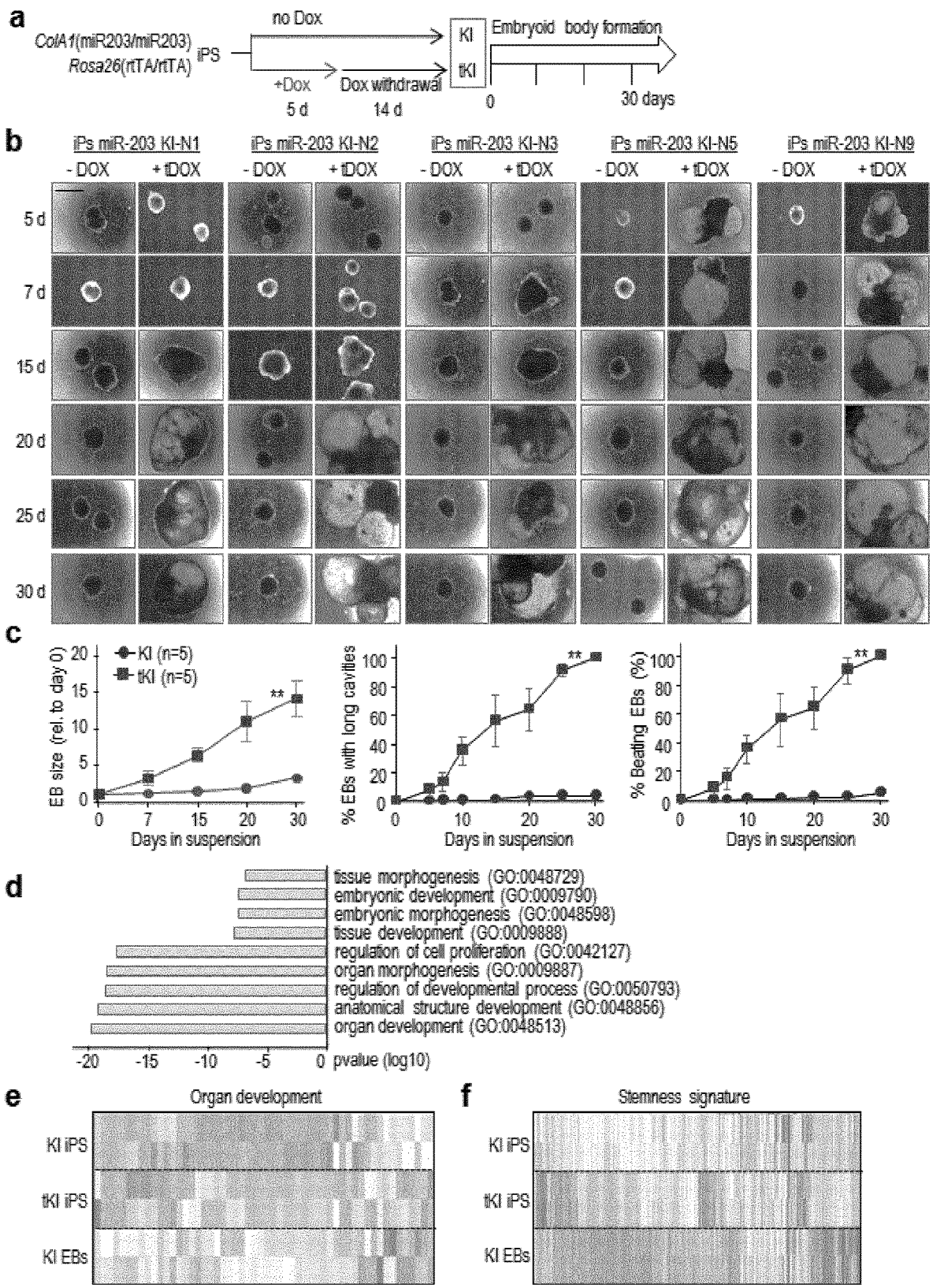
FIG. 3. Improved embryoid body generation after transient genetic induction of miR-203 in iPSCs. a, Experimental design to generate embryoid bodies (EBs) from miR-203 KI iPSCs. Cells were treated or not with doxycycline (Dox) during 5 days and then Dox was removed during the following 2 weeks before starting the embryoid body formation assays. b, Representative images of uninduced (−Dox) or transiently induced (+Dox) EBs derived from five different KI clones at different time points of the differentiation process. Scale bars, 500 μm. c, Quantification of EBs with internal long cavities, beating EBs and EB size during the differentiation process. Data are mean±s.e.m. (n=5 independent experiments). **P<0.01 (Student's t-test). d, Top categories in the Gene Ontology Analysis of the genes significantly upregulated in induced versus uninduced KI iPSCs (4 independent clones were analyzed). e Heatmap showing the expression profile of genes included in GO:0048513 (organ development) in un-induced (KI) or transiently induced (tKI) iPSCs as well as in un-induced embryoid bodies (EBs). The profiles observed for tKI and KI EBs are more similar between them than when compared to control KI iPS. f, Heatmap showing the expression profile of genes included in the stemness signature in the indicated samples. Only the tKI iPS express high levels of the genes included in this signature.

To study the differentiation potential of mutant iPSCs, wild-type and mutant (KO and tKI) iPSCs were tested in the embryoid body formation assay in vitro. It was observed that in vitro differentiation to embryoid bodies (EBs) is significantly increased in tKI compared to control iPSCs and, besides, that tKI iPSC-derived EBs grow faster, differentiate better, show a higher percentage and efficiency at beating and exhibit a perfect architecture of the three germ layers. Thus, whereas lack of miR-203 resulted in deficient formation of embryoid bodies, transient induction of miR-203 for 5 days, 2 weeks prior to this assay, resulted in a significantly higher number and volume of embryoid bodies (FIG. 2d). tKI embryoid bodies displayed a complex organization with high expression of primitive endoderm (Gata4), mesoderm (Cd34) and ectoderm (Pax6) or neuroectoderm (Nestin) markers (FIG. 2e,f). Similar results were found when comparing the very same ColA1(miR-203/miR-203); Rosa26 (rtTA/rtTA) iPS clone untreated (KI) or transiently induced with doxycycline (tKI; FIG. 3a). Also in this case, transient induction of miR-203 resulted in a more efficient formation of larger embryoid bodies with long cavities, and enhanced beating frequency (FIG. 3b,c). A comparison of the expression profiles in tKI versus un-induced KI clones at day 30 after doxycycline withdrawal suggested higher expression of genes related to tissue morphogenesis and embryonic development in those clones in which miR-203 had been transiently induced (FIG. 3d,e). Table 3 shows the Gene Ontology Analysis of genes up-regulated in tKI iPSCs (5 days in the presence of doxycycline and 30 days after doxycycline withdrawal) versus KI iPSCs (untreated).

TABLE 3

Gene Ontology Analysis of genes up-regulated in tKI iPSCs vs. KI iPSCs

| Gene Ontology | log10 (p-value) |
|---|---|
| Anatomical structure development (GO:0048856) | −125.1 |
| Anatomical structure morphogenesis (GO:0009653) | −92.5 |
| Organ development (GO:0048513) | −90.7 |
| Cell differentiation (GO:0030154) | −74.7 |
| Nervous system development (GO:0007399) | −73.0 |
| Organ morphogenesis (GO:0009887) | −64.4 |
| Regulation of cell communication (GO:0010646) | −58.2 |
| Cell adhesion (GO:0007155) | −56.7 |
| Regulation of developmental process (GO:0050793) | −53.3 |
| Cell development (GO:0048468) | −50.3 |
| Cell proliferation (GO:0008283) | −49.4 |
| Tissue development (GO:0009888) | −49.3 |
| Skeletal system development (GO:0001501) | −46.8 |
| Neurogenesis (GO:0022008) | −44.6 |
| Generation of neurons (GO:0048699) | −40.6 |
| Response to wounding (GO:0009611) | −36.0 |
| Neuron differentiation (GO:0030182) | −35.9 |
| Embryonic development (GO:0009790) | −34.3 |
| Positive regulation of metabolic process (GO:0009893) | −34.1 |
| Embryonic morphogenesis (GO:0048598) | −33.7 |
| Cell projection organization (GO:0030030) | −33.0 |
| Cell morphogenesis (GO:0000902) | −32.9 |
| Anatomical structure formation involved in morphogenesis (GO:0048646) | −32.3 |
| Central nervous system development (GO:0007417) | −32.1 |
| Cell morphogenesis involved in differentiation (GO:0000904) | −32.0 |
| Neuron development (GO:(0048666) | −31.7 |
| Cellular component movement (GO:0006928) | −31.1 |
| Vasculature development (GO:0001944) | −31.0 |
| Vesicle-mediated transport (GO:0016192) | −30.7 |
| Cell migration (GO:0016477) | −30.1 |
| Blood vessel development (GO:0001568) | −30.0 |
| Transmission of nerve impulse (GO:0019226) | −29.4 |
| Extracellular matrix organization (GO:0030198) | −29.0 |
| Positive regulation of cell differentiation (GO:0045597) | −27.2 |
| Anterior/posterior pattern formation (GO:0009952) | −25.9 |
| Bone development (GO:0060348) | −25.8 |
| Ossification (GO:0001503) | −25.5 |
| Embryonic skeletal system development (GO:0048706) | −25.0 |
| Blood vessel morphogenesis (GO:0048514) | −24.56 |
| Chordate embryonic development (GO:0043009) | −23.9 |
| Brain development (GO:0007420) | −23.8 |
| Tube development (GO:0035295) | −21.0 |
| Muscle organ development (GO:0007517) | −20.9 |
| Heart development (GO:0007507) | −19.0 |
| Regulation of cell adhesion (GO:0030155) | −18.3 |
| Tissue morphogenesis (GO:0048729) | −17.8 |
| Osteoblast differentiation (GO:0001649) | −17.6 |
| Urogenital system development (GO:0001655) | −17.4 |
| Gland development (GO:0048732) | −17.3 |
| Regulation of cell migration (GO:0030334) | −17.2 |
| Cartilage development (GO:0051216) | −17.0 |
| Kidney development (GO:0001822) | −16.8 |
| Blood circulation (GO:0008015) | −16.7 |
| Respiratory tube development (GO:0030323) | −15.1 |
| Respiratory system development (GO:0060541) | −15.1 |
| Regulation of immune system process (GO:0002682) | −15.0 |
| Lung development (GO:0030324) | −14.6 |
| Aging (GO:0007568) | −13.4 |
| Muscle fiber development (GO:0048747) | −12.6 |
| Metanephros development (GO:0001656) | −12.6 |
| Regulation of striated muscle tissue development (GO:0016202) | −12.4 |
| Branching morphogenesis of a tube (GO:0048754) | −12.1 |
| Muscle cell differentiation (GO:0042692) | −12.1 |
| Morphogenesis of an epithelium (GO:0002009) | −12.1 |
| Mammary gland development (GO:0030879) | −12.1 |
| Tissue remodeling (GO:0048771) | −12.1 |
| Ear development (GO:0043583) | −11.7 |
| Regulation of osteoblast differentiation (GO:0045667) | −11.6 |

TABLE 3-continued

Gene Ontology Analysis of genes up-regulated in tKI iPSCs vs. KI iPSCs

| Gene Ontology | log10 (p-value) |
|---|---|
| Positive regulation of epithelial cell proliferation (GO:0050679) | −11.4 |
| Mesenchymal cell development (GO:0014031) | −10.4 |
| Mesenchymal cell differentiation (GO:0048762) | −10.4 |
| Vasoconstriction (GO:0042310) | −10.0 |
| Regulation of smooth muscle cell proliferation (GO:0048660) | −9.9 |
| Regulation of blood pressure (GO:0008217) | −9.9 |
| Muscle contraction (GO:0006936) | −9.9 |
| Mesoderm formation (GO:0001707) | −8.3 |
| Mesoderm morphogenesis (GO:0048332) | −8.3 |
| Mesoderm development (GO:0007498) | −8.3 |
| Skin development (GO:0043588) | −7.8 |
| Regulation of heart contraction (GO:0008016) | −7.7 |

Interestingly, the upregulation of development and morphogenesis pathways was also accompanied by enhanced expression of pluripotency genes after transient induction of miR-203 in these iPSCs (FIG. 3f).

Figure 4:
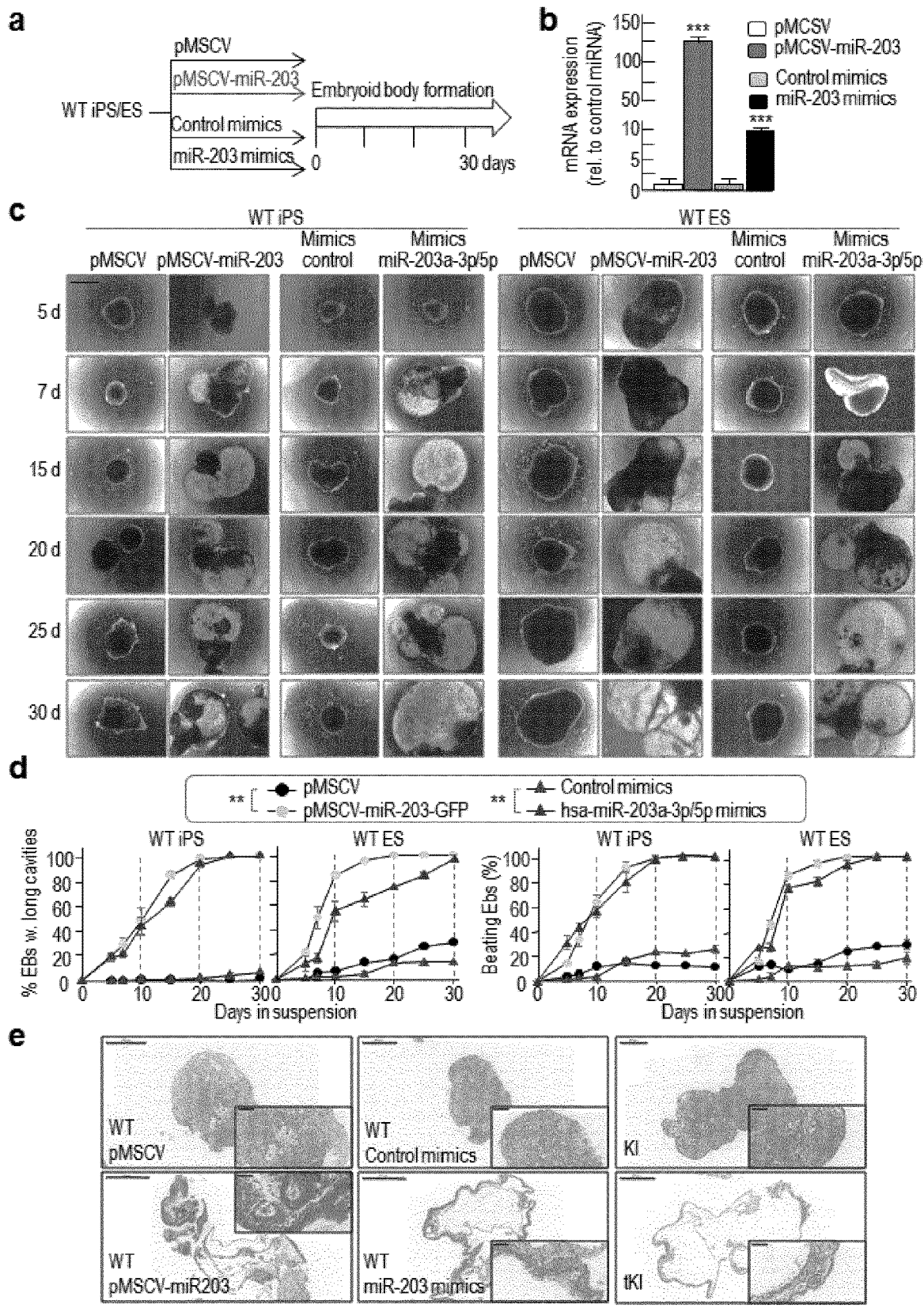
FIG. 4. Improved embryoid body formation after transient exogenous expression of miR-203. a, Schematic representation of the experimental design used to generate embryoid bodies (EBs) from wild-type iPSCs or ESCs, either transduced with retroviruses or transfected with miRNA mimics for transient expression of miR-203. b, miR-203 RNA expression in wild-type iPSCs transduced with pMCSV or pMCSV-miR-203, or transfected with control mimics or miR-203 mimics. RNA expression is normalized by a control miRNA (miR-142). *P<0.001 (Student's t-test). c, Representative images of EBs derived from either wild-type iPSCs (left) or ESCs (right) transduced with empty pMCSV vector, pMCSV-miR-203 or transfected with control mimics or miR-203 mimics, at different time points during the differentiation process. Scale bars, 500 μm. d, Quantification of EBs with long cavities and beating EBs during the differentiation process. Data are mean±s.e.m (n=3 independent experiments). P<0.01 (both in iPS and ES cells; Student's t-test). e, Representative micrographs of EBs generated in the previous protocol. Note the complexity and formation of long cavities in the structures showed in the lower panels. Scale bars, 200 μm (upper panel) and 500 μm (bottom panels) or 50 μm (insets).
Figure 5:
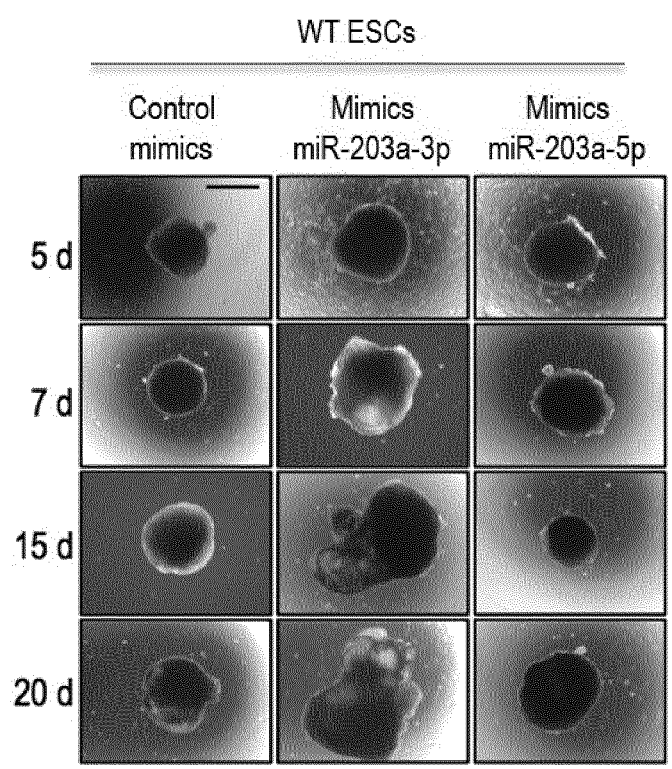
FIG. 5. Improved embryoid body formation after transient exogenous expression of miR-203a-3p versus miR-203a-5p.

The inventors next tested whether miR-203 had a similar effect in ES cells. ES cells were generated from ColA1(miR-203/miR-203); Rosa26(rtTA/rtTA) mice and these cells were left untreated (KI) or treated with doxycycline transiently for 5 days (tKI), 2 weeks before performing the embryoid body assays. As shown in FIG. 2g,h, transient induction of miR-203 in ESCs resulted in larger embryo bodies that showed beating with higher efficiency and at earlier time points that untreated ESCs. Interestingly, transient expression of ectopic miR-203 using a CMV-driven retroviral vector or RNA mimics also resulted in enhanced embryoid body formation in wild-type iPSCs or ESCs (FIG. 4a-e), indicating that these effects were not unique to the inducible genetic model. As depicted in FIG. 4, both miR-203a-3p/-5p were used in these assays, aiming to faithfully mimic the endogenous scenario in which both mature forms are expressed. However, the most abundant form (miR-203a-3p) is responsible for the observed effects in the present invention (FIG. 5). Finally, transient expression of miR-203-GFP in wild-type ES cells significantly increased the number of 2C (2-cell embryo)-like cells as determined by the expression of the murine endogenous retrovirus with leucine tRNA primer (MuERV-L; 2C::tdTomato reporter) (Macfarlan et al., 2012) (FIG. 2i).

Together, these results suggest that transient induction of miR-203 sequences improves pluripotency in iPSCs and ESCs favoring the differentiation of these cells to multiple lineages in vitro.

Example 2. miR-203 Improves Pluripotent Function of iPS Cells In Vivo

It was then tested the potential of tKI iPSCs (in which the expression of miR-203 had only been induced for 5 days in vitro) after subcutaneous injection in mice. And it was found that in vivo differentiation to teratomas is also dramatically improved when tKI IPs are injected in mice when compared with their respective controls.

Whereas the formation of teratomas was reduced in miR-203 KO cells, tKI iPSCs formed significantly bigger tumors in these assays (FIG. 6a). Interestingly, these teratomas were not only bigger, but also the level of differentiation of the three germ layers in them was notorious and they contained tissues that are not typically found in control iPSC-induced teratomas, such as bone marrow, cartilage or pancreas, insulin-positive cells (indicative of pancreatic beta cells) as well as trophoblasts (indicative of extraembryonic tissue, placenta) as confirmed by the expression of PL-1 (FIG. 6b,c and FIG. 7a,d).

Transcriptomic studies in these teratomas suggested upregulation of genes involved in embryonic development and organ morphogenesis when derived from tKI iPSCs (FIG. 7b). Immunohistochemistry studies showed elevated expression of multiple differentiation markers representing ectoderm, mesoderm and endoderm in tKI teratomas (FIG. 6d and FIG. 7c). Interestingly, they also expressed elevated levels of pluripotency markers such as Nanog, Oct4 or Sox2 in vivo (FIG. 6d), suggesting that these structures contained a complex mixture of undifferentiated and differentiated cells.

It has been recently reported that iPSCs generated in vivo from an OSKM transgene are able to form small embryo-like structures, containing tissues derived from the three germinal layers, when inoculated intraperitoneally (Abad et al., 2013). In previous assays carried out by the group of the present inventors, wild-type iPSCs generated in vivo were able to form embryo-like structures in 11% of injected mice, an efficiency similar to the one reported previously (Abad et al., 20139. However, tKI iPSCs generated in vitro were much more efficient with 83% of injected mice showing embryo-like structures, even complex embryo-like structures never found after WT iPSCs injections, characterized by the expression of several markers or embryonic development, the three germ layers and extra-embryonic tissues (see FIG. 8a, where it can be seen than tKI embryo-like structures were positive for specific markers of the three embryonic layers, as in the case of in vivo-formed iPSCs). Table 4 below shows the frequency of nude mice with embryo-like structures (E-Ls) in their abdominal cavity 20-30 days after intraperitoneal (i.p.) injection of 400000-500000 WT or iKI iPSCs or in vivo (iv)-generated WT iPSCs. The number of independent clones tested per condition is indicated in the panel (each animal was inoculated with a different clone).

TABLE 4

Embryo-like (E-Ls) structures in abdominal cavity after i.p. injection of iPSCs

| Cells | No of clones | Mice inoculated | Mice with E-Ls | % |
|---|---|---|---|---|
| WT iPSCs | 8 | 8 | 0 | 0 |
| iv* WT iPSCs | 9 | 9 | 1 | 11 |
| tKI iPSCs | 12 | 12 | 10 | 83 |

*iv: in vivo-generated

It was next tested whether miR-203 could also influence the potential of pluripotent cells in forming chimeras. Table 5 shows the frequency of chimeric contribution exhibited by KI iPSCs and ESCs, transiently treated in vitro with vehicle (KI) or Dox (tKI) as indicated (2 independent clones were analyzed per condition) and summarizes the obtained results. From said Table 5, it can be seen that tKI ES cells showed a 27.5% of success in the formation of chimeras with 100% chimerism (as determined by coat color) versus 11.8% in control non-induced KI ES cells. Moreover, tKI iPSCs showed a 5.8% of success in the generation of 100% chimeras, while control non-induced iPSCs showed 1.5% of success in these assays. All the chimeras generated in these experiments contributed to germline transmission.

TABLE 5

Frequency of chimeric contribution exhibited by KI iPSCs and ESC

| Cells | KI iPSCs (n = 2) | tKI iPSCs (n = 2) | KI ESCs (n = 2) | tKI ESCs (n = 2) |
|---|---|---|---|---|
| Embryo transferred | 135 | 137 | 68 | 69 |
| Pups born | 4 | 10 | 12 | 19 |
| Chimeras born (adult) | 2 (0) | 8 (1) | 8 (1) | 19 (10) |
| % success | 1.5 | 5.8 | 11.8 | 27.5 |

Finally, the performance of tKI iPSCs was tested in the tetraploid complementation assay with WT or tKI iPSCs or WT ESCs (n=3 clones per condition). Tetraploid embryo complementation represents the most stringent test for pluripotency and developmental potency. iPSCs are very inefficient in this assay in which any viable live-born animal develops uniquely at the expenses of the injected diploid iPS (or ES) cells in a tetraploid blastocyst. As can be seen in Table 6, no viable pups were obtained in control iPSCs, while tKI iPSCs were able to form full-chimeras (one of them is shown in FIG. 8b) with a rate of success of 2.8%, closer to the 11.9% achieved with control ESCs.

TABLE 6

Results of embryo tetrapioid complementation assays

| Cells | WT iPSCs (n = 3) | tKI iPSCs (n = 3) | ESCs (n = 3) |
|---|---|---|---|
| Embryos transferred | 69 | 144 | 42 |
| All IPSC/ESC mice | 0 | 4 | 5 |
| % success | 0 | 2.8 | 11.9 |

Example 3. miR-203 Effects in Pluripotency are Dnmt3a/b-Dependent

To identify possible miR-203 targets involved in the control of pluripotency, the inventors searched for predicted miR-203 targets among the transcripts upregulated in miR-203-null iPSCs (more or equal than 2-fold increase respect to the wild type IPSCs) and downregulated in the miR-203 tKI inducible model (more or equal than 2 fold decrease respect to the wild type situation).

678 transcripts were found upregulated in miR-203-null iPSCs and downregulated in miR-203 tKI iPSCs, and 35 of those were predicted miR-203 targets (FIG. 9a), as can be seen in Table 7a below (the computational predictions were based on miRanda, Target Scan and MicroTar databases).

When the search was restricted to identify predicted miR-203 targets among the transcripts downregulated in tKI iPSCs (FIG. 9f). The selection from that list of those genes involved in epigenetic regulation of expression (G00040029) resulted in 18 GO0040029 transcripts downregulated in tKI iPSCs that were predicted miR-203 targets according to the same microRNA target prediction algorithms used for Table 7a. The list of said 18 transcripts is shown in Table 7b below.

TABLE 7a

List of miR-203 predicted targets in *Mus musculus* among the transcripts downregulated in miR-203 tKI and upregulated in miR-203-null iPSCs

| | log2 (fold_change) | | Predicted miR-203 targets | |
|---|---|---|---|---|
| Transcript | tKI vs. WT | KO vs. WT[a] | Agreement[b] | Computational Predictions (method\|target-site) |
| Tspan1 | −3.25 | 4.91 | −0.77 | "Microlar\|7mer-m8\| |
| Slc2a3 | −4.79 | 4.21 | 1.54 | "Miranda\|7mer-m8\| |
| Podxl | −5.01 | 4.21 | 1.31 | "Miranda\|7mer-m8\| |
| Nptx1 | −2.67 | 3.96 | −0.76 | "Targetscan\|8mer\| |
| Dnmt3b | −2.36 | 3.39 | 1.33 | Miranda\|Offset 3-8 6mer\| |
| Ptpn3 | −1.77 | 3.38 | 1.36 | "Miranda\|7mer-m8\| |
| Epb4.1l4b | −1.16 | 3.17 | −0.76 | "Targetscan\|8mer\| |
| Hic2 | −1.34 | 2.98 | −0.77 | "Targetscan\|7mer-1A\| |
| Hells | −1.40 | 2.95 | 1.24 | "Miranda\|7mer-m8\| |
| Fam81a | −2.38 | 2.93 | 1.21 | "Miranda\|7mer-m8\| |
| Cth | −3.23 | 2.84 | 1.26 | "Miranda\|N/A\| |
| Alg13 | −2.46 | 2.57 | 1.21 | "Miranda\|N/A\| |
| Ppat | −1.32 | 2.45 | 1.28 | "Miranda\|7mer-m8\| |
| Ap1s3 | −1.06 | 2.43 | 1.30 | "Miranda\|7mer-m8\| |
| Dppa2 | −3.40 | 2.39 | 1.29 | "Miranda\|6mer+\| |
| Tet2 | −1.03 | 2.35 | 1.37 | "Miranda\|8mer\| |
| Dock5 | −1.87 | 2.33 | −0.77 | "Targetscan\|7mer-1A\| |
| Cdc6 | −1.45 | 2.30 | 1.26 | "Miranda\|Offset 3-8 6mer\| |
| Nfatc2 | −2.59 | 2.28 | 1.30 | "Miranda\|N/A\| |
| Glt1d1 | −6.89 | 2.18 | 1.38 | "Miranda\|7mer-m8\| |
| Fam60a | −1.15 | 2.00 | 1.27 | "Miranda\|6mer\| |
| Hspa12b | −1.05 | 1.91 | 1.33 | "Miranda\|N/A\| |
| Tfrc | −2.32 | 1.77 | 1.26 | "Miranda\|Offset 3-8 6mer\| |
| Sgol1 | −1.36 | 1.74 | 1.34 | "Miranda\|8mer\| |
| Rad51 | −1.23 | 1.74 | 1.25 | "Miranda\|Offset 3-8 6mer\| |
| Grb7 | −0.64 | 1.66 | −0.76 | "Microtar\|Offset 1-7 7mer-m8\| |
| Cited2 | −1.30 | 1.56 | 1.52 | "Miranda\|7mer-m8\| |
| Dnmt3a | −0.53 | 1.50 | 1.43 | Miranda\|7mer-m8\| |
| Pola1 | −2.53 | 1.42 | 1.59 | "Miranda\|7mer-m8\| |
| Msh3 | −1.09 | 1.32 | 1.30 | "Miranda\|7mer-m8\| |
| Tmpo | −1.42 | 1.29 | 1.21 | "Miranda\|N/A\| |
| Adh7 | −1.03 | 1.20 | 1.38 | "Miranda\|N7A\| |
| Xrcc2 | −1.23 | 1.19 | 1.37 | "Miranda\|7mer-m8\| |
| Fam49a | −1.16 | 1.18 | 1.29 | "Miranda\|8mer\| |
| Nsl1 | −1.63 | 1.03 | 1.48 | "Miranda\|7mer-m8\| |

[a]List ordered by level of upregulation in miR-203 KO iPSCs. For those targets with multiple predictions, only the values corresponding to the highest prediction is shown.
[b]The agreement score of the target, which is a weighted mean (using each method's experimental AUC) of the computational methods scores in the prediction group.

TABLE 7b

List of miR-203 predicted targets in *Mus musculus* among the transcripts downregulated in miR-203 tKI and involved in the epigenetic regulation of gene expression (GO0040029)

| | | Predicted miR-203 targets | |
|---|---|---|---|
| Transcript | tKI vs. WT log2 (fold change) | Agreement[a] | Computational Predictions (method\|target-site) |
| Dnmt3a | −0.53 | 1.43 | Miranda\|7mer-m8\| |
| Dnmt3b | −2.36 | 1.33 | Miranda\|Offset 3-8 6 mer |
| Uhrf2 | −0.52 | 1.31 | Miranda\|N/A\|\| |
| Trim27 | −0.74 | 1.29 | Miranda\|Offset 3-8 6 mer |
| Tet1 | −1.05 | 1.29 | Miranda\|8mer\|\| |
| Apobec1 | −0.67 | 1.26 | Miranda\|N/A\| |
| Ctcf | −0.65 | 1.24 | Miranda\|6mer\| |
| Hells | −1.40 | 1.24 | Miranda\|7mer-m8\|\| |
| Klf2 | −1.11 | 1.23 | Miranda\|N/A\| |
| Mier1 | −0.86 | 1.21 | Miranda\|6mer\| |
| Smarca5 | −0.63 | 1.20 | Miranda\|N/A\| |
| Dnd1 | −1.34 | 1.20 | Miranda\|Offset 3-8 6 mer |
| Brca1 | −1.51 | 1.20 | Miranda\|6mer |
| Dpy30 | −0.90 | 0.27 | Miranda\|N/A\| |
| | | | Rnahybrid\|Offset 1-7 8mer\| |
| Rlim | −0.51 | −0.75 | Pita\|8mer\| |
| Rbm3 | −1.04 | −0.76 | Pita\|8mer\|\| |
| H2afy | −0.54 | −0.76 | Targetscan\|7mer-m8\| |

[a]The agreement score of the target, which is a weighted mean (using each method's experimental AUC) of the computational methods scores in the prediction group.

Among the transcripts deregulated in these two analyses, the inventors decided to focus on de novo DNA methyltransferases Dnmt3a (DNA Methyltransferase 3 Alpha, EC_number 2.1.1.37; Human Gene HGNC:2978, Ensembl: ENSG00000119772, NCBI gene: 1788, NCBI accession number: NM_022552 version NM_022552.4 7 Oct. 2016); *Mus musculus* gene MGI: 1261827, Ensembl: ENSMUSG00000020661; NCBI Gene: 13435, NCBI accession number: NM_001271753 version NM_001271753.1 15 Feb. 2015) and Dnmt3b (DNA Methyltransferase 3 beta EC_number 2.1.1.37; Human Gene HGNC:2979, Ensembl: ENSG00000088305 version ENSG00000088305.18; NCBI gene: 1789, NCBI accession number: NM_006892 version NM_006892.3 3 Nov. 2016; *Mus musculus* gene MGI: 1261819, Ensembl ENSMUSG00000027478 version ENS-MUSG00000027478.15, NCBI gene 13436, NCBI accession number: NM_001003961 version NM_001003961 15 Feb. 2015) (data based on the following databases: HUGO Gene Nomenclature Committee (http://www.genenames.org/); MGI Mouse Genome Informatics (http://www.informatics.jax.org/) updated Mar. 13, 2017; Ensembl (www.ensembl.org) release 87, December 2016). The decision was based on the relevance of chromatin modifications in pluripotency, and the long-term effect resulting from transient expression of miR-203 suggestive of an epigenetic alteration. In addition, these two transcripts were also significantly downregulated after expression of miR-203 mimics in wild-type iPSCs (log 2 fold change=−0.24 for Dnmt3a and −0.22 for Dnmt3b transcripts). Human miR-203 and DNMT3a/b transcripts have been previously shown to display inverse expression profiles in cancer cells (Sandhu et al., 2012; Gasque Schoof et al., 2015) and DNMT3b was recently shown to be a direct miR-203 target in human colon cancer cells (To et al., 2016).

Both Dnmt3a and Dnmt3b transcripts contain conserved miR-203 sites in their 3'-UTR (FIG. 10a) (Dnmt3a: SEQ ID NO:49; Dnmt3b: SEQ ID NO:51) and exogenous expression of miR-203 led to decreased signal of a luciferase construct fused to these sequences, but not to 3'-UTR sequences from the related genes Dnmt3l or Dnmt1 (FIG. 9b,c). This regulation was eliminated (FIG. 9c) when the putative miR-203 binding sites were mutated and the luciferase construct was fused to the 3'-UTR mutated sequences of Dnmt3a (SEQ ID:50) or Dnmt3b (SEQ ID NO:52) (FIG. 10b) indicating a direct control of these transcripts by miR-203. Notably, overexpression of miR-203-resistant Dnmt3a and Dnmt3b cDNAs, simultaneously to the transient doxycycline treatment, prevented the overgrowth of the corresponding embryoid bodies (FIG. 9d), as well as the increase in 2C-like cells induced by the retroviral expression of miR-203 in wild-type ESCs (FIG. 9e).

To test to what extent downregulation of Dnmt3a/b could mimic the effect of miR-203, the inventors knocked down these de novo DNA methyltransferases by RNA interference means (siDnmt3a/b). RNA sequencing of these samples revealed that siDnmt3a/b iPSCs exhibited a transcriptomic profile closer to tKI iPSCs (FIG. 9g). In addition, downregulation of Dnmt3a/b induced the growth, formation of long cavities and increased beating of EBs to a similar extent to that observed in tKI iPSCs-derived EBs (FIG. 9h), whereas individual knockdown of these transcripts displayed partial effects (quantified in FIG. 9h).

Knockdown of Dnmt3a/b also increased the 2C-like population in wild-type ESCs as scored by the expression of the MERVL element (FIG. 9i,j,k), although to lesser extent than miR-203. Whether these differences are due to variable efficiencies in the control of gene expression of additional miR-203 targets is unclear at present. Moreover, expression of miR-203-resistant Dnmt3a/b cDNAs significantly prevented the expression of the 2C-related marker (FIG. 9i,j), thereby suggesting that Dnmt3a/b de novo methyltransferases are critical targets of miR-203 in the induction of naive pluripotency.

As Dnmt3a/b are de novo methyltransferases involved in methylation of DNA, the inventors next analyzed the genome-wide methylation profile of wild-type and tKI iPSCs (before and after induction with doxycycline) as well as embryoid bodies derived from them (FIG. 11a). Wild-type and tKI iPSCs displayed similar levels of methylation before Dox and wild-type cells were not affected by this treatment. In contrast, transient induction of miR-203 for 5 days resulted in a genome-wide hypomethylation in tKI iPSCs, which was surprisingly even more reduced 20 days after withdrawal of Dox (t=25; FIG. 11b-e), a time-point in which Dnmt3a/b transcript levels had already recovered after their repression in the presence of Dox (FIG. 12a). Notably, the number of DNA methylation valleys (DMVs; (Xie et al., 2013)) and partially methylated domains (PMDs; (Lister et al., 2009)) were increasingly higher in the tKI iPSCs with time (FIG. 11b and FIG. 12b); for instance, 131 PMDs were found at t=0 while 548 and 6,555 PMD were found at t=10 and t=25, respectively. DNA methylation comparison between groups showed that 128 differentially methylated regions (DMRs) out of 131 total DMRs (97.7%; t=10 versus t=0) and 12,542 out of 12,549 (99.9%; t=25 versus t=0) DMRs were hypomethylated in tKI iPSCs as a consequence of previous exposure to miR-203 (FIG. 11e and FIG. 12b). Transcriptional analysis of these samples suggested that deregulated genes with affected DMRs were significantly enriched in chromatin regulators, or genes involved in DNA replication and cell division or embryonic morphogenesis among other pathways (FIG. 13a).

As validation of these observations, bisulphite modification followed by sequencing confirmed miR-203-dependent hypomethylation of the locus encoding the E74 Like ETS Transcription Factor 5 (Elf5), a protein involved in the differentiation of epithelial cells and trophoblast stem-cell renewal and differentiation (FIG. 13b,c). Interestingly, the embryoid bodies derived from tKI iPSCs displayed higher genome-wide DNA methylation (FIG. 11b,c) in agreement with upregulation of Dnmt3a and Dnmt3b transcripts (FIG. 12a). As also observed at a genome-wide scale, the Elf5 DMR was hypermethylated in embryoid bodies generated from tKI iPSCs when compared to wild-type-derived structures (FIG. 13b,c).

Previous data suggest that interfering with DNA methyltransferase expression or activity results in general hypomethylation in the genome (Blattler et al., 2014; Liao et al., 2015; Mikkelsen et al., 2008). To further analyze whether the changes in methylation in tKI iPSCs were related to the miR-203-mediated repression of Dnmt3a/b, the authors studied the changes in DMR methylation after overexpression a miR-203-resistant form of these DNA methyltransferases in tKI iPSCs. As depicted in FIG. 11f, expression of exogenous Dnmt3a/b rescued the hypomethylation observed after miR-203 induction both in the Elf5 DMRs as well as in a DMR located close to the histone deacetylase Sirt6 gene, suggesting that these de novo DNA methyltransferases are critical targets of miR-203 in inducing genome-wide hypomethylation.

Example 4. Transient Expression of miR-203 Improves Differentiation and Maturation into Cardiomyocytes Since transient expression of miR-203 improves the function of pluripotent cells in several assays (FIGS. 2-8), it was decided to directly test the effect of expressing this miRNA during cardiomyocyte differentiation. The effect of miR-203 was first tested in primary cardiomyocytes isolated from neonatal (P1) rats that undergo further expansion and differentiation when cultured in vitro. miR-203 mimics triggered a transient burst of cell proliferation as measured by incorporation of the nucleotide analogueue EdU (FIG. 14a) and mitotic markers such as cyclin B1 (FIG. 14b). Importantly, this increase in proliferation occurred in cardiac troponin T (cTnT)-positive cells (FIG. 15a) and resulted in cells with increased ratio of Myh6 versus Myh7 myosin heavy chain genes (FIG. 14b), a developmentally regulated switch that correlates with cardiomyocyte maturation and cardiac performance (Miyata et al., 2000).

The inventors also tested a cardiomyocyte differentiation protocol from wild-type iPSCs (Kattman et al., 2011). Mouse iPSCs were transiently transfected with miR-203 or control mimics and 15 days later they were differentiated into cardiomyoytes using specific media and culture conditions (see Methods). This differentiation was accompanied by increased expression of cardiomyocyte differentiation transcripts such as myosin heavy chain (Myh), atrial natriuretic peptide (Nppa), cardiac troponin T (encoded by the Tnnt2 gene), markers for cardiac progenitors such as insulin gene enhancer transcription factor Isl1 and Tbx5 in iPSCs previously treated with miR-203 mimics (FIG. 15b). Importantly, transient exposure to miR-203 resulted in higher expression of not only differentiation but also maturation markers such as the potassium channel components encoded by the Kcnh2, Hcn1 and Kcna4 genes (Otsuji et al., 2010), that were only minimally induced in cells treated with control mimic RNAs (FIG. 15c). In line with these data, the beating frequency in cardiomyocytes derived from miR-203-treated iPSCs was significantly higher suggesting enhanced functionality (FIG. 15d). Expression of miR-203-resistant forms of Dnmt3a and Dnmt3b in parallel to miR-203 (FIG. 14c) prevented the upregulation of these differentiation and maturation markers (FIG. 14d,e), suggesting the relevance of the miR-203-Dnmt3a/b axis in functional differentiation and maturation of cardiomyocytes from pluripotent cells.

The fact that miR-203 renders iPSCs more naive and increases their potency and plasticity to differentiate, inspired the inventors to test the effect of miR-203 in cardiac regeneration after injury. The neonatal mouse cardiac cryoinjury enables testing of molecular interventions to stimulate regeneration, in a model with characteristics similar to those observed in pediatric heart disease (Polizzotti et al., 2016). Heart muscle cell death was induced by cryoinjury in ColA1(miR-203/miR-203); Rosa26(rtTA/rtTA) mice at postnatal day 1 (FIG. 16a), and neonates were treated with vehicle (control) or Dox (to induce miR-203 expression) for seven days. After 1 week of recovery, control pups displayed significantly larger fibrotic areas in the heart, whereas wound healing was significantly improved in Dox-treated neonates (FIG. 16b,c). Identification of CD34-positive cardiac progenitors concomitant with Sirius Red staining revealed an accumulation of undifferentiated progenitors in the scar of control hearts. Treatment with doxycycline, however, led to a significant reduction of fibrosis accompanied by reduced presence of these progenitors in the injured area and a better recovery of normal tissue (FIG. 16d). Of interest, the percentage of living pups in the operated litters was higher in the Dox-treated group compared to controls (FIG. 16e), suggesting the therapeutic effect of inducing miR-203 during cardiac regeneration and the possible relevance of this microRNA in regeneration medicine.

Example 5. miR-203 Induces a Ground Naïve State In Vitro

In order to be able to compare properly the properties of the pluripotent cells obtained after transient exposure to increased levels of miR-203 with those of natural cells in a ground state, quantitative PCR analysis in mouse embryos isolated at different stages was performed. The results (FIG. 17) show that miR-203 expression was low in oocytes, significantly induced at the 2-cell stage and displayed a gradual reduction in morulas and blastocysts.

The expression of miR-203 at the 2-cell stage inspired the inventors to analyze the expression of 2C markers in cultured tKI mouse PSCs. Transient expression of miR-203-GFP in wild-type ES cells significantly increased the number of 2C-like cells as determined by the expression of the murine endogenous retrovirus with leucine tRNA primer (MuERV-L; 2C::tdTomato reporter) (Macfarlan et al., 2012) (FIG. 18a). In line with these observations, exposure to miR-203 induced the expression of genes harboring a proximal upstream or an intronic MERVL element (FIG. 18b). In addition, miR-203 exposure induced the expression of a significant number of genes characteristic of totipotent 2C blastomeres (Biase et al., 2014) (FIG. 18c,d). Dramatically, almost every transcript included in the 282-gene signature of 2C cells was induced by miR-203 ten days after Dox withdrawal, and their expression was gradually reduced with time (FIG. 18c). Of interest, transient exposure to miR-203 mimics also rendered human pluripotent cells to a ground naive state (FIG. 18e,f), as measured by the expression of the family HERVH of human endogenous retroviruses (HERVs) involved in the maintenance of human naive pluripotency (Wang et al., 2016). miR-203 mimics induced the expression of the HERVH-GFP reporter in a significant number of colonies, in many cases not only in the periphery but in almost the totality of the cells of the colony. When the differentiation potential of these cultures was tested, human tKI iPSCs generated significantly bigger EBs with larger internal cavities than the control counterparts (FIG. 18g,h). Then, the results indicate that the observations in mouse pluripotent cells might be extended to human pluripotent cells.

Example 6. miR-203 Induces Naïve Pluripotency in Cells Cultured in 2i/LIF Medium Since the combination of the MEK inhibitor PD0325901 and the GSK3 inhibitor CH1R99021 with LIF (2i/L conditions) has been previously shown to render iPSCs closer to ESCs (Ying et al., 2008), so that it can be considered the former standard for maintaining stemness potential, it was also decided to test the effect of miR-203 under 2i/L conditions.

It was observed that tKI iPSCs grown in 2i/L also displayed an enrichment in the transcription of stemness factors and developmental pathways when compared to wildtype iPSCs grown in the same conditions (FIG. 19a). In addition, pre-treatment with Dox for 5 days, 2 weeks prior to EB assays, of tKI iPSCs cultured in 2i/L conditions promoted a significant increase in EB size, formation of large internal cavities as well as beating (FIG. 19b,c), suggesting an additional effect of miR-203 over the 2i/L conditions.

Example 7. miR-203 has Little Effect in ICR Regions Compared to 2i/L Conditions

Given the recent findings showing that a widespread loss of methylation in PSC cultures might be deleterious when accompanied by massive erasure of genomic imprints (Choi et al., 2017; Yagi et al., 2017), the inventors decided to test the methylation levels at 103 different Imprinting Control Regions (ICR) in tKI iPSCs.

Whereas tKI iPSCs displayed a progressive demethylation of genes (darker signal, red in the original, at t=10 and t=25 in FIG. 20; left panel), demethylation of ICRs was very limited at t=10 and moderate at t=25 in the same samples (right panel). Importantly, demethylation was in all cases fully recovered upon differentiation (tKI iPSCs-derived EBs; FIG. 20), suggesting that demethylation of tKI iPSCs, both in DMRs and ICRs, is manageable and reversible, and does not compromise neither the quality of iPSCs nor their competence to differentiate Thus, it can be seen that miR-203 has little effect in ICR regions compared to 2i/L conditions, thus explaining the significant improvement of miR-203 treated cells in multiple in vivo assays.

CONCLUSION

In conclusion, it is herein disclosed and demonstrated, by using a variety of cellular and in vivo models, that controlling transient miR-203 expression in induced pluripotent stem (iPS) or embryonic stem (ES) cells improves the ability of these cells to differentiate into multiple cell lineages and to reach further maturation properties without interfering with their self-renewal properties. This effect is mediated through the miR-203-dependent control of de novo DNA methyltransferases Dnmt3a and Dnmt3b, which in turn regulate the methylation landscape of pluripotent cells.

REFERENCES

Abad, M. et al. Reprogramming in vivo produces teratomas and iPS cells with totipotency features. *Nature* 502, 340-345, doi:10.1038/nature12586 (2013)

Ambros, V. The functions of animal microRNAs. *Nature* 431, 350-355, doi:10.1038/nature02871 (2004).

Beard, C., Hochedlinger, K., Plath, K., Wutz, A. & Jaenisch, R. Efficient method to generate single-copy transgenic mice by site-specific integration in embryonic stem cells. *Genesis* 44, 23-28, doi:10.1002/gene.20180 (2006)

Biase, F. H., et al., Cell fate inclination within 2-cell and 4-cell mouse embryos revealed by single-cell RNA sequencing. *Genome research* 24, 1787-1796 (2014).

Bilic, J. and Izpisua Belmonte, J. C. Induced Pluripotent Stem Cells Versus Embryonic Stem Cells: Close Enough or Yet Too Far Apart?. *Stem Cells,* 30(1), 33-41 (2012).

Blattler, A. et al. Global loss of DNA methylation uncovers intronic enhancers in genes showing expression changes. *Genome biology* 15, 469, doi:10.1186/s13059-014-0469-0 (2014)

Bock, C. et al. BiQ Analyzer: visualization and quality control for DNA methylation data from bisulfite sequencing. *Bioinformatics* 21, 4067-4068, doi:10.1093/bioinformatics/bti652 (2005).

Bueno, M. J. et al. Genetic and epigenetic silencing of microRNA-203 enhances ABL1 and BCR-ABL1 oncogene expression. *Cancer cell* 13, 496-506, doi:10.1016/j.ccr.2008.04.018 (2008).

Card D A, Hebbar P B, Li L, Trotter K W, Komatsu Y, Mishina Y, Archer T K 2008. Oct4/Sox2-regulated miR-302 targets cyclin D1 in human embryonic stem cells. Mol Cell Biol 28: 6426-6438

Chetty, S., Pagliuca F, Honore C, Kweudjeu A, Rezania A, Melton D A. A simple tool to improve pluripotent stem cell differentiation. *Nat Methods* 10(6): 553-556 (2013).

Choi, J., et al. Prolonged Mek1/2 suppression impairs the developmental potential of embryonic stem cells. *Nature* 548, 219-223 (2017).

Chung et al, Human Embryonic Stem Cell lines generated without embryo destruction, Cell Stem Cell (2008)

Chung, H. C. et al. Human induced pluripotent stem cells derived under feeder-free conditions display unique cell cycle and DNA replication gene profiles. *Stem cells and development* 21, 206-216, doi:10.1089/scd.2010.0440 (2012).

Gasque Schoof, C. R., Izzotti, A., Jasiulionis, M. G. & Vasques Ldos, R. The Roles of miR-26, miR-29, and miR-203 in the Silencing of the Epigenetic Machinery during Melanocyte Transformation. *BioMed research international* 2015, 634749, doi:10.1155/2015/634749 (2015).

Graña, O., Rubio-Camarillo, M., Fernandez-Riverola, F., Pisano, S. G. & Gonzalez-Peña, D. nextpresso: next generation sequencing expression analysis pipeline. *Curr Bioinformatics* Accepted for Publication. ISSN: (Online) 2212-392X—(Print) 1574-8936 (2017)

Hanna, J. Saha K, Pando B, van Zon J, Lengner C J, Creyghton M P, van Oudenaarden A, Jaenisch R. Direct cell reprogramming is a stochastic process amenable to acceleration. *Nature.* 2009 Dec. 3; 462(7273):595-601. doi: 10.1038/nature08592. Epub 2009 Nov. 8.

Honda, A., Hatori M., Hirose M., Honda C, Izu H, Inoue K, Hirasawa R, Matoba S, Togayachi S, Miyoshi H, Ogura A. Naive-like Conversion Overcomes the Limited Differentiation Capacity of Induced Pluripotent Stem Cells. *J Biol Chem.* 288(6): 26157-26166 (2013).

Huang, Z. P. et al. Cardiomyocyte-enriched protein CIP protects against pathophysiological stresses and regulates cardiac homeostasis. *The Journal of clinical investigation* 125, 4122-4134, doi:10.1172/JCI82423 (2015)

Huang, X. A. et al. The microRNA regulation of stem cells. *Willey Interdisciplinary Reviews: Developmental Biology,* vol. 1, no. 1, pages 83-95, doi:10.1002/wdev.5 (2011).

Jackson, M. et al. Severe global DNA hypomethylation blocks differentiation and induces histone hyperacetylation in embryonic stem cells. *Molecular and cellular biology* 24, 8862-8871, doi:10.1128/MCB.24.20.8862-8871.2004 (2004).

Kapinas, K. et al. microRNA-Mediated Survivin Control of Plutipotency. *Journa of Cellular Physiology* 230, 63-70 (2015).

Kattman, S. J. et al. Stage-specific optimization of activin/nodal and BMP signaling promotes cardiac differentiation of mouse and human pluripotent stem cell lines. *Cell stem cell* 8, 228-240, doi:10.1016/j.stem.2010.12.008 (2011).

Kole, R., Krainer A. R., Altman S. RNA therapeutics: beyond RNA interference and antisense oligonucleotides. *Nat. Rev. Drug Discov.,* 11, 125-140 (2012).

Langmead, B., Trapnell, C., Pop, M. & Salzberg, S. L. Ultrafast and memory-efficient alignment of short DNA sequences to the human genome. *Genome biology* 10, R25, doi:10.1186/gb-2009-10-3-r25 (2009).

Lee, H. J. et al. Lineage specific methylation of the Elf5 promoter in mammary epithelial cells. *Stem cells* 29, 1611-1619, doi:10.1002/stem.706 (2011)

Leonardo, T. R., Schultheisz, H. L., Loring, J. F. & Laurent, L. C. The functions of microRNAs in pluripotency and reprogramming. *Nature cell biology* 14, 1114-1121, doi: 10.1038/ncb2613 (2012).

Li, H. & Durbin, R. Fast and accurate short read alignment with Burrows-Wheeler transform. *Bioinformatics* 25, 1754-1760, doi:10.1093/bioinformatics/btp324 (2009).

Li, M. & Izpisua Belmonte, J. C. Looking to the future following 10 years of induced pluripotent stem cell technologies. *Nature protocols* 11, 1579-1585, doi:10.1038/nprot.2016.108 (2016).

Liao, J. et al. Targeted disruption of DNMT1, DNMT3A and DNMT3B in human embryonic stem cells. *Nature genetics* 47, 469-478, doi:10.1038/ng.3258 (2015)

Lin L, Chang D C, Chang-Lin S, Lin C H, Wu D T, Chen D T, Ying S Y 2008. Mir-302 reprograms human skin cancer cells into a pluripotent ES-cell-like state. RNA 14: 2115-2124

Macfarlan, T. S. et al. Embryonic stem cell potency fluctuates with endogenous retrovirus activity. *Nature* 487, 57-63, doi:10.1038/nature11244 (2012)

Marson A, Levine S S, Cole M F, Frampton G M, Brambrink T, Johnstone S, Guenther M G, Johnston W K, Wernig M, Newman J, et al. 2008. Connecting microRNA genes to the core transcriptional regulatory circuitry of embryonic stem cells. *Cell* 134: 521-533

Michel, C. I. & Malumbres, M. microRNA-203: Tumor Suppression and Beyond. *MicroRNA* 2, 118-126 (2013).

Mikkelsen, T. S. et al. Dissecting direct reprogramming through integrative genomic analysis. *Nature* 454, 49-55, doi:10.1038/nature07056 (2008).

Miyata, S., Minobe, W., Bristow, M. R. & Leinwand, L. A. Myosin heavy chain isoform expression in the failing and nonfailing human heart. *Circulation research* 86, 386-390 (2000).

Nissan, X., et al. miR-203 modulates epithelial differentiation of human embryonic stem cells towards epidermal stratification. *Developmental Biology* 356(2), 506-515 (2011).

Niwa H, Ogawa K, Shimosato D, Adachi K. A parallel circuit of LIF signalling pathways maintains pluripotency of mouse ES cells. *Nature;* 460(7251):118-22 (2009). doi:10.1038/nature08113

Okano, M., Bell, D. W., Haber, D. A. & Li, E. DNA methyltransferases Dnmt3a and Dnmt3b are essential for de novo methylation and mammalian development. Cell 99, 247-257 (1999)

Otsuji, T. G. et al. Progressive maturation in contracting cardiomyocytes derived from human embryonic stem cells: Qualitative effects on electrophysiological responses to drugs. *Stem cell research* 4, 201-213, doi:10.1016/j.scr.2010.01.002 (2010).

Papp, B. and Plath, K-. Reprogramming to pluripotency: stepwise resetting of the epigenetic landscape. Cell Research, 21(3), 486-501 (2011)

Polizzotti, B. D., Ganapathy, B., Haubner, B. J., Penninger, J. M., and Kuhn, B. A cryoinjury model in neonatal mice for cardiac translational and regeneration research. *Nature protocols* 11, 542-552 (2016)

Rodriguez, C. I. et al. High-efficiency deleter mice show that FLPe is an alternative to Cre-loxP. *Nature genetics* 25, 139-140, doi:10.1038/75973 (2000).

Rosenbloom, K. R. et al. The UCSC Genome Browser database: 2015 update. *Nucleic acids research* 43, D670-681, doi:10.1093/nar/gku1177 (2015)

Sandhu, R., Rivenbark, A. G. & Coleman, W. B. Loss of post-transcriptional regulation of DNMT3b by microRNAs: a possible molecular mechanism for the hypermethylation defect observed in a subset of breast cancer cell lines. *International journal of oncology* 41, 721-732, doi:10.3892/ijo.2012.1505 (2012).

Schwenk, F., Baron, U. & Rajewsky, K. A cre-transgenic mouse strain for the ubiquitous deletion of loxP-flanked gene segments including deletion in germ cells. *Nucleic acids research* 23, 5080-5081 (1995)

Shenoy, A. & Blelloch, R. H. Regulation of microRNA function in somatic stem cell proliferation and differentiation. Nature reviews. *Molecular cell biology* 15, 565-576, doi:10.1038/nrm3854 (2014).

Takahashi, K. & Yamanaka, S. Induction of pluripotent stem cells from mouse embryonic and adult fibroblast cultures by defined factors. *Cell* 126, 663-676, doi:10.1016/j.cell.2006.07.024 (2006).

Takahashi, K. & Yamanaka, S. A decade of transcription factor-mediated reprogramming to pluripotency. *Nature reviews. Molecular cell biology* 17, 183-193, doi:10.1038/nrm.2016.8 (2016).

Tapia, N. & Scholer, H. R. Molecular Obstacles to Clinical Translation of iPSCs. *Cell stem cell* 19, 298-309, doi:10.1016/j.stem.2016.06.017 (2016).

To, K. K., Leung, W. W. & Ng, S. S. A novel miR-203-DNMT3b-ABCG2 regulatory pathway predisposing colorectal cancer development. *Molecular carcinogenesis*, doi:10.1002/mc.22508 (2016).

Trapnell, C. et al. Differential gene and transcript expression analysis of RNA-seq experiments with TopHat and Cufflinks. *Nature protocols* 7, 562-578, doi:10.1038/nprot.2012.016 (2012)

Volinia S, Nuovo G, Drusco A, Costinean S, Abujarour R, Desponts C, Garofalo M, Baffa R, Aeqilan R, Maharry K, et al. 2014. Pluripotent Stem Cell miRNAs and Metastasis in Invasive Breast Cancer. *J Natl Cancer Inst* 106(12): dju324doi: 10.1093/jnci/dju324

Wang, J., et al. Isolation and cultivation of naïve-like human pluripotent stem cells based on HERVH expression. *Nature protocols* 11, 327-346 (2016).

Wellner U, et al. The EMT-activator ZEB1 promotes tumorigenicity by repressing stemness inhibiting microRNA. *Nature Cell Biology* 11, 1487-1495 (2009).

Xu, Quing, et al. Overexpression of KLF4 promotes cell senescene through microRNA-203-survivin-p21 pathway. *Oncotarget* 7, 11 Aug. 2016, doi: 10.18632/oncotarget.11200

Yi, R., Poy, M. N., Stoffel, M. & Fuchs, E. A skin microRNA promotes differentiation by repressing 'stemness'. *Nature* 452, 225-229, doi:10.1038/nature06642 (2008).

Ying Q L, Wray J, Nichols J, Batlle-Morera L, Doble B, Woodgett J et al. The ground state of embryonic stem cell self-renewal. *Nature* 453(7194):519-23 (2008). doi: 10.1038/nature06968

The invention claimed is:

1. A method for dedifferentiating pluripotent stem cells to a more-naive state, which comprises:
   culturing pluripotent cells and
   exposing the pluripotent cells to miR-203 or an analogue thereof.

2. The method according to claim 1, wherein the cells are induced pluripotent stem cells or embryonic stem cells.

3. The method of claim 1, wherein exposing occurs for three to five days.

4. The method of claim 1, wherein the exposing comprises transducing the pluripotent cells with an expression vector that encodes miR-203.

5. The method of claim 1, wherein the exposing comprises adding to the culture medium miR-203 or the analogue thereof.

6. The method of claim 5, wherein the miR-203 is selected from hsa-miR-203a-3p or mmu-miR-203-5p.

7. The method of claim 1, wherein the exposing comprises transfecting the pluripotent cells with the miR-203 or the analogue thereof.

8. The method of claim 7, wherein the miR-203 is selected from hsa-miR-203a-3p or mmu-miR-203-5p.

9. The method of claim 1, wherein the exposing comprises adding to the culture medium the miR-203 analogue and wherein the miR-203 analogue is selected from:
   a) a modified RNA wherein at least one of the nucleotides is replaced by a chemically modified nucleotide, wherein the chemical modification is selected from the group of:
      i. replacing one or more phosphate bonds by phosphorothyoate bonds,
      ii. one or more modifications at the 2' position of the sugar moiety selected from 2'-O-methyl or 2'-O-methoxyethyl modifications, and/or
      iii. one or more modifications in the ribose moiety selected from the group of: those that give rise to a link connecting the oxygen at 2' with the carbon at 4', thus blocking the ribose in the conformation 3'-endo (LNAs: locked nucleic acids) or 2'-O, 4'-C ethylene bridged nucleic acids (ENA); the replacement of the sugar backbone by an amide-containing backbone such as an aminoethylglycine backbone, as in peptide nucleic acids (PNAs); and use of PMOs (nucleic acids where the ribose moiety is replaced by a morpholine group);
   b) a double stranded RNA with a duplex region of between 16 and 31 nucleotides in length and which contains a fragment which is at least 50% identical in their sequence to the sequence of nitrogenous bases of the RNA molecule represented by SEQ ID NO: 1, and
   c) optionally, additionally comprising at least one end of at least one of the strands a conjugate moiety comprising one or more units of cholesterol, cholestanol, stigmastrol, cholanic acid and ergosterol and, also optionally and additionally, a linker moiety that attaches the conjugate moiety to the strand, and
   d) also optionally and additionally, presenting one or more mismatches among the two strands.

10. The method of claim 1, wherein the dedifferentiating is characterized by an improvement of differentiation potential of the dedifferentiated pluripotent stem cells to cardiomyocytes.

11. The method of claim 1, wherein the pluripotent stem cells are obtained by contacting somatic differentiated cells with a nuclear reprogramming factor comprising a gene product of each one of the following families: Oct family, Klf family, Myc family and Sox family before the exposure to miR-203 or an analogue thereof.

12. A method for obtaining differentiated cells comprising i) obtaining dedifferentiated pluripotent stem cells according to the method of claim 1, and ii) differentiating the dedifferentiated pluripotent stem cells to obtain differentiated cells.

13. The method of claim 12, wherein the differentiated cells are selected from the group consisting of cardiomyocytes, neural cells, glial cells, chondrocytes, and pancreatic cells.

14. The method of claim 1, wherein the amount of miR203 is sufficient to down-regulate Dnmt3a, Dnmt3b, or a combination thereof.

15. The method of claim 1, wherein said exposing results in a genome-wide increase of unmethylated CpG compared to methylated CpG.

16. The method of claim 1, which further comprises exposing the cells to a composition comprising a MEK inhibitor (PD0325901), a GSK3 inhibitor (CHIR99021), and a cytokine leukemia inhibitory factor (LIF).

* * * * *

SEQUENCE LISTING

```
<160> NUMBER OF SEQ ID NOS: 86

<210> SEQ ID NO 1
<211> LENGTH: 22
<212> TYPE: RNA
<213> ORGANISM: Homo sapiens
<220> FEATURE:
<221> NAME/KEY: misc_feature
<222> LOCATION: (1)..(22)
<223> OTHER INFORMATION: hsa-miR203a-3p: Accession MIMAT0000264 in
      miRBase
```

```
<220> FEATURE:
<221> NAME/KEY: misc_feature
<222> LOCATION: (2)..(8)
<223> OTHER INFORMATION: Seed region

<400> SEQUENCE: 1
gugaaauguu uaggaccacu ag                                              22

<210> SEQ ID NO 2
<211> LENGTH: 110
<212> TYPE: RNA
<213> ORGANISM: Homo sapiens
<220> FEATURE:
<221> NAME/KEY: misc_feature
<222> LOCATION: (1)..(110)
<223> OTHER INFORMATION: hsa-miR203a, Accession MI0000283 in miRBase

<400> SEQUENCE: 2 guguuggga cucgcgcgcu ggguccagug guucuuaaca guucaacagu ucuguagcgc      60
aauugugaaa uguuuaggac cacuagaccc ggcgggcgcg gcgacagcga               110

<210> SEQ ID NO 3
<211> LENGTH: 76
<212> TYPE: RNA
<213> ORGANISM: Mus musculus
<220> FEATURE:
<221> NAME/KEY: misc_features
<222> LOCATION: (1)..(76)
<223> OTHER INFORMATION: mmu-miR-203, Accession MI0000246 in miRBase

<400> SEQUENCE: 3
gccuggucca gugguucuug acaguucaac aguucuguag cacaauugug aaauguuuag     60
gaccacuaga cccggc                                                    76

<210> SEQ ID NO 4
<211> LENGTH: 22
<212> TYPE: RNA
<213> ORGANISM: Mus musculus
<220> FEATURE:
<221> NAME/KEY: misc_feature
<222> LOCATION: (1)..(22)
<223> OTHER INFORMATION: mmu-miR-203-3p: Accession MIMAT0000236 in
      miRbase

<400> SEQUENCE: 4
gugaaauguu uaggaccacu ag                                              22

<210> SEQ ID NO 5
<211> LENGTH: 21
<212> TYPE: DNA
<213> ORGANISM: Artificial sequence
<220> FEATURE:
<223> OTHER INFORMATION: Forward primer of RT-PCR of mouse gene Dazl

<400> SEQUENCE: 5
ggttttacca cccgaactct g                                               21

<210> SEQ ID NO 6
<211> LENGTH: 21
<212> TYPE: DNA
<213> ORGANISM: Artificial sequence
<220> FEATURE:
<223> OTHER INFORMATION: Reverse primer of RT-PCR of mouse gene Dazl

<400> SEQUENCE: 6
tgtggttgct gatgaagact g                                               21
```

```
<210> SEQ ID NO 7
<211> LENGTH: 20
<212> TYPE: DNA
<213> ORGANISM: Artificial sequence
<220> FEATURE:
<223> OTHER INFORMATION: Forward primer of RT-PCR of mouse gene Dnmt1

<400> SEQUENCE: 7
cagagactcc cgaggacaga                                                   20

<210> SEQ ID NO 8
<211> LENGTH: 22
<212> TYPE: DNA
<213> ORGANISM: Artificial sequence
<220> FEATURE:
<223> OTHER INFORMATION: Reverse primer of RT-PCR of mouse gene Dnmt1

<400> SEQUENCE: 8
tttacgtgtc gttttcgtc tc                                                 22

<210> SEQ ID NO 9
<211> LENGTH: 19
<212> TYPE: DNA
<213> ORGANISM: Artificial sequence
<220> FEATURE:
<223> OTHER INFORMATION: Forward primer of RT-PCR of mouse gene Dnmt3a

<400> SEQUENCE: 9
aaacggaaac gggatgagt                                                    19

<210> SEQ ID NO 10
<211> LENGTH: 22
<212> TYPE: DNA
<213> ORGANISM: Artificial sequence
<220> FEATURE:
<223> OTHER INFORMATION: Reverse primer of RT-PCR of mouse gene Dnmt3a

<400> SEQUENCE: 10
actgcaatta ccttggcttt ct                                                22

<210> SEQ ID NO 11
<211> LENGTH: 22
<212> TYPE: DNA
<213> ORGANISM: Artificial sequence
<220> FEATURE:
<223> OTHER INFORMATION: Forward primer of RT-PCR of mouse gene Dnmt3a2

<400> SEQUENCE: 11
gggcaaactg aagtagtgat ga                                                22

<210> SEQ ID NO 12
<211> LENGTH: 18
<212> TYPE: DNA
<213> ORGANISM: Artificial sequence
<220> FEATURE:
<223> OTHER INFORMATION: Reverse primer of RT-PCR of mouse gene Dnmt3a2

<400> SEQUENCE: 12
ttacacggca cctgctga                                                     18

<210> SEQ ID NO 13
<211> LENGTH: 18
<212> TYPE: DNA
<213> ORGANISM: Artificial sequence
<220> FEATURE:
<223> OTHER INFORMATION: Forward primer of RT-PCR of mouse gene Dnmt3b
```

```
<400> SEQUENCE: 13
ccctccccca tccatagt                                                  18

<210> SEQ ID NO 14
<211> LENGTH: 21
<212> TYPE: DNA
<213> ORGANISM: Artificial sequence
<220> FEATURE:
<223> OTHER INFORMATION: Reverse primer of RT-PCR of mouse gene Dnmt3b

<400> SEQUENCE: 14
tctgctgtct cccttcattg t                                              21

<210> SEQ ID NO 15
<211> LENGTH: 19
<212> TYPE: DNA
<213> ORGANISM: Artificial sequence
<220> FEATURE:
<223> OTHER INFORMATION: Forward primer of RT-PCR of mouse gene Dnmt3l

<400> SEQUENCE: 15
aagtgaaccg acggagcat                                                 19

<210> SEQ ID NO 16
<211> LENGTH: 22
<212> TYPE: DNA
<213> ORGANISM: Artificial sequence
<220> FEATURE:
<223> OTHER INFORMATION: Reverse primer of RT-PCR of mouse gene Dnmt3l

<400> SEQUENCE: 16
ccgagtgtac acctggagag tt                                             22

<210> SEQ ID NO 17
<211> LENGTH: 28
<212> TYPE: DNA
<213> ORGANISM: Artificial sequence
<220> FEATURE:
<223> OTHER INFORMATION: Forward primer of RT-PCR of mouse gene Ecat1

<400> SEQUENCE: 17
tgtggggccc tgaaaggcga gctgagat                                       28

<210> SEQ ID NO 18
<211> LENGTH: 28
<212> TYPE: DNA
<213> ORGANISM: Artificial sequence
<220> FEATURE:
<223> OTHER INFORMATION: Reverse primer of RT-PCR of mouse gene Ecat1

<400> SEQUENCE: 18
atgggccgcc atacgacgac gctcaact                                       28

<210> SEQ ID NO 19
<211> LENGTH: 24
<212> TYPE: DNA
<213> ORGANISM: Artificial sequence
<220> FEATURE:
<223> OTHER INFORMATION: Forward primer of RT-PCR of mouse gene Eras

<400> SEQUENCE: 19
actgcccctc atcagactgc tact                                           24
```

```
<210> SEQ ID NO 20
<211> LENGTH: 24
<212> TYPE: DNA
<213> ORGANISM: Artificial sequence
<220> FEATURE:
<223> OTHER INFORMATION: Reverse primer of RT-PCR of mouse gene Eras

<400> SEQUENCE: 20
cactgccttg tactcgggta gctg                                          24

<210> SEQ ID NO 21
<211> LENGTH: 24
<212> TYPE: DNA
<213> ORGANISM: Artificial sequence
<220> FEATURE:
<223> OTHER INFORMATION: Forward primer of RT-PCR of mouse gene Esg1

<400> SEQUENCE: 21
gaagtctggt tccttggcag gatg                                          24

<210> SEQ ID NO 22
<211> LENGTH: 20
<212> TYPE: DNA
<213> ORGANISM: Artificial sequence
<220> FEATURE:
<223> OTHER INFORMATION: Reverse primer of RT-PCR of mouse gene Esg1

<400> SEQUENCE: 22
actcgataca ctggcctagc                                               20

<210> SEQ ID NO 23
<211> LENGTH: 23
<212> TYPE: DNA
<213> ORGANISM: Artificial sequence
<220> FEATURE:
<223> OTHER INFORMATION: Forward primer of RT-PCR of mouse gene Fgf4

<400> SEQUENCE: 23
cgtggtgagc atcttcggag tgg                                           23

<210> SEQ ID NO 24
<211> LENGTH: 23
<212> TYPE: DNA
<213> ORGANISM: Artificial sequence
<220> FEATURE:
<223> OTHER INFORMATION: Reverse primer of RT-PCR of mouse gene Fgf4

<400> SEQUENCE: 24
ccttcttggt ccgcccgttc tta                                           23

<210> SEQ ID NO 25
<211> LENGTH: 21
<212> TYPE: DNA
<213> ORGANISM: Artificial sequence
<220> FEATURE:
<223> OTHER INFORMATION: Forward primer of RT-PCR of mouse gene Gapdh

<400> SEQUENCE: 25
aggtcggtgt gaacggattt g                                             21

<210> SEQ ID NO 26
<211> LENGTH: 23
<212> TYPE: DNA
<213> ORGANISM: Artificial sequence
<220> FEATURE:
<223> OTHER INFORMATION: Reverse primer of RT-PCR of mouse gene Gapdh
```

<400> SEQUENCE: 26
tgtagaccat gtagttgagg tca                                          23

<210> SEQ ID NO 27
<211> LENGTH: 28
<212> TYPE: DNA
<213> ORGANISM: Artificial sequence
<220> FEATURE:
<223> OTHER INFORMATION: Forward primer of RT-PCR of mouse gene Gata6

<400> SEQUENCE: 27
accttatggc gtagaaatgc tgagggtg                                     28

<210> SEQ ID NO 28
<211> LENGTH: 28
<212> TYPE: DNA
<213> ORGANISM: Artificial sequence
<220> FEATURE:
<223> OTHER INFORMATION: Reverse primer of RT-PCR of mouse gene Gata6

<400> SEQUENCE: 28
ctgaatactt gaggtcactg ttctcggg                                     28

<210> SEQ ID NO 29
<211> LENGTH: 24
<212> TYPE: DNA
<213> ORGANISM: Artificial sequence
<220> FEATURE:
<223> OTHER INFORMATION: Forward primer of RT-PCR of mouse gene Gdf3

<400> SEQUENCE: 29
gttccaacct gtgcctcgcg tctt                                         24

<210> SEQ ID NO 30
<211> LENGTH: 26
<212> TYPE: DNA
<213> ORGANISM: Artificial sequence
<220> FEATURE:
<223> OTHER INFORMATION: Reverse primer of RT-PCR of mouse gene Gdf3

<400> SEQUENCE: 30
agcgaggcat ggagagagcg gagcag                                       26

<210> SEQ ID NO 31
<211> LENGTH: 21
<212> TYPE: DNA
<213> ORGANISM: Artificial sequence
<220> FEATURE:
<223> OTHER INFORMATION: Forward primer of RT-PCR of mouse gene Hcn1

<400> SEQUENCE: 31
tgaagctgac agatggctct t                                            21

<210> SEQ ID NO 32
<211> LENGTH: 20
<212> TYPE: DNA
<213> ORGANISM: Artificial sequence
<220> FEATURE:
<223> OTHER INFORMATION: Reverse primer of RT-PCR of mouse gene Hcn1

<400> SEQUENCE: 32
ctggcagtac gacgtccttt                                              20

```
<210> SEQ ID NO 33
<211> LENGTH: 24
<212> TYPE: DNA
<213> ORGANISM: Artificial sequence
<220> FEATURE:
<223> OTHER INFORMATION: Forward primer of RT-PCR of mouse gene Isl1

<400> SEQUENCE: 33
ttgtacggga tcaaatgcgc caag                                          24

<210> SEQ ID NO 34
<211> LENGTH: 19
<212> TYPE: DNA
<213> ORGANISM: Artificial sequence
<220> FEATURE:
<223> OTHER INFORMATION: Reverse primer of RT-PCR of mouse gene Isl1

<400> SEQUENCE: 34
aggccacaca gcggaaaca                                                19

<210> SEQ ID NO 35
<211> LENGTH: 20
<212> TYPE: DNA
<213> ORGANISM: Artificial sequence
<220> FEATURE:
<223> OTHER INFORMATION: Forward primer of RT-PCR of mouse gene Kcna4

<400> SEQUENCE: 35
tcattgctct gacctgatgc                                               20

<210> SEQ ID NO 36
<211> LENGTH: 20
<212> TYPE: DNA
<213> ORGANISM: Artificial sequence
<220> FEATURE:
<223> OTHER INFORMATION: Reverse primer of RT-PCR of mouse gene Kcna4

<400> SEQUENCE: 36
tcactcagct ccctcaggat                                               20

<210> SEQ ID NO 37
<211> LENGTH: 20
<212> TYPE: DNA
<213> ORGANISM: Artificial sequence
<220> FEATURE:
<223> OTHER INFORMATION: Forward primer of RT-PCR of mouse gene Kcnh2

<400> SEQUENCE: 37
acgcttactg ccagggtgac                                               20

<210> SEQ ID NO 38
<211> LENGTH: 18
<212> TYPE: DNA
<213> ORGANISM: Artificial sequence
<220> FEATURE:
<223> OTHER INFORMATION: Reverse primer of RT-PCR of mouse gene Kcnh2

<400> SEQUENCE: 38
gccgactggc aaccagag                                                 18

<210> SEQ ID NO 39
<211> LENGTH: 20
<212> TYPE: DNA
<213> ORGANISM: Artificial sequence
<220> FEATURE:
<223> OTHER INFORMATION: Forward primer of RT-PCR of mouse gene Myh
```

```
<400> SEQUENCE: 39
ctcaagctca tggccactct                                               20

<210> SEQ ID NO 40
<211> LENGTH: 21
<212> TYPE: DNA
<213> ORGANISM: Artificial sequence
<220> FEATURE:
<223> OTHER INFORMATION: Reverse primer of RT-PCR of mouse gene Myh

<400> SEQUENCE: 40
gcctcctttg cttttaccac t                                             21

<210> SEQ ID NO 41
<211> LENGTH: 20
<212> TYPE: DNA
<213> ORGANISM: Artificial sequence
<220> FEATURE:
<223> OTHER INFORMATION: Forward primer of RT-PCR of mouse gene Nanog

<400> SEQUENCE: 41
caggtgtttg agggtagctc                                               20

<210> SEQ ID NO 42
<211> LENGTH: 20
<212> TYPE: DNA
<213> ORGANISM: Artificial sequence
<220> FEATURE:
<223> OTHER INFORMATION: Reverse primer of RT-PCR of mouse gene Nanog

<400> SEQUENCE: 42
cggttcatca tggtacagtc                                               20

<210> SEQ ID NO 43
<211> LENGTH: 22
<212> TYPE: DNA
<213> ORGANISM: Artificial sequence
<220> FEATURE:
<223> OTHER INFORMATION: Forward primer of RT-PCR of mouse gene Nppa

<400> SEQUENCE: 43
gaaccagagg ggagagacag ag                                            22

<210> SEQ ID NO 44
<211> LENGTH: 22
<212> TYPE: DNA
<213> ORGANISM: Artificial sequence
<220> FEATURE:
<223> OTHER INFORMATION: Reverse primer of RT-PCR of mouse gene Nppa

<400> SEQUENCE: 44
ccctcagctt gcttttagg ag                                             22

<210> SEQ ID NO 45
<211> LENGTH: 26
<212> TYPE: DNA
<213> ORGANISM: Artificial sequence
<220> FEATURE:
<223> OTHER INFORMATION: Forward primer of RT-PCR of mouse gene Tbx5

<400> SEQUENCE: 45
aaatgaaacc cagcatagga gctggc                                        26
```

```
<210> SEQ ID NO 46
<211> LENGTH: 24
<212> TYPE: DNA
<213> ORGANISM: Artificial sequence
<220> FEATURE:
<223> OTHER INFORMATION: Reverse primer of RT-PCR of mouse gene Tbx5

<400> SEQUENCE: 46
acactcagcc tcacatctta ccct                                            24

<210> SEQ ID NO 47
<211> LENGTH: 22
<212> TYPE: DNA
<213> ORGANISM: Artificial sequence
<220> FEATURE:
<223> OTHER INFORMATION: Forward primer of RT-PCR of mouse gene Tnnt2

<400> SEQUENCE: 47
ggcagcggaa gaggatgctg aa                                              22

<210> SEQ ID NO 48
<211> LENGTH: 25
<212> TYPE: DNA
<213> ORGANISM: Artificial sequence
<220> FEATURE:
<223> OTHER INFORMATION: Reverse primer of RT-PCR of mouse gene Tnnt2

<400> SEQUENCE: 48
gaggcaccaa gttgggcatg aacga                                           25

<210> SEQ ID NO 49
<211> LENGTH: 17
<212> TYPE: RNA
<213> ORGANISM: Mus musculus
<220> FEATURE:
<221> NAME/KEY: 3'UTR
<222> LOCATION: (1)..(17)
<223> OTHER INFORMATION: Fragment of 3'UTR Dnmt3a
<220> FEATURE:
<221> NAME/KEY: misc_feature
<222> LOCATION: (10)..(16)
<223> OTHER INFORMATION: Seed region of miR-203

<400> SEQUENCE: 49
aauaauguac auuucac                                                    17

<210> SEQ ID NO 50
<211> LENGTH: 17
<212> TYPE: RNA
<213> ORGANISM: Artificial sequence
<220> FEATURE:
<223> OTHER INFORMATION: Mutated version of 3'-UTR of Dnmt3a of Mus
      musculus
<220> FEATURE:
<221> NAME/KEY: mutation
<222> LOCATION: (11)..(11)
<223> OTHER INFORMATION: A replaced by C with regard to the natural
      sequence of Dnmt3a mRNA 3' UTR
<220> FEATURE:
<221> NAME/KEY: mutation
<222> LOCATION: (13)..(13)
<223> OTHER INFORMATION: U replaced by A with regard to the natural
      sequence of Dnmt3a mRNA 3' UTR
<220> FEATURE:
<221> NAME/KEY: mutation
<222> LOCATION: (15)..(15)
<223> OTHER INFORMATION: C replaced by A with regard to the natural
      sequence of Dnmt3a mRNA 3' UTR
```

```
<400> SEQUENCE: 50
aauaauguac cuauaac                                                    17

<210> SEQ ID NO 51
<211> LENGTH: 17
<212> TYPE: RNA
<213> ORGANISM: Mus musculus
<220> FEATURE:
<221> NAME/KEY: 3'UTR
<222> LOCATION: (1)..(17)
<223> OTHER INFORMATION: 3'UTR of Dnmt3b
<220> FEATURE:
<221> NAME/KEY: misc_feature
<222> LOCATION: (9)..(15)
<223> OTHER INFORMATION: Seed region of miR-203

<400> SEQUENCE: 51
gaaagcugca uuucaga                                                    17

<210> SEQ ID NO 52
<211> LENGTH: 17
<212> TYPE: RNA
<213> ORGANISM: Artificial sequence
<220> FEATURE:
<223> OTHER INFORMATION: Mutated version of 3'UTR of Dnmtb
<220> FEATURE:
<221> NAME/KEY: mutation
<222> LOCATION: (10)..(10)
<223> OTHER INFORMATION: A replaced by C with regard to the natural
      sequence of Dnmtb mRNA 3' UTR
<220> FEATURE:
<221> NAME/KEY: mutation
<222> LOCATION: (12)..(12)
<223> OTHER INFORMATION: U replaced by A with regard to the natural
      sequence of Dnmtb mRNA 3' UTR
<220> FEATURE:
<221> NAME/KEY: mutation
<222> LOCATION: (14)..(14)
<223> OTHER INFORMATION: C replaced by A with regard to the natural
      sequence of Dnmtb mRNA 3' UTR

<400> SEQUENCE: 52
gaaagcugcc uauaaga                                                    17

<210> SEQ ID NO 53
<211> LENGTH: 25
<212> TYPE: RNA
<213> ORGANISM: Homo sapiens
<220> FEATURE:
<221> NAME/KEY: misc_feature
<222> LOCATION: (1)..(25)
<223> OTHER INFORMATION: hsa-miR203a-5p: Accession MIMAT0031890 in
      miRBase
<220> FEATURE:
<221> NAME/KEY: misc_feature
<222> LOCATION: (11)..(11)
<223> OTHER INFORMATION: a is replaced by g in mmu-miR203-5p
<220> FEATURE:
<221> NAME/KEY: misc_feature
<222> LOCATION: (23)..(25)
<223> OTHER INFORMATION: nucleotides absent from mmu-mi203-5p

<400> SEQUENCE: 53 aggguucuu aacaguucaa caguu                                            25

<210> SEQ ID NO 54
<211> LENGTH: 22
<212> TYPE: RNA
<213> ORGANISM: Mus musculus
```

```
<220> FEATURE:
<221> NAME/KEY: misc_feature
<222> LOCATION: (1)..(22)
<223> OTHER INFORMATION: mmu-miR-203-5p, Accession MIMAT0004547 in
      miRBase
<220> FEATURE:
<221> NAME/KEY: misc_feature
<222> LOCATION: (11)..(11)
<223> OTHER INFORMATION: g is replaced by a in hsa-miR203a-5p

<400> SEQUENCE: 54
agugguucuu gacaguucaa ca                                              22

<210> SEQ ID NO 55
<211> LENGTH: 28
<212> TYPE: DNA
<213> ORGANISM: Artificial sequence
<220> FEATURE:
<223> OTHER INFORMATION: Primer Dnmt3a EcoRI-Fw for PCR amplificacion of
      Dnmt3a

<400> SEQUENCE: 55
gaattcaggg acatgggggc aaactgaa                                        28

<210> SEQ ID NO 56
<211> LENGTH: 30
<212> TYPE: DNA
<213> ORGANISM: Artificial sequence
<220> FEATURE:
<223> OTHER INFORMATION: Primer Dnmt3a EcoRI-Rv for PCR amplificacion of
      Dnmt3a

<400> SEQUENCE: 56
catatgctga ggcagtcatt ttagattcat                                      30

<210> SEQ ID NO 57
<211> LENGTH: 27
<212> TYPE: DNA
<213> ORGANISM: Artificial sequence
<220> FEATURE:
<223> OTHER INFORMATION: Primer Dnmt3b_EcoRI-Fw for PCR amplification of
      Dnmt3b

<400> SEQUENCE: 57
gaattctttt agctcacctg tgtgggg                                         27

<210> SEQ ID NO 58
<211> LENGTH: 28
<212> TYPE: DNA
<213> ORGANISM: Artificial sequence
<220> FEATURE:
<223> OTHER INFORMATION: Primer Dnmt3b_NdeI-Rv for PCR amplification of
      Dnmt3b

<400> SEQUENCE: 58
catatgccag aaaggtaaac tctgggca                                        28

<210> SEQ ID NO 59
<211> LENGTH: 31
<212> TYPE: DNA
<213> ORGANISM: Artificial sequence
<220> FEATURE:
<223> OTHER INFORMATION: Primer Dnmt3l_EcoRI-Fw for PCR amplification of
      Dnmt3l

<400> SEQUENCE: 59
gaattcgaaa tgaatcacca taagatgaaa g                                    31
```

<210> SEQ ID NO 60
<211> LENGTH: 32
<212> TYPE: DNA
<213> ORGANISM: Artificial sequence
<220> FEATURE:
<223> OTHER INFORMATION: Primer Dnmt3l_NdeI-Rv for PCR amplification of Dnmt3l

<400> SEQUENCE: 60
catatgaaca atcctatgat atatttgaaa aa                                    32

<210> SEQ ID NO 61
<211> LENGTH: 27
<212> TYPE: DNA
<213> ORGANISM: Artificial sequence
<220> FEATURE:
<223> OTHER INFORMATION: Primer Dnmt1_NdeI-Rv for PCR amplification of Dnmt1

<400> SEQUENCE: 61
gaattcgtgc tctcacccag agccca                                           27

<210> SEQ ID NO 62
<211> LENGTH: 30
<212> TYPE: DNA
<213> ORGANISM: Artificial sequence
<220> FEATURE:
<223> OTHER INFORMATION: Primer Dnmt1_NdeI-Rv for PCR amplification of Dnmt1

<400> SEQUENCE: 62
catatggctt gacagaagcg ctttattttg                                       30

<210> SEQ ID NO 63
<211> LENGTH: 28
<212> TYPE: DNA
<213> ORGANISM: Artificial sequence
<220> FEATURE:
<223> OTHER INFORMATION: Forward primer of RT-PCR of mouse gene Ecat1

<400> SEQUENCE: 63
tgtggggccc tgaaaggcga gctgagat                                         28

<210> SEQ ID NO 64
<211> LENGTH: 28
<212> TYPE: DNA
<213> ORGANISM: Artificial sequence
<220> FEATURE:
<223> OTHER INFORMATION: Reverse primer of RT-PCR of mouse gene Ecat1

<400> SEQUENCE: 64
atgggccgcc atacgacgac gctcaact                                         28

<210> SEQ ID NO 65
<211> LENGTH: 24
<212> TYPE: DNA
<213> ORGANISM: Artificial sequence
<220> FEATURE:
<223> OTHER INFORMATION: Forward primer of RT-PCR of mouse gene Eras

<400> SEQUENCE: 65
actgcccctc atcagactgc tact                                             24

<210> SEQ ID NO 66
<211> LENGTH: 24
<212> TYPE: DNA
<213> ORGANISM: Artificial sequence
<220> FEATURE:
<223> OTHER INFORMATION: Reverse primer of RT-PCR of mouse gene Eras

<400> SEQUENCE: 66
cactgccttg tactcgggta gctg                                          24

<210> SEQ ID NO 67
<211> LENGTH: 24
<212> TYPE: DNA
<213> ORGANISM: Artificial sequence
<220> FEATURE:
<223> OTHER INFORMATION: Forward primer of RT-PCR of mouse gene Esg1

<400> SEQUENCE: 67
gaagtctggt tccttggcag gatg                                          24

<210> SEQ ID NO 68
<211> LENGTH: 20
<212> TYPE: DNA
<213> ORGANISM: Artificial sequence
<220> FEATURE:
<223> OTHER INFORMATION: Reverse primer of RT-PCR of mouse gene Esg1

<400> SEQUENCE: 68
actcgataca ctggcctagc                                               20

<210> SEQ ID NO 69
<211> LENGTH: 23
<212> TYPE: DNA
<213> ORGANISM: Artificial sequence
<220> FEATURE:
<223> OTHER INFORMATION: Forward primer of RT-PCR of mouse gene Fgf4

<400> SEQUENCE: 69
cgtggtgagc atcttcggag tgg                                           23

<210> SEQ ID NO 70
<211> LENGTH: 23
<212> TYPE: DNA
<213> ORGANISM: Artificial sequence
<220> FEATURE:
<223> OTHER INFORMATION: Reverse primer of RT-PCR of mouse gene Fgf4

<400> SEQUENCE: 70
ccttcttggt ccgcccgttc tta                                           23

<210> SEQ ID NO 71
<211> LENGTH: 24
<212> TYPE: DNA
<213> ORGANISM: Artificial sequence
<220> FEATURE:
<223> OTHER INFORMATION: Forward primer of RT-PCR of mouse gene Gdf3

<400> SEQUENCE: 71
gttccaacct gtgcctcgcg tctt                                          24

<210> SEQ ID NO 72
<211> LENGTH: 26
<212> TYPE: DNA
<213> ORGANISM: Artificial sequence
<220> FEATURE:
<223> OTHER INFORMATION: Reverse primer of RT-PCR of mouse gene Gdf3

<400> SEQUENCE: 72
agcgaggcat ggagagagcg gagcag                                        26

```
<210> SEQ ID NO 73
<211> LENGTH: 25
<212> TYPE: DNA
<213> ORGANISM: Artificial sequence
<220> FEATURE:
<223> OTHER INFORMATION: Forward primer of RT-PCR of rat gene Ccnb1

<400> SEQUENCE: 73
ggagatgaag attctgagag ttctg                                        25

<210> SEQ ID NO 74
<211> LENGTH: 20
<212> TYPE: DNA
<213> ORGANISM: Artificial sequence
<220> FEATURE:
<223> OTHER INFORMATION: Reverse primer of RT-PCR of rat gene Ccnb1

<400> SEQUENCE: 74
gtatgctgct ccacatcgac                                              20

<210> SEQ ID NO 75
<211> LENGTH: 20
<212> TYPE: DNA
<213> ORGANISM: Artificial sequence
<220> FEATURE:
<223> OTHER INFORMATION: Forward primer of RT-PCR of rat gene Gapdh

<400> SEQUENCE: 75
ggcaagttca atggcacagt                                              20

<210> SEQ ID NO 76
<211> LENGTH: 22
<212> TYPE: DNA
<213> ORGANISM: Artificial sequence
<220> FEATURE:
<223> OTHER INFORMATION: Reverse primer of RT-PCR of rat gene Gapdh

<400> SEQUENCE: 76
tggtgaagac gccagtagac tc                                           22

<210> SEQ ID NO 77
<211> LENGTH: 18
<212> TYPE: DNA
<213> ORGANISM: Artificial sequence
<220> FEATURE:
<223> OTHER INFORMATION: Forward primer of RT-PCR of rat gene Myh6

<400> SEQUENCE: 77
gggctggagc actgagag                                                18

<210> SEQ ID NO 78
<211> LENGTH: 20
<212> TYPE: DNA
<213> ORGANISM: Artificial sequence
<220> FEATURE:
<223> OTHER INFORMATION: Reverse primer of RT-PCR of rat gene Myh6

<400> SEQUENCE: 78
gagagaggaa caggcaggaa                                              20

<210> SEQ ID NO 79
<211> LENGTH: 18
<212> TYPE: DNA
<213> ORGANISM: Artificial sequence
<220> FEATURE:
<223> OTHER INFORMATION: Forward primer of RT-PCR of rat gene Myh7
```

<400> SEQUENCE: 79
atggcggatc gagagatg                                              18

<210> SEQ ID NO 80
<211> LENGTH: 18
<212> TYPE: DNA
<213> ORGANISM: Artificial sequence
<220> FEATURE:
<223> OTHER INFORMATION: Reverse primer of RT-PCR of rat gene Myh7

<400> SEQUENCE: 80
ggtcaaaggg cctggtct                                              18

<210> SEQ ID NO 81
<211> LENGTH: 29
<212> TYPE: DNA
<213> ORGANISM: Artificial sequence
<220> FEATURE:
<223> OTHER INFORMATION: Forward primer for DNA mehylation analysis of
      mouse gene Elf5 (a)

<400> SEQUENCE: 81
taaaggttgt aatgaataga tattaggtt                                  29

<210> SEQ ID NO 82
<211> LENGTH: 32
<212> TYPE: DNA
<213> ORGANISM: Artificial sequence
<220> FEATURE:
<223> OTHER INFORMATION: Reverse primer for DNA mehylation analysis of
      mouse gene Elf5 (a)

<400> SEQUENCE: 82
aactacttac ttaaaaacaa ataataacta aa                              32

<210> SEQ ID NO 83
<211> LENGTH: 29
<212> TYPE: DNA
<213> ORGANISM: Artificial sequence
<220> FEATURE:
<223> OTHER INFORMATION: Forward primer for DNA mehylation analysis of
      mouse gene Elf5 (b)

<400> SEQUENCE: 83
taaaggttgt aatgaataga tattaggtt                                  29

<210> SEQ ID NO 84
<211> LENGTH: 27
<212> TYPE: DNA
<213> ORGANISM: Artificial sequence
<220> FEATURE:
<223> OTHER INFORMATION: Reverse primer for DNA mehylation analysis of
      mouse gene Elf5 (b)

<400> SEQUENCE: 84
aaataataac taaatccaaa caaaaaa                                    27

<210> SEQ ID NO 85
<211> LENGTH: 30
<212> TYPE: DNA
<213> ORGANISM: Artificial sequence
<220> FEATURE:
<223> OTHER INFORMATION: Forward primer for DNA mehylation analysis of
      mouse gene Sirt6

```
<400> SEQUENCE: 85
tttggttttt tttaggttat gttaggattt                                    30

<210> SEQ ID NO 86
<211> LENGTH: 27
<212> TYPE: DNA
<213> ORGANISM: Artificial sequence
<220> FEATURE:
<223> OTHER INFORMATION: Reverse primer for DNA mehylation analysis of
      mouse gene Sirt6

<400> SEQUENCE: 86
cacttacctc tacctcccaa taaaaaa                                       27
```